United States Patent
Sacherman et al.

(10) Patent No.: US 12,138,436 B2
(45) Date of Patent: Nov. 12, 2024

(54) INTRATYMPANIC INJECTOR DEVICES AND NEEDLES FOR DELIVERY OF DRUGS AND METHODS OF USE

(71) Applicant: Spiral Therapeutics, Inc., Brisbane, CA (US)

(72) Inventors: Kevin W. Sacherman, Brisbane, CA (US); Andrew Ayoob, Brisbane, CA (US); Signe Erickson, Brisbane, CA (US); Hugo Peris, Brisbane, CA (US); Charles Limb, Brisbane, CA (US); Eugene De Juan, Jr., Brisbane, CA (US)

(73) Assignee: Spiral Therapeutics Inc., South San Francisco, CA (US)

( * ) Notice: Subject to any disclaimer, the term of this patent is extended or adjusted under 35 U.S.C. 154(b) by 479 days.

(21) Appl. No.: 17/433,401

(22) PCT Filed: Feb. 24, 2020

(86) PCT No.: PCT/US2020/019517
§ 371 (c)(1),
(2) Date: Aug. 24, 2021

(87) PCT Pub. No.: WO2020/176419
PCT Pub. Date: Sep. 3, 2020

(65) Prior Publication Data
US 2022/0126028 A1    Apr. 28, 2022

Related U.S. Application Data
(60) Provisional application No. 62/810,162, filed on Feb. 25, 2019.

(51) Int. Cl.
*A61M 5/46* (2006.01)
*A61B 1/227* (2006.01)
*A61M 5/32* (2006.01)

(52) U.S. Cl.
CPC ............ *A61M 5/46* (2013.01); *A61B 1/227* (2013.01); *A61M 5/3287* (2013.01); *A61M 2210/0668* (2013.01)

(58) Field of Classification Search
CPC ............ A61M 5/46; A61M 5/3287; A61M 2210/0668; A61M 2210/0662; A61B 1/227; A61F 11/00; A61F 11/202
See application file for complete search history.

(56) References Cited

U.S. PATENT DOCUMENTS

| | | | |
|---|---|---|---|
| 5,902,264 A * | 5/1999 | Toso | A61M 1/774 604/27 |
| 9,040,701 B2 | 5/2015 | Messeguer et al. | |

(Continued)

FOREIGN PATENT DOCUMENTS

| | | | |
|---|---|---|---|
| EP | 2709685 | 3/2014 | |
| EP | 2709685 B1 * | 5/2016 | ............ A61F 11/002 |

OTHER PUBLICATIONS

International Preliminary Report on Patentability in International Appln. No. PCT/US2020/019517, dated Sep. 2, 2021, 10 pages.

(Continued)

*Primary Examiner* — Scott J Medway
*Assistant Examiner* — Anh Bui
(74) *Attorney, Agent, or Firm* — Fish & Richardson P.C.

(57) ABSTRACT

A system for delivering one or more therapeutics to a region of the ear, the region being internal to a tympanic membrane. The system includes a canal guide configured to be inserted within and fittingly engaged with walls of the ear canal and needle assembly having a flexible shaft sized to extend through the canal guide. The canal guide provides alignment of the needle assembly within the ear canal relative to the tympanic membrane. The canal guide includes a viewing lumen extending between a proximal end to a distal-most end of the canal guide and is sized to remain external to the (Continued)

tympanic membrane. The canal guide includes a guide lumen extending to a distal opening near the distal-most end of the canal guide. The guide lumen curves from a first axis to a second axis. Related devices, systems, and methods are provided.

12 Claims, 46 Drawing Sheets

(56) References Cited

U.S. PATENT DOCUMENTS

| | | | | |
|---|---|---|---|---|
| 2002/0161379 | A1* | 10/2002 | Kaplan | A61F 11/20 606/109 |
| 2007/0167918 | A1* | 7/2007 | Reed | A61M 3/0254 606/162 |
| 2008/0262468 | A1* | 10/2008 | Clifford | A61M 31/00 604/501 |

OTHER PUBLICATIONS

International Search Report and Written Opinion in International Appln. No. PCT/US2020/019517, dated May 26, 2020, 12 pages.

* cited by examiner

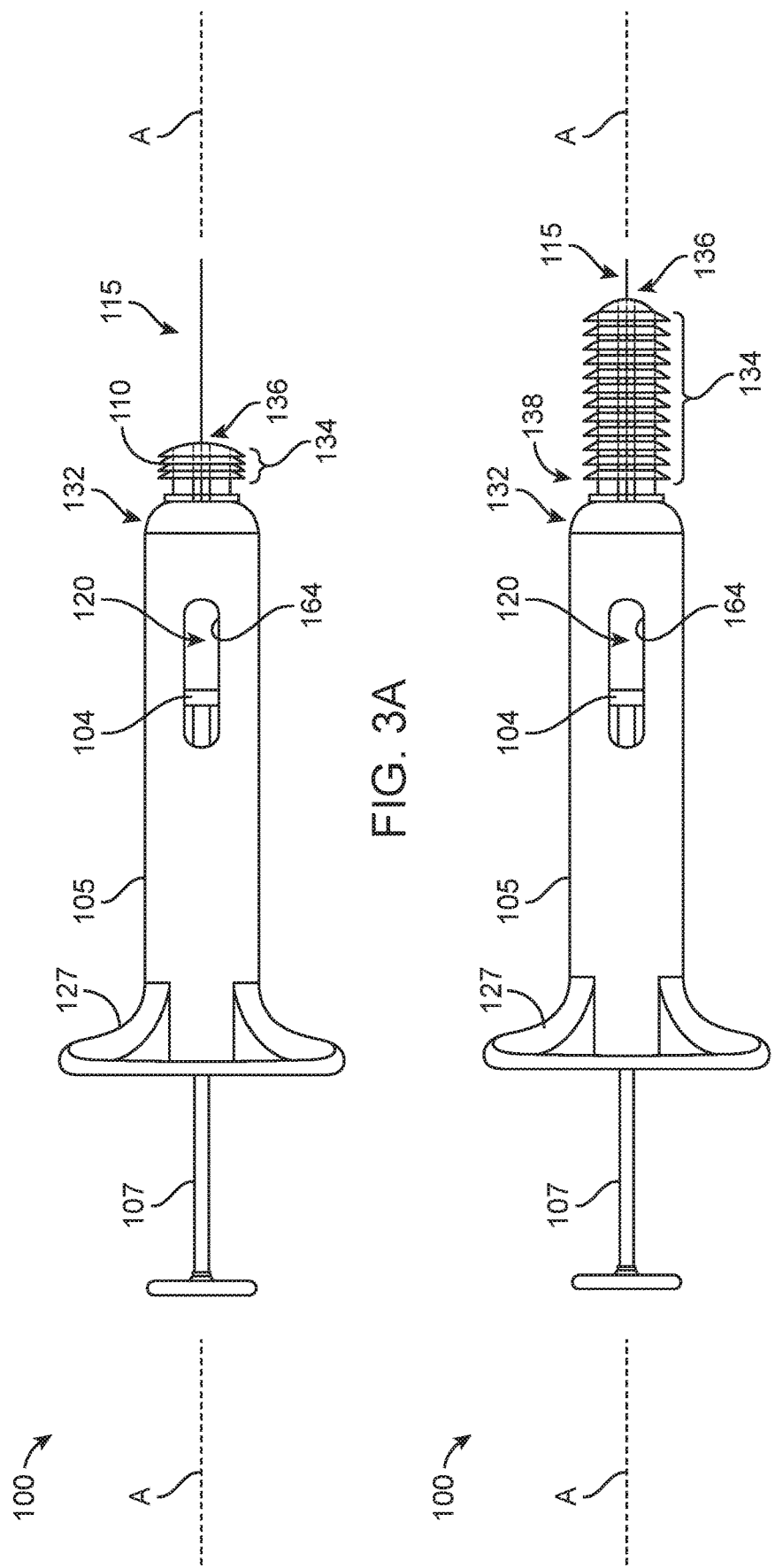

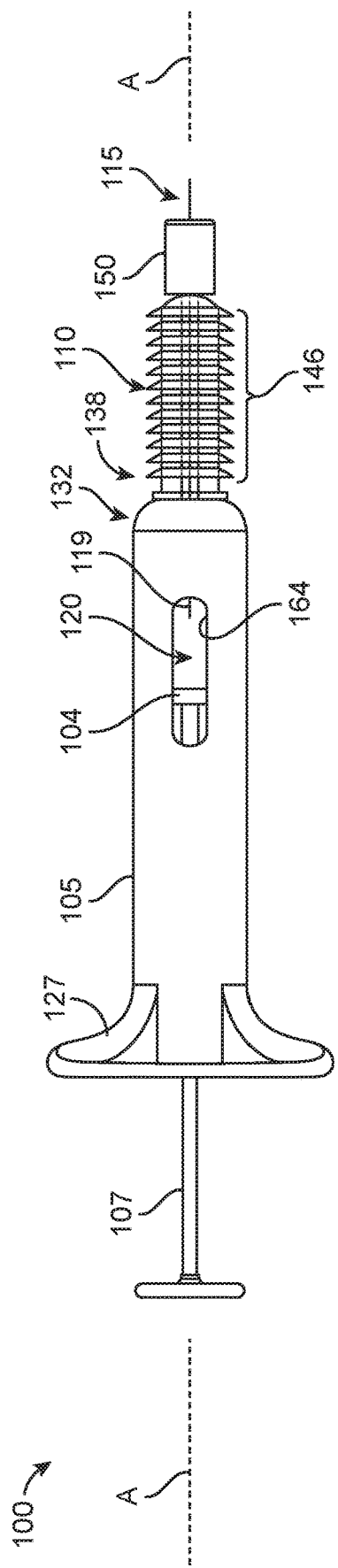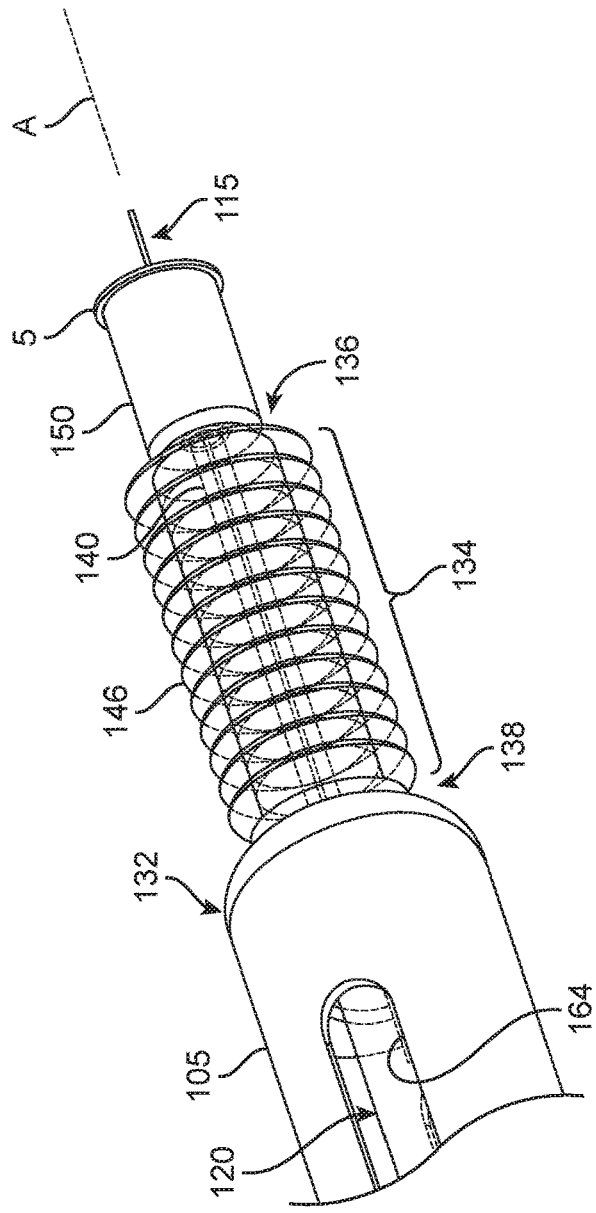
FIG. 3C
FIG. 3D

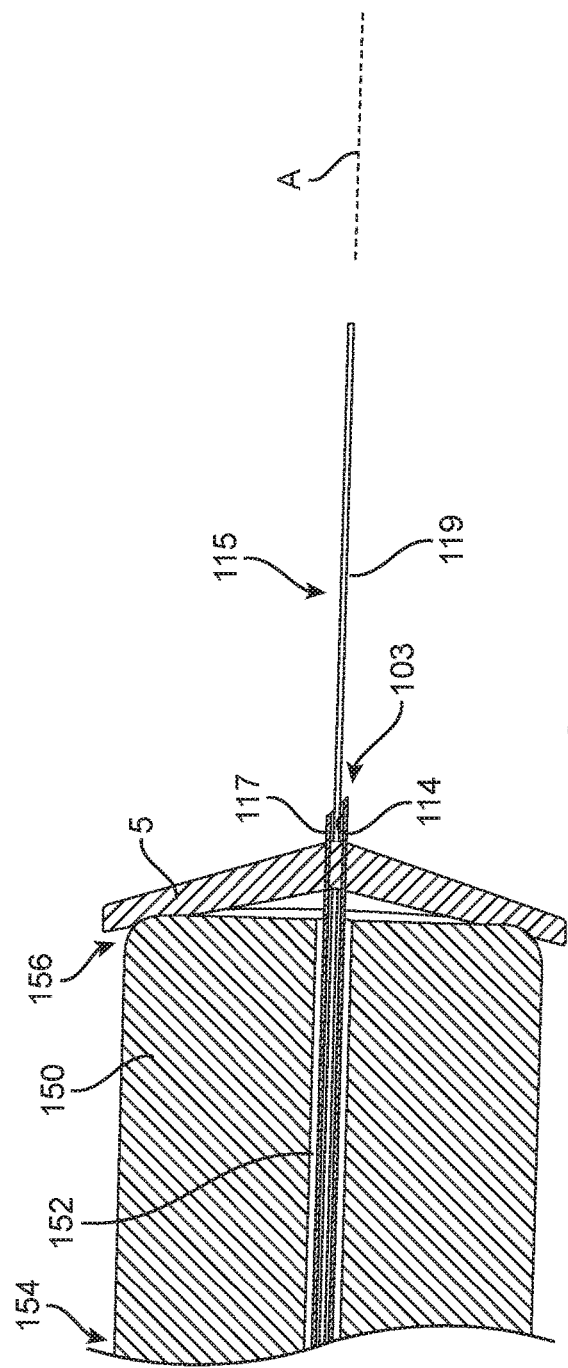
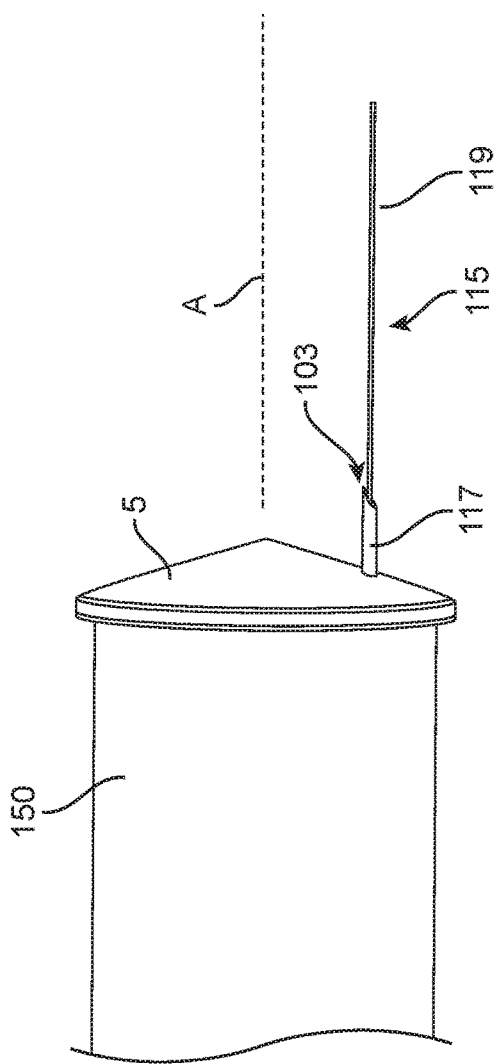

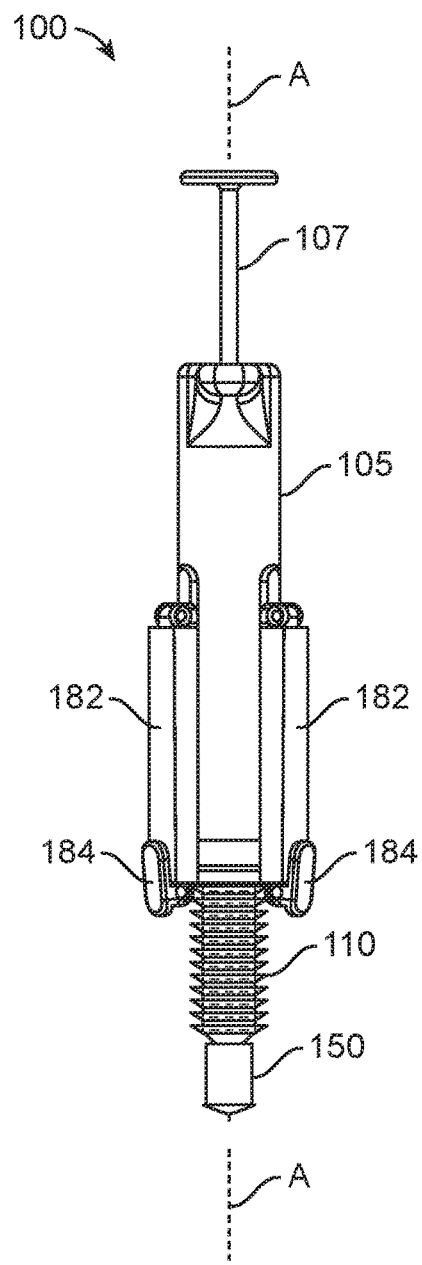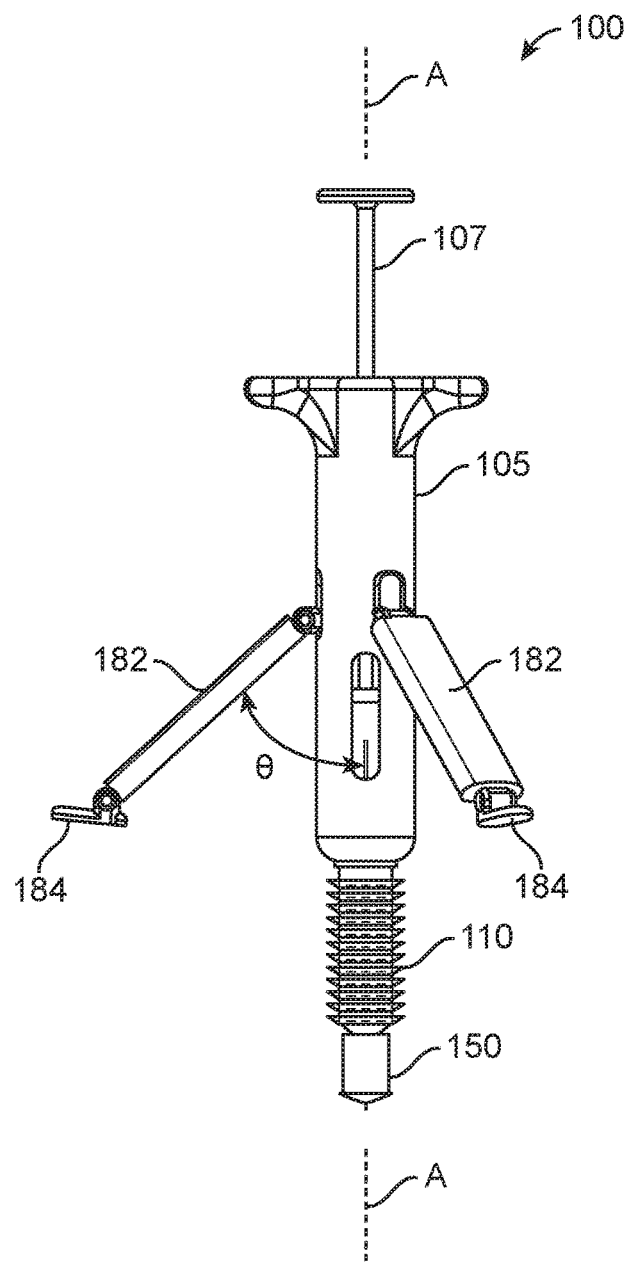
FIG. 5A
FIG. 5B

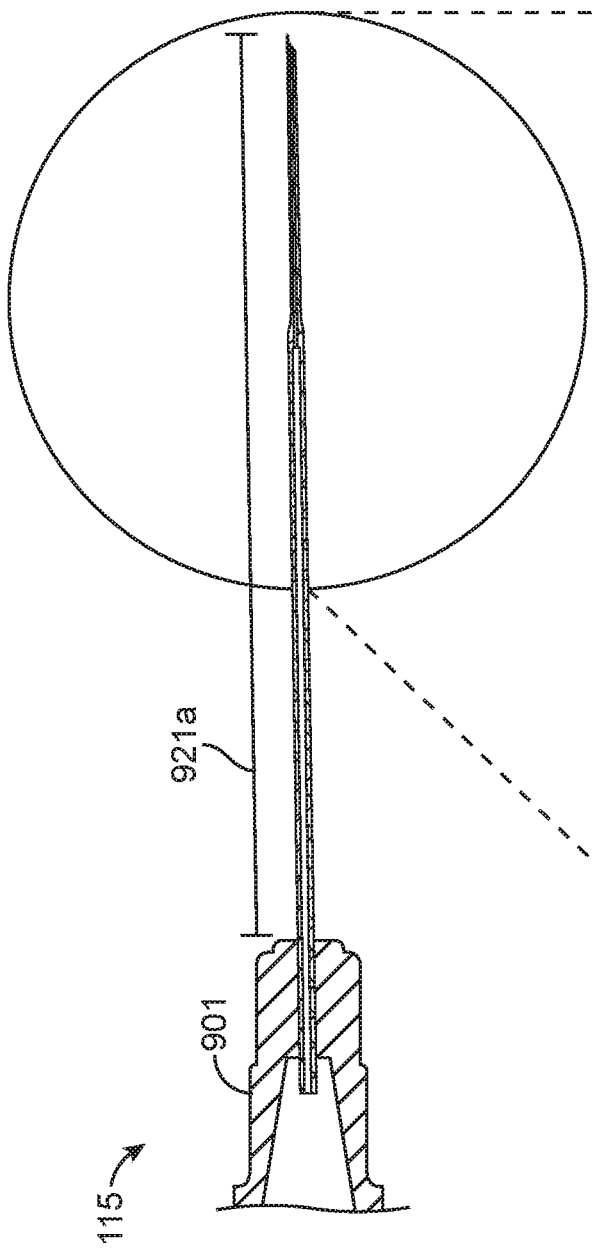
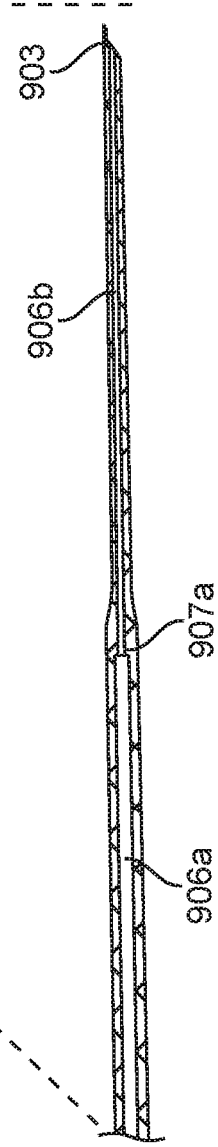
FIG. 20C
FIG. 20D

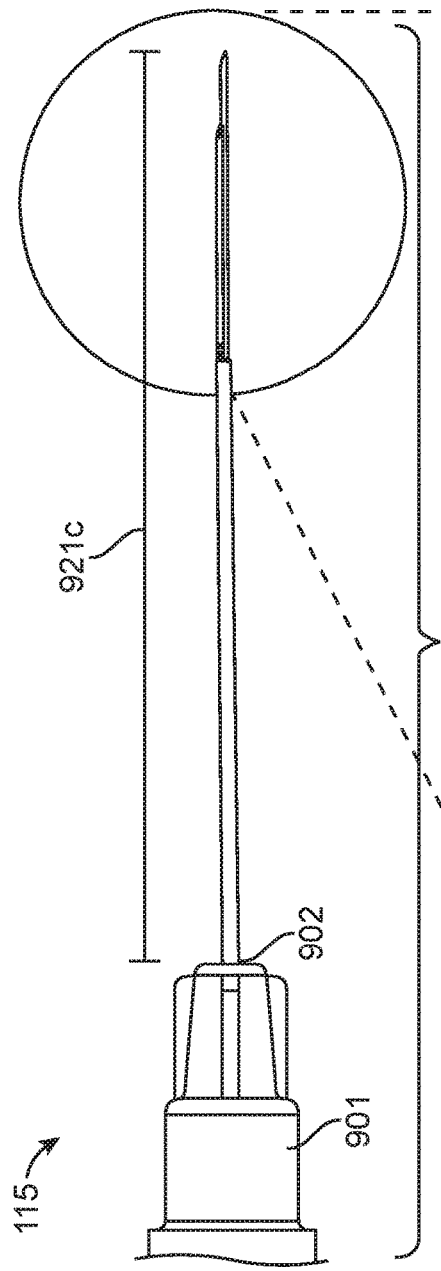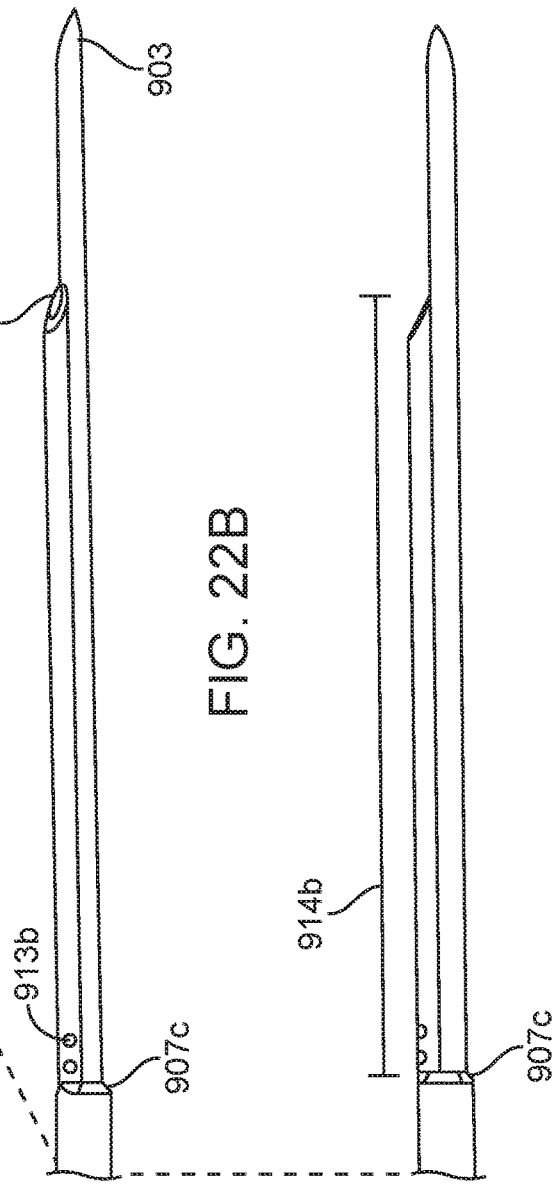
FIG. 22A
FIG. 22B
FIG. 22C

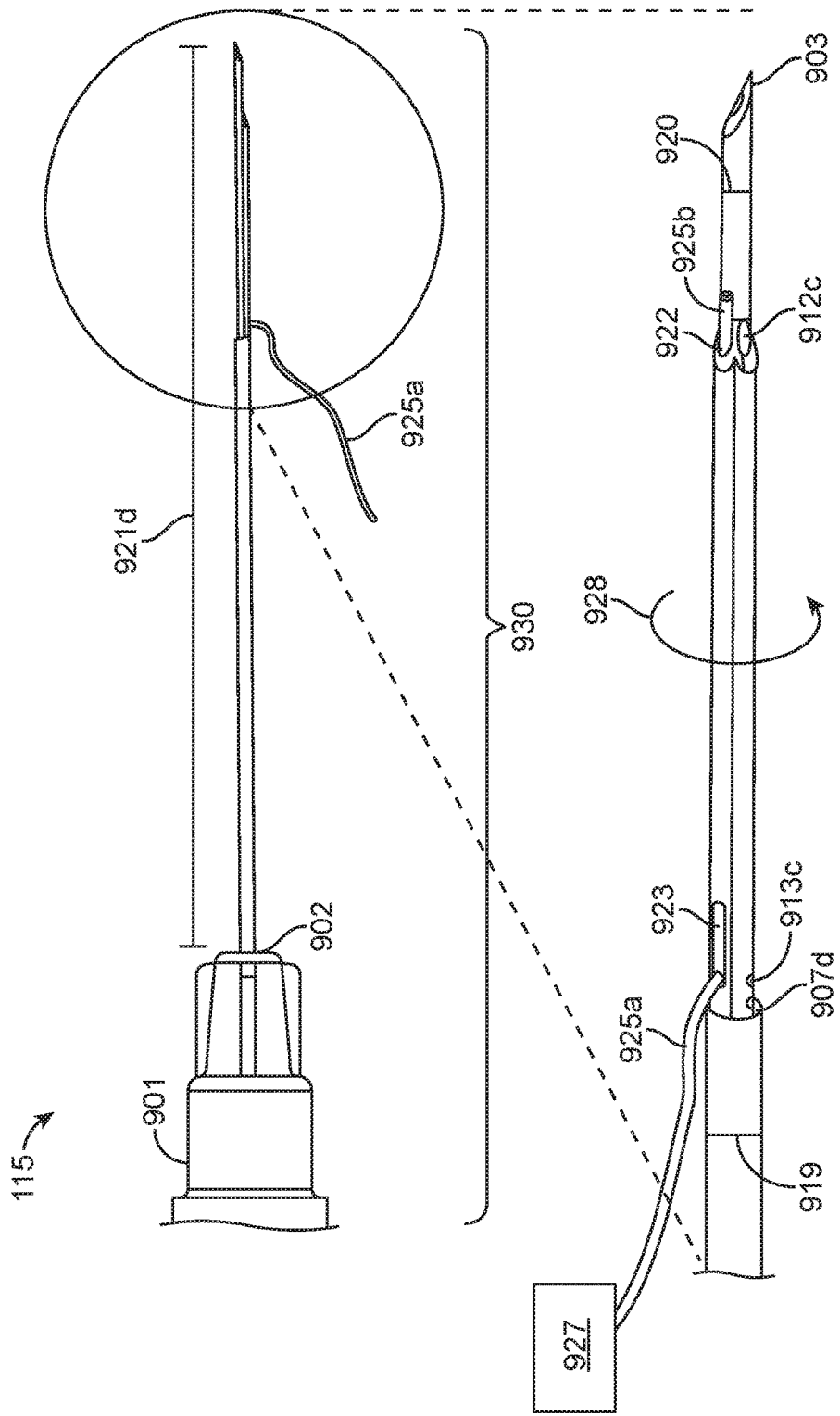

INTRATYMPANIC INJECTOR DEVICES AND NEEDLES FOR DELIVERY OF DRUGS AND METHODS OF USE

CROSS-REFERENCE TO RELATED APPLICATIONS

This application is a U.S. National Phase Application of International Application No. PCT/US2020/019517, filed Feb. 24, 2020, which claims the benefit of priority under 35 U.S.C. § 119(e) to U.S. Provisional Patent Application Ser. No. 62/810,162, filed Feb. 25, 2019, the disclosures of both of which are hereby incorporated by reference in their entirety.

BACKGROUND

Hearing loss can be a result of a variety of ear disorders. SensoriNeural Hearing Loss (SNHL) is most commonly attributed to the loss or dysfunction of hair cells in the cochlea or nerve pathways from the inner ear to the brain. SNHL is typically associated with exposure to loud noise, temporal bone trauma, aging, infection, Meniere's Disease, tumors of the auditory and vestibular nerves, medication-related ototoxicity, genetic diseases (e.g., Usher's disease), and the like.

Potential therapeutic agents to treat hearing loss have been identified. The need exists for safe, direct, and effective drug delivery devices and methods capable of providing therapeutic effect in treating hearing loss and other maladies of the ear, in particular, the middle and inner ear.

SUMMARY

According to a first aspect, disclosed is a system for delivering one or more therapeutics to a region of the ear, the region being internal to a tympanic membrane. The system includes a canal guide configured to be inserted within and fittingly engaged with walls of the ear canal. The canal guide includes a viewing lumen extending between a proximal end of the canal guide to a distal-most end of the canal guide, the distal-most end of the canal guide sized to remain external to the tympanic membrane. The canal guide includes a guide lumen extending from a proximal opening near a proximal end of the canal guide to a distal opening near the distal-most end of the canal guide. The guide lumen curves from a first axis to a second axis, the first axis extending through the proximal opening and the second axis extending through the distal opening. The system includes a needle assembly having a flexible shaft sized to extend through the guide lumen of the canal guide. The flexible shaft includes a fluid delivery lumen. The canal guide provides alignment of the needle assembly within the ear canal relative to the tympanic membrane.

The flexible shaft can include a sharpened tip configured to penetrate the tympanic membrane. The needle assembly can be movable relative to the canal guide between a fully retracted position and a fully extended position. The needle assembly can further include an outer shaft through which the flexible shaft extends. The outer shaft and the flexible shaft can be movable relative to one another and movable to the canal guide. The outer shaft can be rigid and one or both of the flexible shaft and the outer shaft includes a sharpened tip configured to penetrate the tympanic membrane. The needle assembly can be between 23 gauge and 30 gauge. The outer shaft can be extendable a distance from a distal-most end of the canal guide that is no more than about 5 mm to about 10 mm. The flexible shaft can be extendable a distal from the distal-most end of the canal guide that is no more than about 3 mm to about 5 mm. The guide lumen of the canal guide can be eccentric relative to a longitudinal axis of the canal guide. The guide lumen of the canal guide can be adjustable around the longitudinal axis as the canal guide is rotated. The proximal end of the canal guide can include coupling features configured to reversibly engage with coupling features on a forward end of a housing. The canal guide can be adjustably attached to the housing such that the position of the guide lumen relative to the housing can be adjusted by rotation. A degree of rotation of the canal guide relative to the housing can be indicated to a user visually, audibly, and/or tactilely.

The system can further include one or more actuators configured to move the needle assembly relative to the canal guide. The one or more actuators can include a first actuator configured to cause both the outer shaft and the flexible shaft to extend distally relative to a distal-most end of the canal guide and to cause the outer shaft to immediately retract while the flexible shaft remains extended. The needle assembly can be actuated by a spring-loaded mechanism. The flexible shaft can be steerable. The system can further include a steerable guidewire extending through a lumen of the flexible shaft. The flexible shaft can be advanceable over the steerable guidewire. The canal guide can include a conformable outer surface sized to engage with a wall of the ear canal. The conformable outer surface can be at least partly cylindrical in shape. The conformable outer surface can taper towards a narrower outer diameter at the distal-most end. The canal guide can include an inner layer covered by an outer compressible layer. The outer compressible layer can include a plurality of flexible flanges configured to conform to the ear canal upon insertion of the canal guide into the ear canal and advancement of the canal guide towards the tympanic membrane.

The canal guide can be shaped as an ear speculum. The guide lumen can extend along a curved wall of the canal guide between the proximal opening and the distal opening. The distal opening from the guide lumen can be positioned eccentric to a longitudinal axis of the canal guide. The distal-most end of the canal guide can be coupled to a contact tip configured to abut against an outer surface of the tympanic membrane upon insertion and advancement of the canal guide through the ear canal. The contact tip can include a lumen extending from a proximal end to a distal end of the contact tip that is configured to receive the needle assembly. The guide lumen of the canal guide and the lumen of the contact tip can be positioned coaxially with one another. The canal guide can be coupled to a housing. The system can further include one or more collapsible external support legs coupled to a region of the housing. The external support legs can be symmetrically arranged around a longitudinal axis of the canal guide to form a tri-pod of stabilization relative to the canal guide. The external support legs can be positioned adjacent a patient's skull while the canal guide is positioned within the ear canal. The flexible shaft can include a visual marker on its outer surface located a distance proximal to a distal-most tip of the flexible shaft. The flexible shaft can include a plurality of visual markers on its outer surface. A first marker can be positioned distal to a second marker and can be visually distinguishable from the second marker. The needle assembly can include a large bore section that symmetrically tapers at a collar region to the flexible shaft. The flexible shaft can include a trans-tympanic section located distal to the collar region. The trans-tympanic section can be about 1.25 cm long and between 30 and 33 gauge. The large bore section can be about 2.5 cm long and between 20 gauge and 25 gauge. The needle assembly can further include an external ring configured to prevent over-insertion of the needle assembly through the tympanic membrane. The external ring can be positioned at or near the collar region. The needle assembly can further include a concentric vent lumen surrounding the fluid delivery lumen. The needle assembly can further include a vent lumen positioned parallel to the fluid delivery lumen. During use, an outlet from the vent lumen can be positioned external to the tympanic membrane and an outlet from the fluid delivery lumen can be positioned internal to the tympanic membrane.

The needle assembly can further include an optic conduit connecting a proximal opening and a distal opening. The optic conduit can be configured to receive an optic line configured to provide illumination and/or imaging capabilities. The optic line can further include a pressure sensor and/or positional sensor configured to assist with positioning the flexible shaft. A longitudinal axis of the canal guide can extend through the viewing lumen of the canal guide and the guide lumen can be eccentric to the longitudinal axis. The viewing lumen can have a viewing lens at a proximal end. The canal guide can be coupled to a forward end of an upper portion of a housing and a rear end of the upper portion of the housing can include the viewing lens.

The system can further include a reservoir configured to contain the one or more therapeutics for delivery to the region of the ear through the fluid delivery lumen. The reservoir can be integral with the housing or attachable to the housing. The flexible shaft can include a proximal end having an inlet in fluid communication with an outlet from the reservoir. The first axis can form an angle with the second axis, the angle being less than 90 degrees and greater than 0 degrees. The one or more therapeutics can include antioxidants, anti-inflammatories, antimicrobials, anti-allergics, decongestants, sympathomimetics, antineoplastics, NMDA receptor antagonists, nootropics, anti-apoptotic agents, neurotrophins, neuroprotective agents, neural protective proteins, cannabinoids, monoclonal antibodies, gene therapy, iRNA, protein therapy, anti-VEGFs, hormonal agents, beta adrenergic blockers, growth factors, and local anesthetics.

In some variations, one or more of the following can optionally be included in any feasible combination in the above methods, apparatus, devices, and systems. More details of the devices, systems, apparatus, and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

FIG. 3A is an implementation of a device configured to perform intratympanic injections;

FIG. 3B is another implementation of the device of FIG. 3A;

FIGS. 3C-3D is another implementation of the device of FIG. 3A;

FIG. 3F is a cross-sectional view of a distal end region of the device of FIG. 3C;

FIG. 3G is a side view of a distal end region of another implementation of the device of FIG. 3C;

FIG. 5A is a side view of an implementation of the device of FIG. 3C having stabilization features in a collapsed configuration;

FIGS. 5B and 5C are views of the device of FIG. 5A showing the stabilization features in an expanded configuration;

FIGS. 10A, 10B, 10B-1, 10C, and 10C-1 are various views of an implementation of the device of FIG. 4A incorporating an aiming element configured to provide depth guidance;

FIGS. 20A-20D show a single lumen tapered needle according to some implementations;

FIGS. 22A-22D show a needle with a parallel vent lumen according to some implementations;

FIGS. 23A-23C show a needle with a parallel vent lumen and optic line according to some implementations;

DETAILED DESCRIPTION

Figure 1:
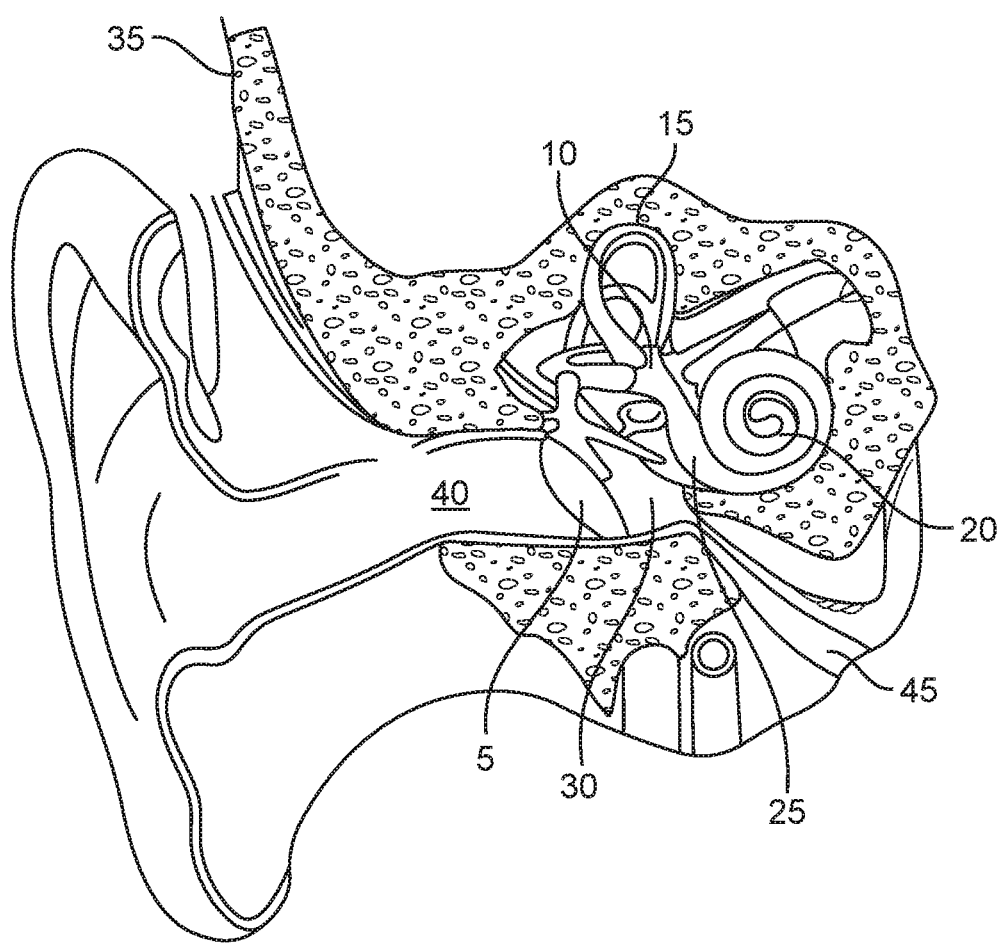
FIG. 1 shows the anatomy of an ear in coronal section view.

Treatment of SNHL, depending on the cause, can include drug treatments for hair cell and cochlear afferent nerve regeneration, reversal of cochlear oxidative stress damage, apoptosis inhibition and reversal of inflammation. There are several drugs in the final stages of clinical development for the treatment of hearing loss including sodium thiosulfate (STS) (Fennec Pharmaceuticals) to protect against cisplatin-induced hearing loss; AM-101 (Auris Medical) for the treatment of tinnitus; AM-111 (Auris Medical) for otoprotection in acute inner ear hearing loss; OTO-104 (Otonomy) for the treatment of Meniere's Disease; SPI-1005 (Sound Pharmaceuticals) for the treatment of mild to moderate acute noise-induced hearing loss and for the treatment of Meniere's Disease.

The inner ear is difficult to treat effectively. For example, the inner ear accounts for only 0.004% of the average circulating blood volume and is encapsulated in one of the densest bones in the body. These, combined with the presence of the blood-labyrinth barrier (BLB) limits access of most therapeutic agents to the inner ear. Oral, intravenous, and intramuscular routes of administration are indirect and require high doses with a potential risk of systemic side effects. Local drug delivery methods are also available. For example, inner ear therapeutics (e.g. drugs formulated as biocompatible gels) can be delivered via intra-tympanic injections into the middle ear across the tympanic membrane (TM). Passive diffusion of agents from the middle ear to the inner ear following intra-tympanic injection has variable efficacy due to anatomical variations, such as presence of pseudomembrane covering the round window membrane, failure of the injected formulation to contact the round window membrane and limited permeability of the round window and oval window membranes. Further, rapid clearance of agents from the perilymph of the inner ear results in the need for repeated intra-tympanic injections, which are undesirable for patients and are associated with cumulative risk of infection, inflammation, and long-term damage to the tympanic membrane, in addition to the risk of lower patient compliance. Accurate placement of formulations in proximity to the round window membrane could greatly improve the effectiveness of therapy, but cannot be readily achieved with current intra-tympanic procedures, which are performed "blindly" without visualization of middle ear structures.

Intratympanic delivery of drugs is typically accomplished by making a small incision in the anesthetized tympanic membrane and applying a drug in liquid form where it resides in the tympanic cavity near the round window. Intratympanic injections are typically performed in an out-patient clinical setting. The tympanic cavity houses a variety of vulnerable structures, such as the malleus, incus, stapes, facial nerve, jugular bulb, and the carotid artery. An accidental contact with any of these structures can result in adverse effects that can include hearing loss, paralysis, or bleeding. Perforations of the tympanic membrane are therefore usually performed in a clinical setting, sometimes under general anesthesia using expensive visual support for the procedure, to prevent accidental penetration, over-penetration, or an unwanted penetration in the wrong location.

In addition to the need to deliver therapeutic agents to middle and inner ear tissues in a controlled, safe, and efficient manner, some therapeutics for the treatment of noise-related SNHL must be delivered shortly after noise exposure (e.g., less than 24 hours after injury). Environments where patients are injured may not be conducive to receiving intratympanic injections, particularly within this short window of time. Examples of therapeutic agents for intratympanic injection include methotrexate, gentamicin, aminoglycosides, steroids, and Apaf1 inhibiting agents, such as LPT99 (see U.S. Pat. No. 9,040,701).

Described herein are devices and systems configured to deliver a therapeutic agent(s) directly to the inner ear or middle ear cavities. The devices and systems described herein provide a more effective administration of therapeutics, whether via intra-tympanic administration or intracochlear administration, by providing access to the middle ear through the ear canal and tympanic membrane. The systems and devices described herein are particularly useful for first-responders in non-clinical settings to deliver therapeutic agent(s) directly to the middle ear for preventing SNHL. It should be appreciated, however, that the devices described herein can be used in clinical settings by physicians and other medical personnel as well. The therapeutic agents also can treat other forms of hearing loss as well as any of a variety of other maladies of the ear. Although specific reference is made below to the delivery of treatments to the ear, it also should be appreciated that medical conditions besides these conditions can be treated with the devices and systems described herein. For example, the devices and systems can deliver treatments for inflammation, infection, and cancerous growths. Any number of drug combinations can be delivered using any of the devices and systems described herein.

The materials, compounds, compositions, articles, and methods described herein may be understood more readily by reference to the following detailed description of specific aspects of the disclosed subject matter and the Examples included therein. Before the present materials, compounds, compositions, articles, devices, and methods are disclosed and described, it is to be understood that the aspects described below are not limited to specific methods or specific reagents, as such may vary. It is also to be understood that the terminology used herein is for the purpose of describing particular aspects only and is not intended to be limiting.

Unless defined otherwise, all technical and scientific terms used herein have the same meaning as is commonly understood by one of skill in the art to which the invention(s) belong. All patents, patent applications, published applications and publications, websites and other published materials referred to throughout the entire disclosure herein, unless noted otherwise, are incorporated by reference in their entirety. In the event that there are pluralities of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, relative directional terms such as anterior, posterior, proximal, distal, lateral, medial, sagittal, coronal, transverse, etc. are used throughout this disclosure. Such terminology is for purposes of describing devices and features of the devices and is not intended to be limited. For example, as used herein "proximal" generally means closest to a user implanting a device and farthest from the target location of implantation, while "distal" means farthest from the user implanting a device in a patient and closest to the target location of implantation.

As used herein, a disease or disorder refers to a pathological condition in an organism resulting from, for example, infection or genetic defect, and characterized by identifiable symptoms.

As used herein, treatment means any manner in which the symptoms of a condition, disorder or disease are ameliorated or otherwise beneficially altered. Treatment also encompasses any pharmaceutical use of the devices described and provided herein.

As used herein, amelioration or alleviation of the symptoms of a particular disorder, such as by administration of a particular pharmaceutical composition, refers to any lessening, whether permanent or temporary, lasting, or transient that can be attributed to or associated with administration of the composition.

As used herein, an effective amount of a compound for treating a particular disease is an amount that is sufficient to ameliorate, or in some manner reduce the symptoms associated with the disease. Such an amount can be administered as a single dosage or can be administered according to a regimen, whereby it is effective. The amount can cure the disease but, typically, is administered in order to ameliorate the symptoms of the disease. Repeated administration can be required to achieve the desired amelioration of symptoms. Pharmaceutically effective amount, therapeutically effective amount, biologically effective amount and therapeutic amount are used interchangeably herein to refer to an amount of a therapeutic that is sufficient to achieve a desired result, i.e. Therapeutic effect, whether quantitative or qualitative. In particular, a pharmaceutically effective amount, in vivo, is that amount that results in the reduction, delay, or elimination of undesirable effects (such as pathological, clinical, biochemical and the like) in the subject.

As used herein, sustained release encompasses release of effective amounts of an active ingredient of a therapeutic agent for an extended period of time. The sustained release may encompass first order release of the active ingredient, zero order release of the active ingredient, or other kinetics of release such as intermediate to zero order and first order, or combinations thereof. The sustained release may encompass controlled release of the therapeutic agent via passive molecular diffusion driven by a concentration gradient across a porous structure.

As used herein, a subject includes any animal for whom diagnosis, screening, monitoring or treatment is contemplated. Animals include mammals such as primates and domesticated animals. An exemplary primate is human. A patient refers to a subject such as a mammal, primate, human, or livestock subject afflicted with a disease condition or for which a disease condition is to be determined or risk of a disease condition is to be determined.

As used herein, a therapeutic agent referred to with a trade name encompasses one or more of the formulation of the therapeutic agent commercially available under the tradename, the active ingredient of the commercially available formulation, the generic name of the active ingredient, or the molecule comprising the active ingredient. As used herein, a therapeutic or therapeutic agents are agents that ameliorate the symptoms of a disease or disorder or ameliorate the disease or disorder. Therapeutic agent, therapeutic compound, therapeutic regimen, or chemotherapeutic include conventional drugs and drug therapies, including vaccines, which are known to those skilled in the art and described elsewhere herein. Therapeutic agents include, but are not limited to, moieties that are capable of controlled, sustained release into the body.

As used herein, a composition refers to any mixture. It can be a solution, a suspension, an emulsion, liquid, powder, a paste, aqueous, non-aqueous or any combination of such ingredients.

As used herein, fluid refers to any composition that can flow. Fluids thus encompass compositions that are in the form of semi-solids, pastes, solutions, aqueous mixtures, gels, lotions, creams and other such compositions.

As used herein, a kit is a packaged combination, optionally, including instructions for use of the combination and/or other reactions and components for such use.

Referring now to the figures, FIG. 1 shows the anatomy of an ear showing the outer ear, the middle ear, and the inner ear as well as a portion of the skull 35 and the Eustachian canal 45. The outer ear includes an auricle and an ear canal 40. The tympanic membrane 5 provides a barrier between the outer ear canal 40 and the middle ear or tympanic cavity 30. The inner ear can be divided into the bony labyrinth and the membranous labyrinth. The structural cavities within the bony labyrinth of the inner ear include the vestibule 10, the semicircular canals 15, and the cochlea 20. Hair cells of the cochlea 20 are critical in transducing acoustic signals into nerve impulses. The hair cells are bathed in secreted fluids such as perilymph supplied by cells that line the bony labyrinth and endolymph found within the membranous labyrinth, which help discern vibrations to assist in the process of hear as well as maintain a sense of balance and equilibrium. The round window 25 includes a round window membrane that in combination with the oval window of the cochlea 20 allow the fluid in the cochlea 20 to move.

Described herein are devices configured to directly access the middle and inner ear through the tympanic membrane. For example, the devices described herein provide access to the middle ear for the direct delivery of one or more therapeutic agent(s) to most effectively treat middle and/or inner ear disorders. Described herein are a variety of devices, which may be used individually or in a variety of combinations to form a system. The features described in the context of one implementation of a device, system, or method are equally applicable to other implementations of a device, system, or method described herein and all such features although may not be explicitly described. Features of the various devices can be used in combination with any of the implementations described herein.

Figure 2A:
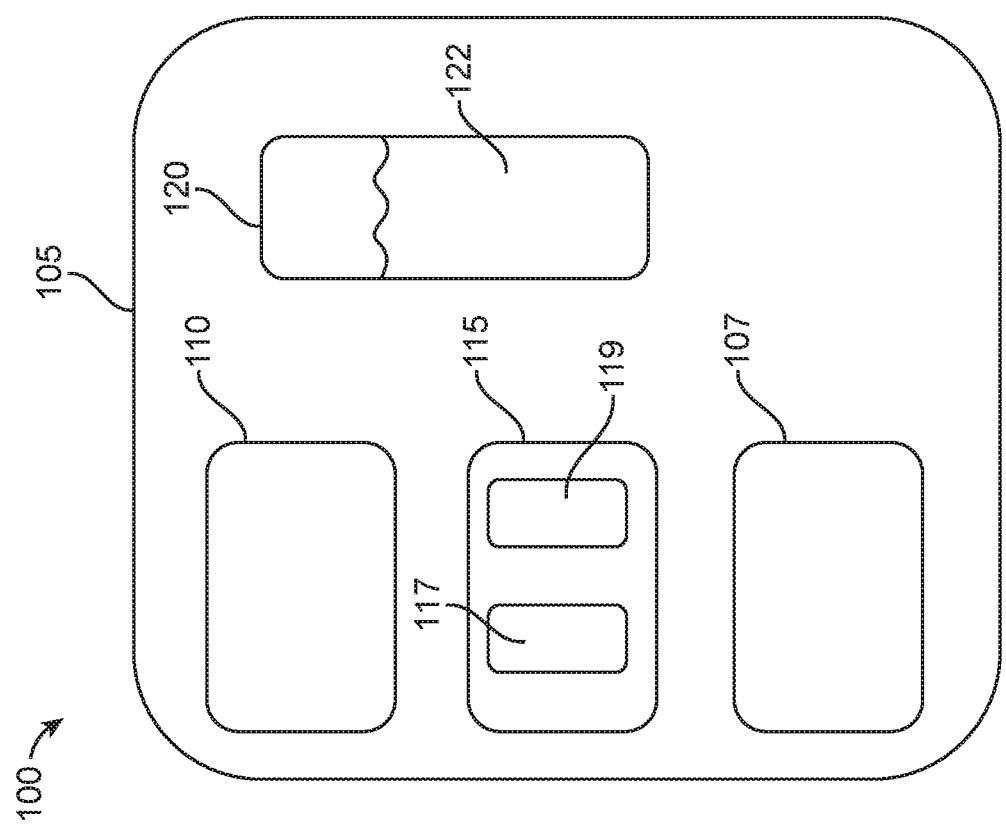
FIG. 2A is a schematic of a device having an integrated reservoir and configured to perform intratympanic injections.
Figure 2B:
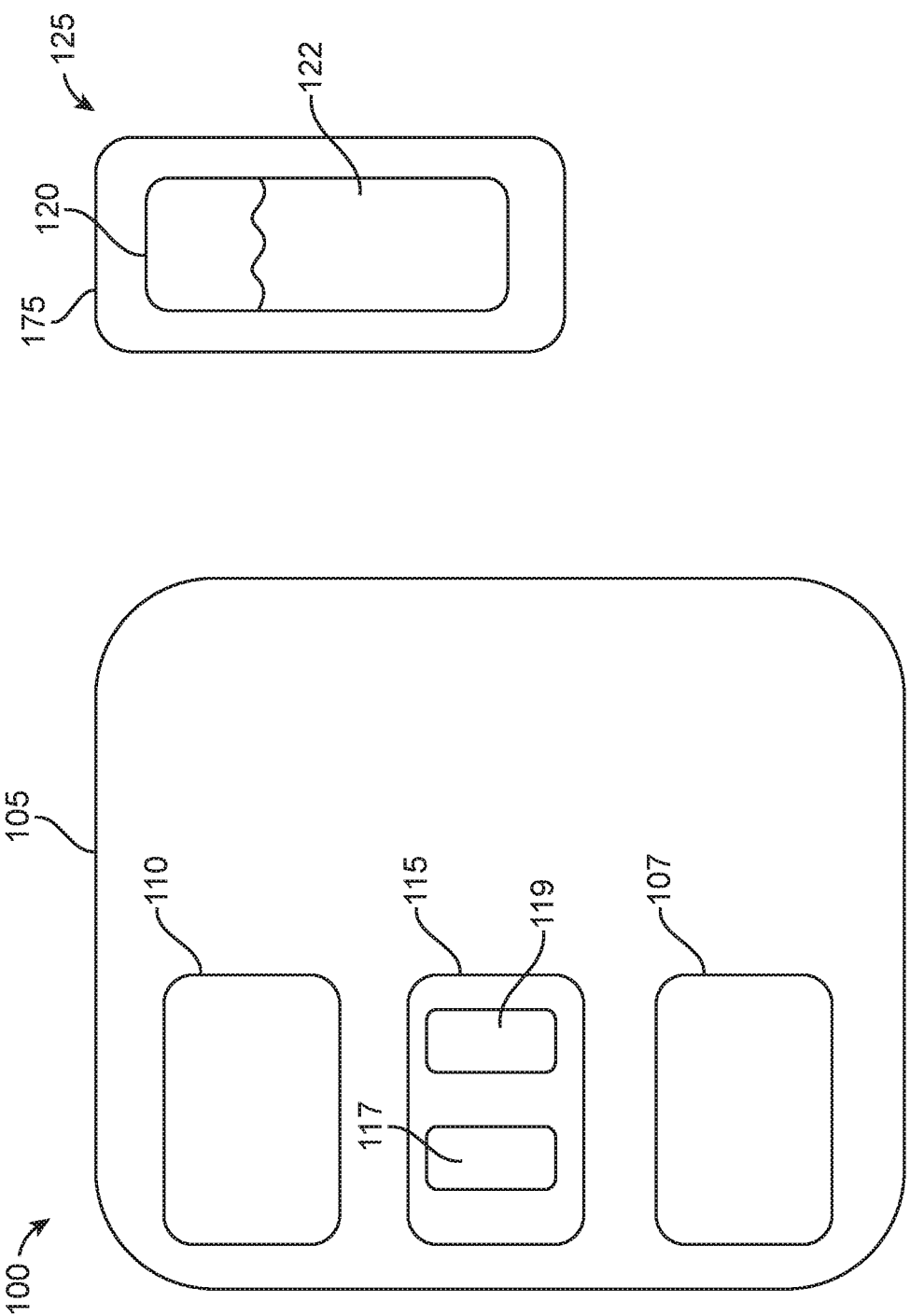
FIG. 2B is a schematic of a device having a removable reservoir and configured to perform intratympanic injections.
Figure 2C:
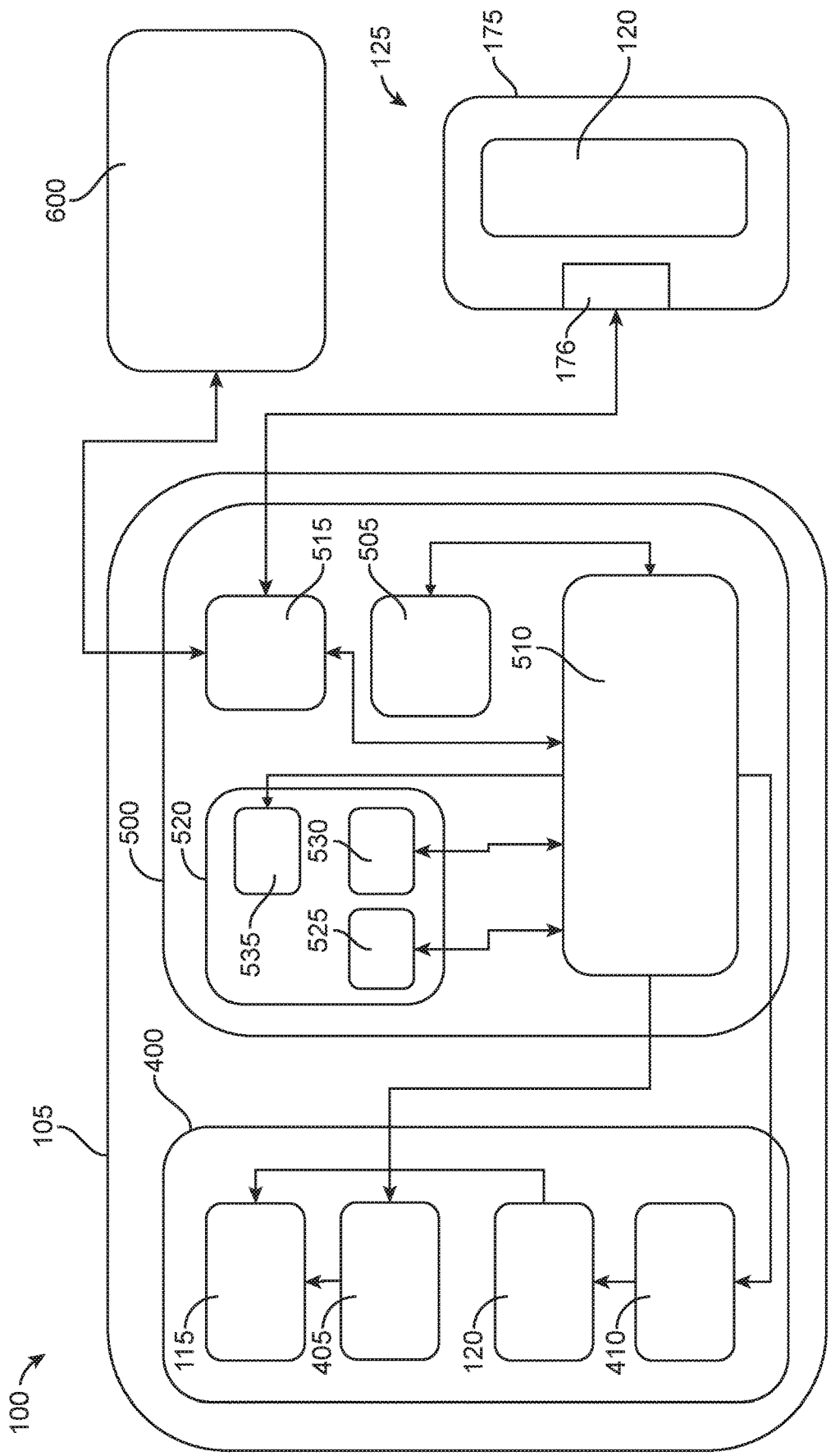
FIG. 2C is a block diagram illustrating an at least partially powered implementation of a device and configured to perform intratympanic injections.

FIGS. 2A-2C illustrate, in schematic, implementations of a device configured to deliver a substance, such as one or more therapeutic agents, to one or more regions of the ear. FIG. 2A is a schematic of a device 100 having a housing 105 with one or more inputs or actuators 107. The device 100 can include a canal guide 110 projecting from a region of the housing 105 that is configured to insert within and fittingly engage the ear canal. A distal-most end of the canal guide 110 is sized to remain external to the tympanic membrane and with sufficient force or friction can inhibit movement of the canal guide 110 within the ear canal during treatments through the canal guide 110. The device 100 can include a needle assembly 115 configured to extend distal to the canal guide 110. The needle assembly 115 can include a flexible shaft sized to be received within and slidingly extend through a lumen of the canal guide 110. The flexible shaft can include a fluid delivery lumen for delivering material to and/or withdrawing material from the middle ear. The canal guide 110 can provide alignment and stabilization of the needle assembly within the ear canal relative to the tympanic membrane. The flexible shaft of the needle assembly can prevent motion transfer to the tympanic membrane upon penetration of the tympanic membrane by the needle assembly.

The needle assembly 115 can include a rigid shaft 117 and a semi-rigid or flexible cannula 119. The device 100 can additionally include a reservoir 120 configured to contain a substance 122 to be delivered to a region of the ear. The reservoir 120 can be integral with the housing 105 as shown in FIG. 2A or the reservoir 120 can be housed within a cartridge 125 configured to reversibly engage with at least a portion of the housing 105 as shown in FIG. 2B. In still further configurations, the reservoir 120 can be within a syringe barrel of a syringe configured to couple with a needle assembly 115 that reversibly engages with at least a portion of the housing 105. Actuation of the device 100 injects the substance 122 from the reservoir 120 through the fluid delivery lumen of cannula 119 of the needle assembly 115. Each of these components can vary in structure and dimension, as will be described in more detail below.

The devices described herein can be purely mechanical devices (e.g., a syringe-type actuation mechanism) or can be at least partially powered instruments. In some implementations, as will be described in more detail below, the device incorporates one or more features that can provide stabilization, guidance, and/or visualization to a user allowing for greater control during the procedure and understanding of the relative location of the injection such that informed choices can be made on-the-fly. FIG. 2C is a block diagram illustrating an at least partially powered implementation of the device 100. The device 100 can include an injection module 400 in communication with an electronics module 500. The injection module 400 can vary depending on the implementation of the device 100, but can include one or more of the needle assembly 115 configured to be extended and retracted by a drive element 405, and a pumping mechanism 410 configured to urge fluid from the reservoir 120 towards the patient. The electronics module 500 of the device 100 can include one or more of a user interface 505 including the one or more actuators 107 and a controller 510. The electronics module 500 can also optionally include a communication port 515 and one or more targeting features 520 configured to improve targeting and/or visualization of the injection, which will be described in more detail below.

Devices, systems, instruments, injectors, autoinjectors, drug delivery devices, drug delivery systems, treatment devices, therapeutic devices, and the like are terms that may be used interchangeably herein and are not intended to be limiting to a particular implementation of device over another. For the sake of brevity, explicit descriptions of each of those combinations may be omitted although the various combinations are to be considered herein. Additionally, described herein are different methods for implantation and access of the devices. Provided are some representative descriptions of how the various devices may be used, however, for the sake of brevity explicit descriptions of each method with respect to each system may be omitted.

Figure 3E:
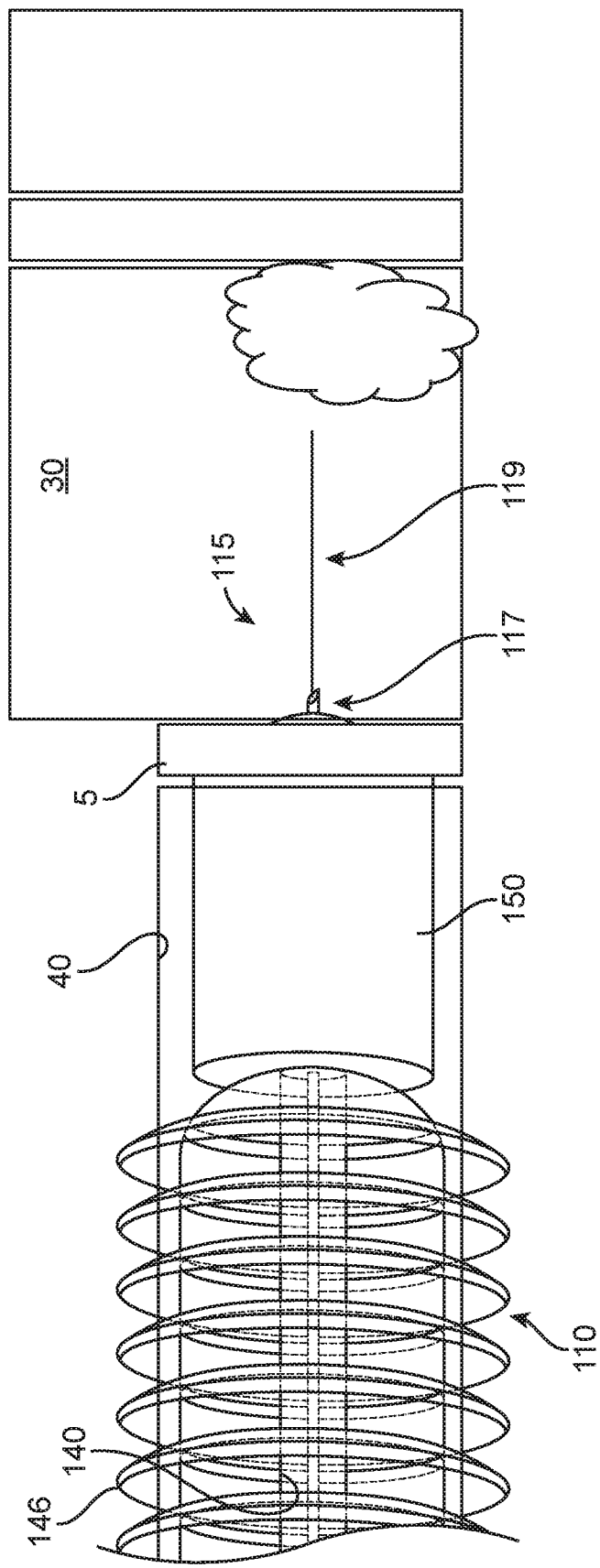
FIG. 3E is a schematic of the device of FIG. 3C positioned relative to the tympanic cavity of the ear.
Figure 4B:
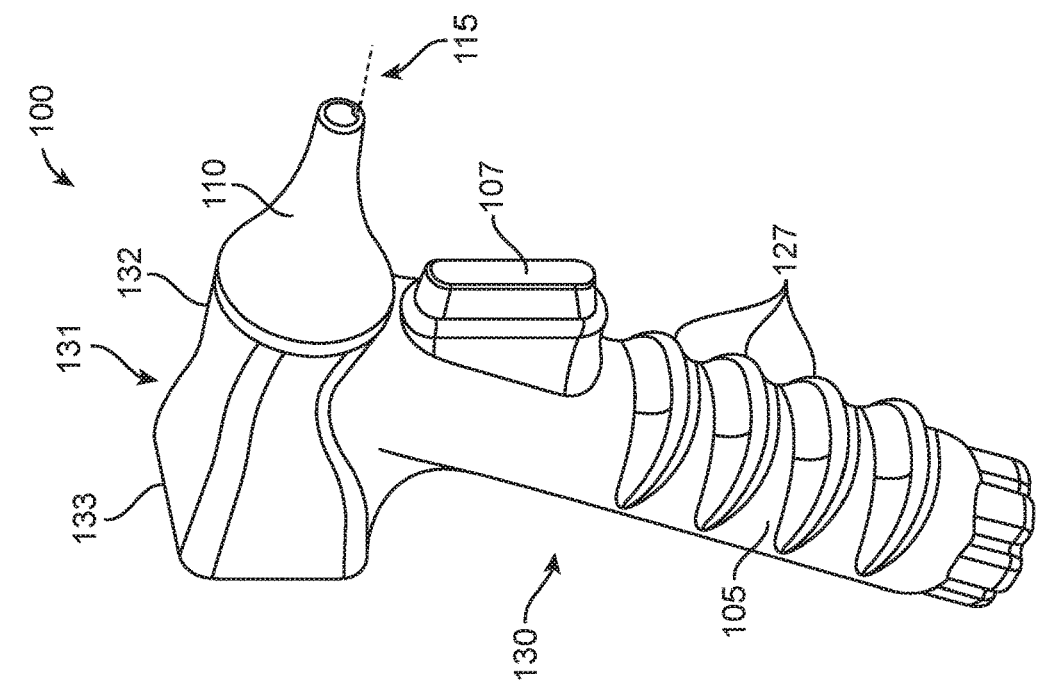
FIGS. 4A-4D are various views of another implementation of a device configured to perform intratympanic injections.
Figure 4A:
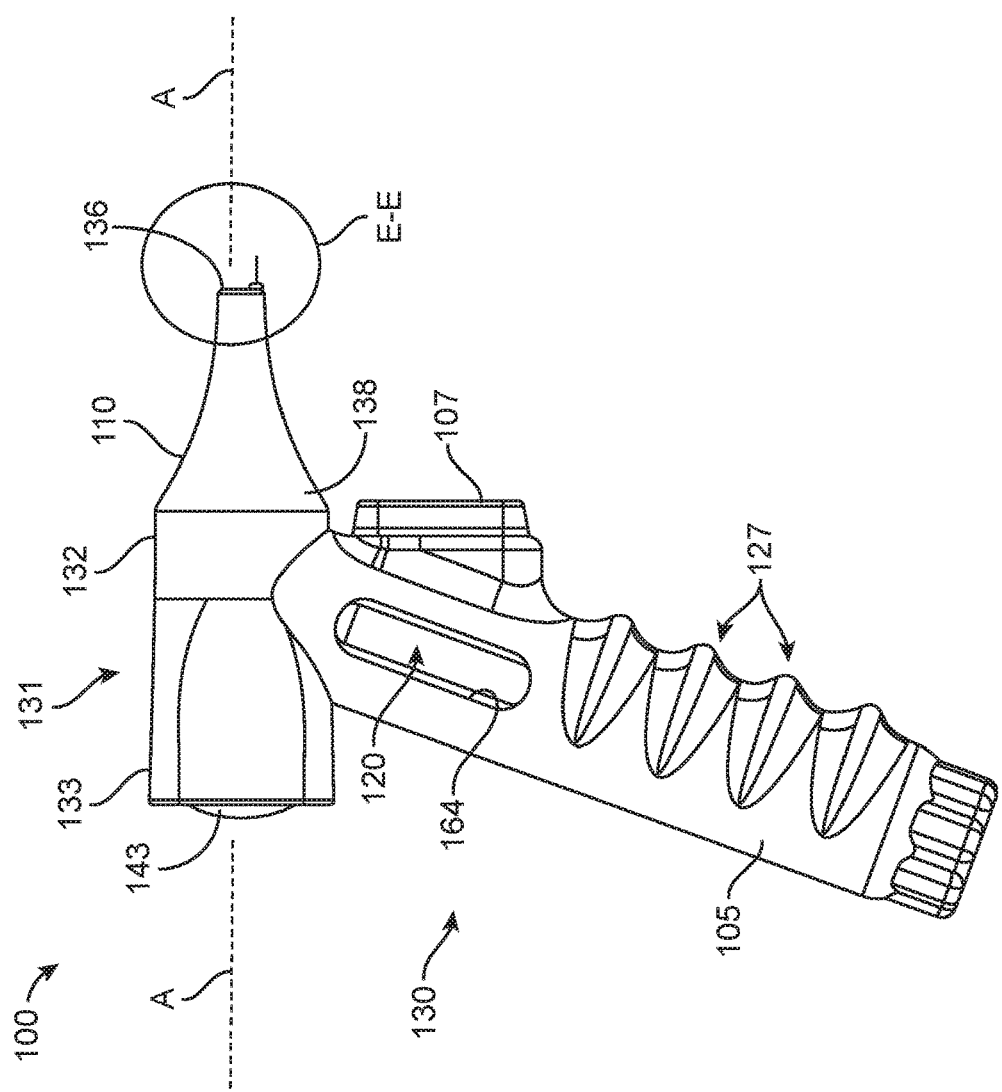
Figure 4D:
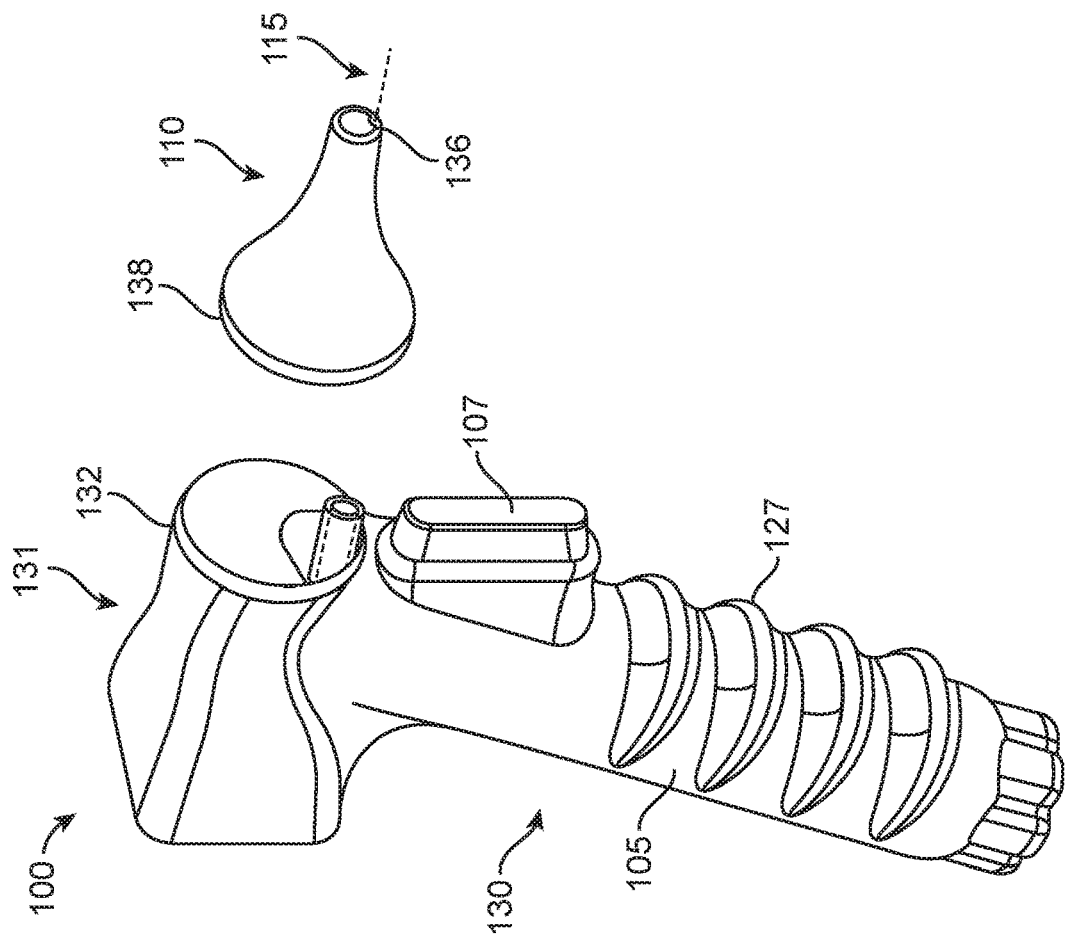
Figure 4C:
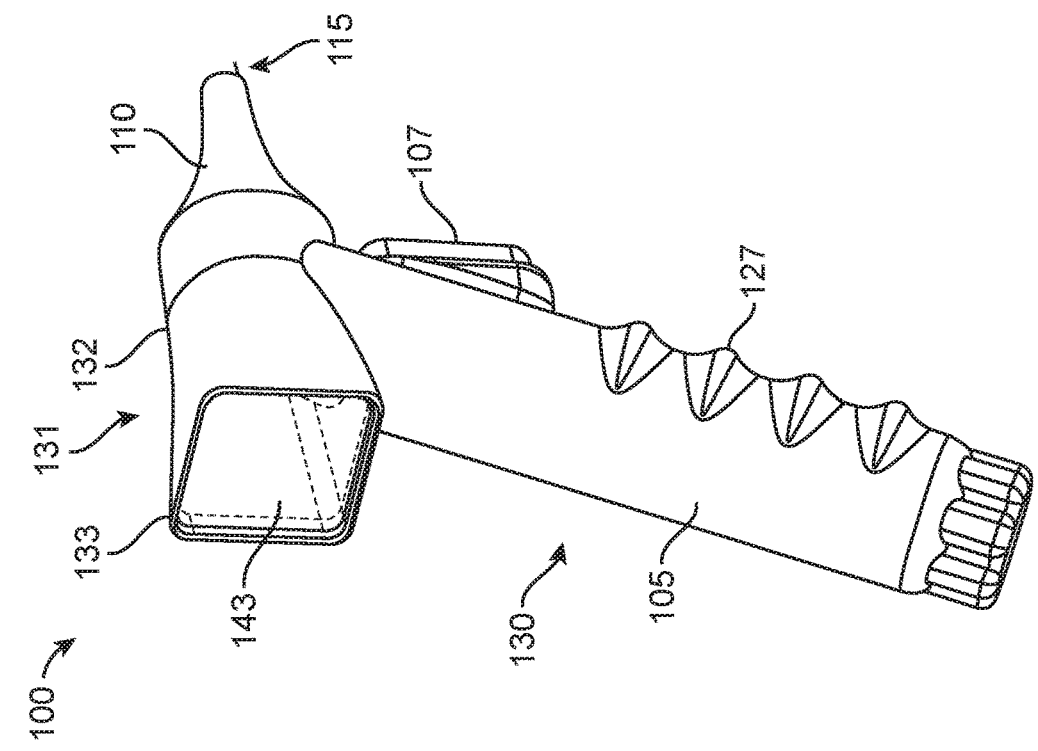
Figure 15A:
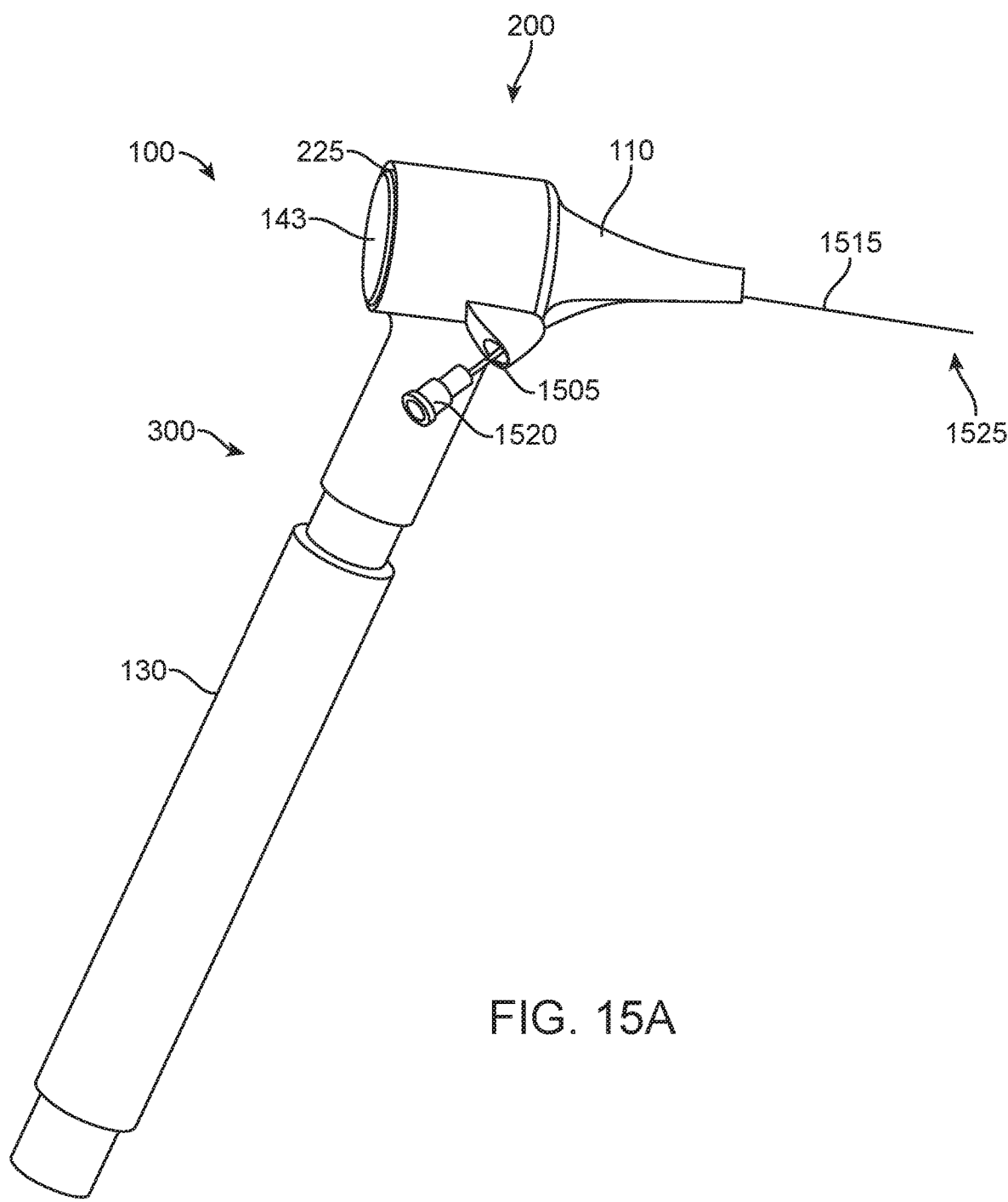
FIGS. 15A-15C are views of another implementation of a device configured to perform intratympanic injections.
Figures 15B, 15C:
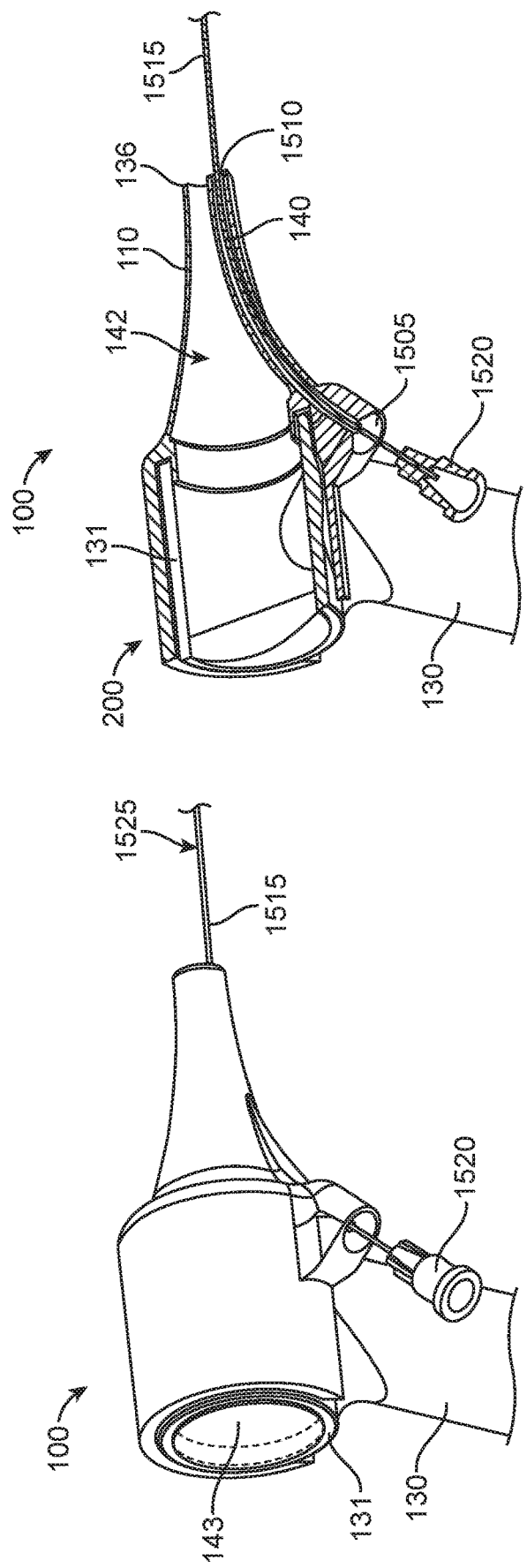

FIGS. 3A-3B illustrate implementations of a device 100 having a housing 105 similar in form factor to a syringe having a plunger. FIGS. 4A-4N and also FIGS. 15A-15C illustrate implementations of a device 100 having a housing 105 similar in form factor to an otoscope. FIGS. 19A-19F illustrate implementations of a device 100 having a housing 105 similar in form factor to an ear speculum tip. The housing 105 can be straight-bodied or a pistol grip type housing. The housing 105 can include one or more gripping features 127 such as indentations or ergonomic features for gripping the device 100. For example, as best seen in FIGS. 4A-4D, the exterior of the housing 105 can include a hand-held portion 130 coupled to an upper portion 131, such as an ergonomic pistol grip. The hand-held portion 130 can be an elongated tubular element having a gripping feature 127 that is a knurled surface that facilitates holding the device 100 in a single hand. The ergonomic hand-held portion 130 can increase stability and reduce the possibility of damage due to unintended movement. The exterior of the housing 105 in the implementation shown in FIGS. 19A-19F include gripping features 127 having knurled surfaces on opposing sides of the viewing channel.

The housing 105, depending on whether the device 100 is intended to be durable or disposable, may be made of a high performance-engineering thermoplastic (e.g. PTFE) or of a metal such as stainless steel or aluminum. The housing 105 can be unitary, single-piece, molded construction or can be formed by two or more panels configured to couple together. The housing 105 can include threaded or friction fit panels configured to be opened to access an interior of the housing 105, for example, to insert or remove battery or a reservoir cartridge 125 as will be described in more detail below.

As mentioned above, the housing 105 can incorporate one or more inputs or actuators 107 such as one or more plungers, triggers, buttons, switches, keys, sliders, or combination thereof mounted on a portion of the housing 105 that are configured to be activated such as retracted, extended, pressed, squeezed, slid, or otherwise actuated to perform a certain function of the device 100. The one or more actuators 107 can be incorporated into a portion of the housing 105 such as a hand-held portion 130 in such a way that is ergonomically comfortable to a user. In some implementations as shown in FIGS. 3A-3B, the actuator 107 can be a syringe plunger configured to urge a piston head 104 through the reservoir 120 to urge the substance from the reservoir 120 out the needle assembly 115. In other implementations as shown in FIGS. 4A-4D, the device 100 may include a pistol grip hand-held portion 130 having a trigger-type actuator 107 such that the device 100 can be easily and comfortably held and actuated during use.

The pistol grip hand-held portion 130 can include other adjustors to modify a user's ergonomics in relation to the patient. For example, the pistol grip hand-held portion 130 can include a hinging element that allows for a user to adjust the angle between the pistol grip hand-held portion 130 and the upper portion 131 of the housing 105. The housing 105 can also be a straight-bodied instrument that does not include a pistol grip handle.

As mentioned, the forward end region 132 of the housing 105 can be coupled to a distal ear canal guide 110. The canal guide 110 can provide alignment and stabilization within the ear canal 40 and direct the needle assembly 115 toward the tympanic membrane 5. In some implementations, the canal guide 110 includes a cylindrical portion 134 having an outer diameter configured for smooth and comfortable insertion and engagement with the ear canal 40. The cylindrical portion 134 of the canal guide 110 can allow for a slight seal to form between the ear canal wall and the outer surface of the canal guide 110. The length of the cylindrical portion can vary. FIG. 3A illustrates an implementation having a canal guide 110 where the cylindrical portion 134 has a first length and FIG. 3B illustrates a further implementation in which the cylindrical portion 134 of the canal guide 110 has a greater length compared to the implementation in FIG. 3A. At least a portion of the canal guide 110 can taper towards the distal-most end 136 such that an outer diameter near the distal-most end 136 of the canal guide 110 is smaller than an outer diameter of the canal guide 110 near where it couples to the housing 105 (see, e.g., FIGS. 3A-3B, 4A-4D). The canal guide 110 can be similar in shape and form factor to an ear speculum (see FIGS. 4A-4D, FIGS. 15A-15C, and FIGS. 19A-19F). For example, the canal guide 110 can include a sloped frustoconical shape and a smooth surface that permits insertion into the ear canal 40 to a limited depth without injuring the ear. Other shapes are considered to improve stabilization and targeting of the tympanic membrane 5.

Figure 4E:
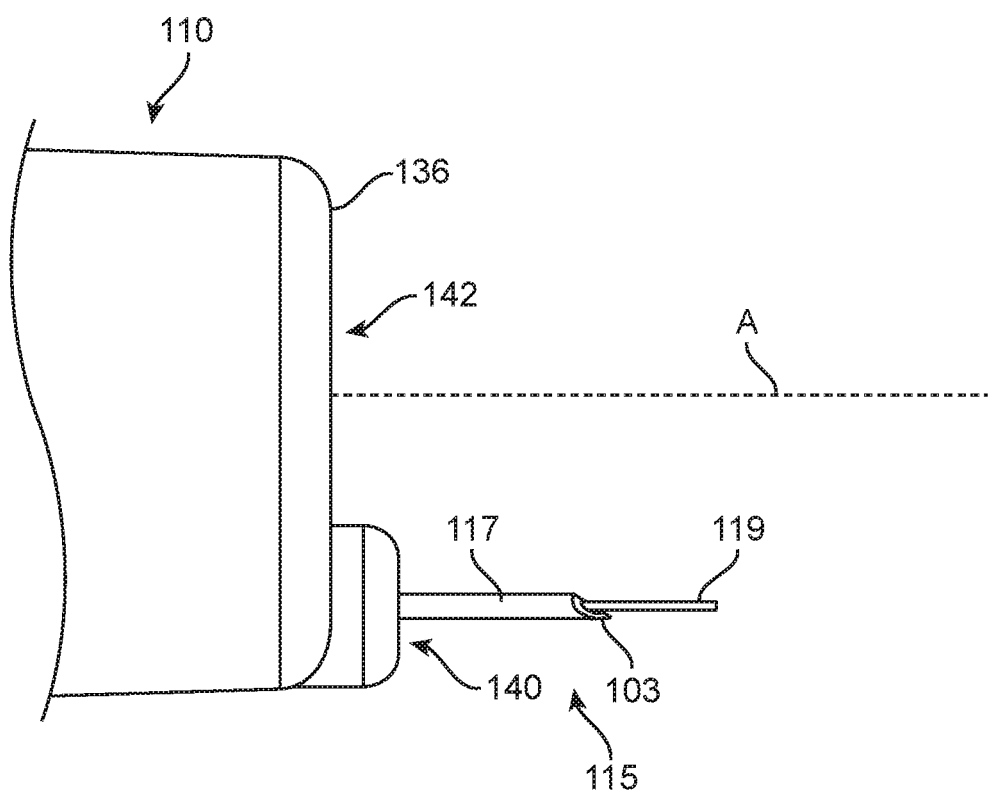
FIG. 4E is a detailed view of the distal end region of the device of FIG. 4A taken at circle E-E.
Figure 4F:
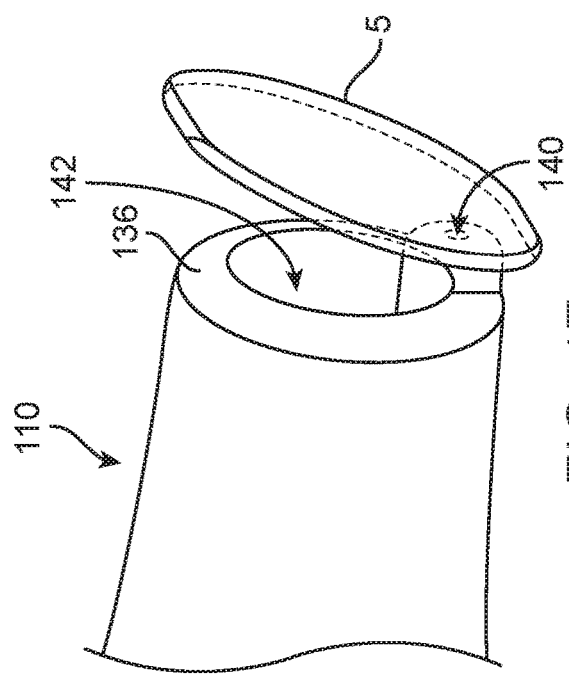
FIGS. 4F-4I are detailed views of the device of FIG. 4E in various configurations of injection relative to a tympanic membrane.

Regardless the configuration and coupling mechanism, the canal guide 110 can include at least a first lumen 140 extending from a proximal end 138 to a distal-most end 136 of the canal guide 110 (see FIGS. 3D and 4E-4F). The lumen 140 can be a guide lumen configured to receive the needle assembly 115, for example, upon extension of the needle assembly 115 relative to the device 100. In some configurations, the canal guide 110 can include at least a second lumen 142 extending from a proximal end 138 to the distal-most end 136 of the canal guide 110 (see FIG. 4E-4I). Where the first lumen 140 of the canal guide 110 is configured to receive the needle assembly 115, the second lumen 142 may be a viewing lumen configured to allow a user to view an object (e.g. the tympanic membrane 5) through the second lumen 142. The second lumen 142 may be arranged relative to magnifying or non-magnifying lens 143 and/or filter assembly similar to an otoscope having a speculum (see FIGS. 4C, 15A, and 19B).

The canal guide 110 can be removed from the device 100. In some implementations, the forward end 132 of the housing 105 can include coupling features such as friction fit, snap fit, threaded features, or other releasable connector, including ejecting mechanisms, configured to engage and disengage with corresponding features on a proximal end of the canal guide 110. The coupling features allow for removal of the canal guide 110 such that the canal guide 110 may be cleaned, sterilized, and reused, or, preferably, disposed of after use. The removable canal guide 110 allows for customization of the device 100 for a particular use in and with a particular patient. For example, the overall size (length and outer diameter) of the removable canal guide 110 can vary depending on whether the device 100 is to be used in an adult or a pediatric patient.

At least a portion of the canal guide 110 can act as a proximal, stabilizing anchor within the ear canal 40 during penetration of the tympanic membrane with the needle assembly. The canal guide 110 can be configured to adjustably anchor against the ear canal 40. In some implementations, the canal guide 110 can have at least a portion configured to enlarge from an insertion configuration having a small outer diameter to a deployed configuration having a larger outer diameter configured to hold the device in place within the ear canal 40. The engagement can be with sufficient force and/or friction against the walls of the surrounding canal 40 to inhibit movement of the canal guide 110 while penetrating the tympanic membrane with the needle assembly. The canal guide 110 can incorporate any of a variety of anchoring features including one or more rings, supports legs, foam, or other anchor. At least a portion of the canal guide 110 can be conformable or compressible such that an outer surface of the canal guide engages with, deforms, and/or takes on the shape of the ear canal 40 upon insertion. In some implementations, the canal guide 110 can include an inner layer covered by an outer conformable or compressible layer. The outer compressible layer can be made from any suitable material known to those skilled in the art, such as compressible foam such as a urethane foam, or silicone over-molded over the inner layer, which can be stiffer than the compressible layer. In some implementations, the outer compressible layer can include a plurality of flexible support rings, discs, or flanges 146 configured to conform to the ear canal 40 upon insertion of the canal guide 110 towards the membrane 5 (see FIGS. 3C-3E). The conformable outer surface can be at least partly cylindrical in shape. The conformable outer surface can taper towards a narrower outer diameter at the distal-most end. The conformable outer surface can have a shape of an ear speculum with sloping, curved walls that taper from a larger flared outer diameter at the proximal end to a smaller, narrow tubular outer diameter at the distal end.

The tympanic membrane 5 is a delicate tissue and prone to damage. However, direct contact with the membrane 5 can provide guidance for attaining proper needle depth for injections. In some implementations, the device 100 is configured to make direct contact with the tympanic membrane 5. FIGS. 3C-3E illustrate an implementation of the device 100 including a canal guide 110 coupled to a forward end region 132 of the housing 105 and the needle assembly 115 extending through the lumen 140. In this implementation, a contact tip 150 is positioned distal to the canal guide 110. The canal guide 110 can provide alignment along the walls of the ear canal 40 and the contact tip 150 can abut against the outer surface of the tympanic membrane 5 (see FIGS. 3E-3G). Similar to the canal guide 110, the contact tip 150 can be a cylindrical element having a lumen 152 extending from a proximal end 154 to a distal end 156 of the contact tip 150 that is configured to receive the needle assembly 115 (see FIG. 3F). As such, the lumen 152 of the contact tip 150 and the first lumen 140 of the ear canal guide 110 can be positioned coaxially with one another. The canal guide 110 in combination with the contact tip 150 can aid in directing the needle assembly 115 through the membrane 5 and into the tympanic cavity 30 or middle ear. In some implementations, the distal-most end 136 of the canal guide 110 can make contact with the tympanic membrane 5.

The surface of the canal guide 110 (or the contact tip 150, if present) at its distal-most end 136 can be disposed approximately in a plane that is normal to or at an angle with respect to the forward end 132 of the housing 105. For example, the surface of the canal guide 110 can be at an angle of about 5, 10, 15, 20, 25, 30, 35, 40, 45 degrees, or other degree angle relative to the plane of forward end 132 of the housing 105.

The needle assembly 115 can be movable relative to the canal guide 110 between a fully retracted position and a fully extended position. Again with respect to FIGS. 3A-3G and also FIGS. 4A-4I, the needle assembly 115 can extend relative to the forward end 132 of the device 100. The needle assembly 115 can be retracted fully within the canal guide 110, for example, during insertion of the canal guide 110 into the ear canal 40 (see FIG. 4F). The needle assembly 115 can be extended outside the canal guide 110, for example, when penetration of the tympanic membrane 5 is desired (see FIGS. 4G-4I). In still further implementations, the needle assembly 115 can be entirely removed from the canal guide 110 until a penetration of the tympanic membrane 5 is desired at which point the needle assembly 115 is coupled to and/or extended beyond the canal guide 110 (see FIGS. 15A-15C and FIGS. 19A-19F).

The needle assembly 115 can include a shaft 117 and a cannula 119. The shaft 117 can be substantially rigid element having a sharpened tip 113 such that the shaft 117 can penetrate the tympanic membrane 5 without a prior incision being formed. The tip 113 geometry can vary, including any of a variety of bevels configured to slice through tissue without causing excessive damage to the tissue upon withdrawal. The cannula 119 can also include various tip geometries, such as beveled tip defining an outlet from the cannula 119 or a closed tipped cannula 119 having one or more side ports. The tip geometry of the cannula 119 can allow directional flow from the cannula 119 to one or more anatomical sites, for example, the round window niche. The cannula 119 can be a semi-rigid or at least partially flexible tubular element. In some implementations, the cannula 119 can be a needle having an at least partially flexible shaft and a distal penetrating tip. The semi-rigid or flexible nature of the cannula 119 mitigates the transfer of unwanted movements of the device 100 to the ear structures such as the tympanic membrane 5. The shaft 117 can be formed of any of a variety of suitable materials, including 316 Stainless Steel as well as nonmetallic materials. The cannula 119 can be formed of any of a variety of suitable materials, including polyimide, PTFE, PEEK, polyamide, or other semi-rigid or suitably flexible materials. In some implementations, the material can be a soft, resilient, stretchable and/or elastic biologically inert material. The flexible, soft material is intended to avoid damaging the delicate middle ear structures as well as avoid transferring movement to the tympanic membrane 5 even upon movement of the housing 105. Instead, the flexible material bends, flexes, or otherwise deforms to avoid tearing or rupturing the membrane 5. Materials include medical grade silicone rubber, medical grade Teflon, and others. The material of the structure can be flexible enough to decouple the operator from the patient such that if the operator's hand moves unintentionally, the motion would not be completely transferred through the cannula 119 positioned through the tympanic membrane.

The configuration of the needle assembly 115 can vary. For example, the cannula 119 can extend through an inner lumen 114 of the shaft 117 or the shaft 117 can extend through a lumen of the cannula 119. The cannula 119 can extend through the inner lumen 114 of the shaft 117 and past the sharpened tip 113 of the shaft 117 to access the middle ear (see FIGS. 3F-3G). In this implementation, both the shaft 117 and cannula 119 can be hollow tubes. Alternatively, the shaft 117 can be configured as a trocar, stylus, or obturator that extends through the lumen of the more flexible cannula 119. In this implementation, the shaft 117 can be solid or hollow. The device 100 need not include a two-part needle assembly 115. For example, in some implementations, the device 100 includes a flexible needle having a sharpened tip allowing for both penetration of the tympanic membrane 5 and prevention of motion transfer to the membrane, which will be described in more detail below (see FIGS. 16-18).

Both the shaft 117 and the cannula 119 of the needle assembly 115 can be movable elements. They can be movable relative to the canal guide 110 of the device as well as to each other. As described above, the needle assembly 115 is configured to insert through the tympanic membrane 5 and into the tympanic cavity 30. The shaft 117 can be urged in a distal direction out from the canal guide 110 to penetrate the tympanic membrane 5. The cannula 119 can move with the shaft 117 in the distal direction such that it penetrates the tympanic membrane 5 by virtue of the shaft 117. The shaft 117 can be immediately retracted back into the canal guide 110 whereas the cannula 119 can maintain its position through the tympanic membrane 5 (see FIG. 4I).

The shaft 117 and cannula 119 can be extended and/or retracted upon activation of one or more actuators 107. The shaft 117 and the cannula 119 of the needle assembly 115 can extend and/or retract relative to the canal guide 110 manually or by electronic actuation using a drive element as will be described in more detail below. Any of a variety of drive elements can be used to extend and/or retract the needle assembly 115 relative to the tympanic membrane 5 such as electrical, mechanical, hydraulic, pneumatic, or their various combinations. For example, linear actuators, screw mechanisms, electromechanical and magnetic linear actuators, hydraulic or pneumatic actuators, as well as many other mechanisms known to those skilled in the art. As an example, activation of an actuator 107 can cause the shaft 117 and the cannula 119 to extend distally relative to the canal guide 110 to penetrate through the target. The shaft 117 can immediately retract proximally and the cannula 119 remain extended. The retraction of the shaft 117 can occur upon further activation of the one or more actuators 107 or can occur automatically without further activation. As another example, the needle assembly 115 can be passed through the tympanic membrane 5 actuated by a spring-loaded mechanism. The spring-loaded mechanism can include an actuator 107 such as a depressible trigger that upon actuation extends the needle assembly 115 and upon a further actuation retracts at least the shaft 117 of the needle assembly 115. The extension of the cannula 119 can be manually adjusted following retraction of the shaft 117, such as with a slider or other incremental adjustor, to achieve optimal extension distance relative to the medial wall of the tympanic cavity 30.

The target location within the middle ear may not align perfectly with the insertion location or trajectory through the tympanic membrane. A steerable guidewire positioned within or along the cannula 119 or shaft 117 can help to steer the needle assembly 115 toward the round window and, for example, away from the attic. For example, the canal guide of the inner shaft 117 of the needle assembly 115 may be used to penetrate the tympanic membrane as described elsewhere herein. Once the membrane is penetrated, the shaft 117 (which may be substantially rigid) can be withdrawn leaving the flexible cannula 119 in place through the membrane. A steerable atraumatic guidewire can be advanced through the fluid delivery lumen of the flexible cannula 119 and steered to the target location. The flexible cannula 119 may then be advanced over the steerable guidewire along the prescribed path to the target location. Alternatively, the steerable atraumatic guidewire may be left in place upon withdrawal of the shaft 117 from the tympanic membrane and steered to the target location. A flexible cannula 119 can then be advanced over the steerable guidewire. Any of a variety of configurations are considered herein.

In some implementations, the needle assembly 115 need not incorporate a separate steerable guidewire. The flexible cannula 119 can be manipulated remotely by the user such that at least a portion of the needle assembly 115 itself is steerable and/or configured to be articulated. For example, the flexible cannula 119 can incorporate one or more pull wires for deflecting a distal end section in a bending plane. Once the sharp tip of the shaft 117 has penetrated the tympanic membrane along a chosen axial trajectory, the insertion trajectory may need to be changed somewhat. For example, the target may reside laterally or caudally away from the insertion trajectory to avoid contact with a particular anatomical site. The cannula 119 can be steered to achieve a prescribed path more suitable for achieving the target location. For example, one or more internal wires can extend between the distal end of the cannula 119 to the proximal end of the cannula 119 such that a user may manipulate the internal wire(s) to control the angle of the distal end of the cannula 119 relative to its longitudinal axis. The wires can be placed in tension to deflect the canal guide and steer the cannula 119 anywhere within a 360 degree range as is known in the art.

In some implementations, the flexible cannula 119 can be fabricated to have a bend or curve along a portion of its length. For example, the material of the flexible cannula 119 can be heat-setting Nitinol. The shape-set cannula 119 can be inserted using a straight shaft extending having a longitudinal axis and being more rigid than the flexible cannula 119. The bend or curve of the cannula 119 when inserted through the more rigid shaft can straighten to take on the shape of the shaft (i.e., straighten to extend parallel to the longitudinal axis of the shaft). The flexible cannula 119 can be "steered" based on the degree of extension of the cannula 119 out the distal opening of the rigid shaft and/or due to rotation of the cannula 119 relative to the shaft during extension. The distal end of the cannula 119 as it extends out from the distal opening of the rigid shaft can relax back into its curved or bent shape-set form. Rotating of the cannula 119 within the lumen of the rigid shaft can direct the distal end of the cannula 119 towards a target site for treatment.

The tympanic cavity 30 can include two parts: the tympanic cavity proper positioned opposite the tympanic membrane 5 and the attic or epitympanic recess located above the level of the membrane 5 (see FIG. 1). The recess contains the upper half of the malleus and the greater part of the incus. Including the attic, the vertical and anteroposterior diameters of the cavity are each about 15 mm. The transverse diameter measures about 6 mm above and 4 mm below; opposite the center of the tympanum, it is only about 2 mm. The tympanic cavity 30 is bounded laterally by the tympanic membrane 5, medially by the lateral wall of the internal ear, behind with the tympanic antrum and through it with the mastoid air cells, and in front with the auditory tube.

The diameter range of the needle assembly 115 can vary. In some implementations, the maximum outer diameter of the needle assembly 115 can be between about 0.30 mm to about 0.60 mm or between 23-30 gauge or between 25-27 gauge. The shaft 117 of the needle assembly 115 can extend a distance from the distal end of the canal guide 110 that is no more than about 5-10 mm. The cannula 119 of the needle assembly 115 can extend a distance from the distal end of the canal guide 110 that is no more than about 3-5 mm. The shaft 117 extension can be long enough to extend distal to the canal guide 110 such that it can be used to penetrate the tympanic membrane 5, but not so long as to approach the otic capsule of the inner ear. The extension of the cannula 119 can be far enough to extend distal to the shaft 117 to approach the otic capsule such that a substance can be delivered to the medial wall of the tympanic cavity 30. In some implementations, the needle assembly 115 can include visual guides (e.g. bands, colors, markers) to inform a user about the relative extension of the needle assembly 115 through the tympanic membrane (see FIGS. 17-18), which will be described in more detail below.

The devices described herein aid in the stabilization and alignment of the device 100 within the ear canal 40 such that the needle assembly 115 can be predictably, efficiently, and safely used to inject a substance without complicated visualization features typical of intratympanic injections performed in clinical settings. The canal guide 110 (and the contact tip 150, if present) aid in the stabilization and alignment of the needle assembly 115 relative to the tympanic membrane 5. In some implementations, the lumen 140 through which the needle assembly 115 extends through the canal guide 110 is aligned with the longitudinal axis A of the canal guide 110 (see FIGS. 3A-3F). In other implementations, the lumen 140 through which the needle assembly 115 extends through the canal guide 110 is eccentric or off-set from the longitudinal axis A of the canal guide 110 (see, e.g., FIGS. 3G, 4A, and 4E). In other implementations, the lumen 140 through which the needle assembly 115 extends through the canal guide 110 is eccentric to the longitudinal axis A of the canal guide 110 and curves from a first axis to a second axis (see, e.g., FIGS. 15A-15C and 19A-19F). This allows for the canal guide 110 is be positioned within the ear canal 40 snugly against the walls of the canal 40 leading to the tympanic membrane 5 and penetrate with the needle assembly 115 a quadrant of the tympanic membrane 5 located away from the ossicular chain thereby reducing the risk of structural damage.

Figure 4G:
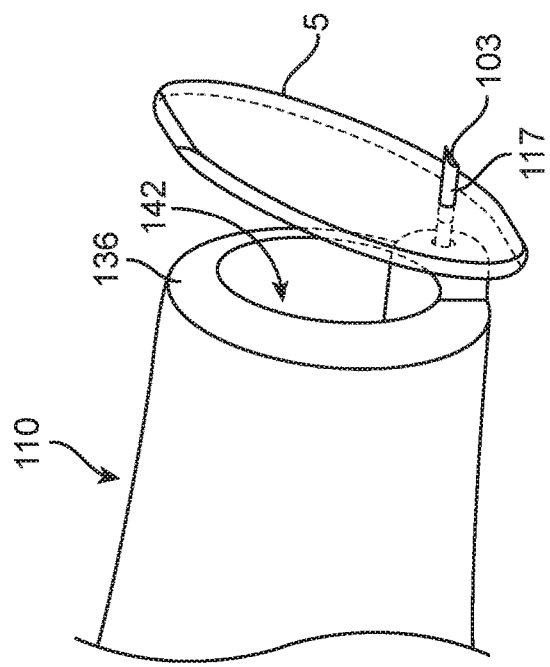
Figure 4H:
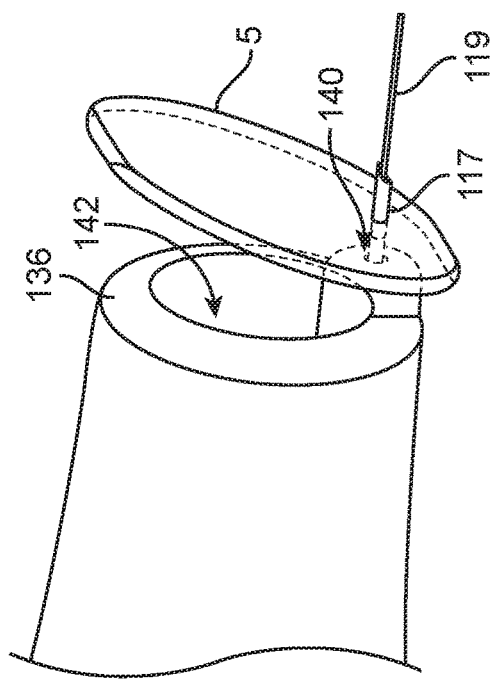
Figure 4I:
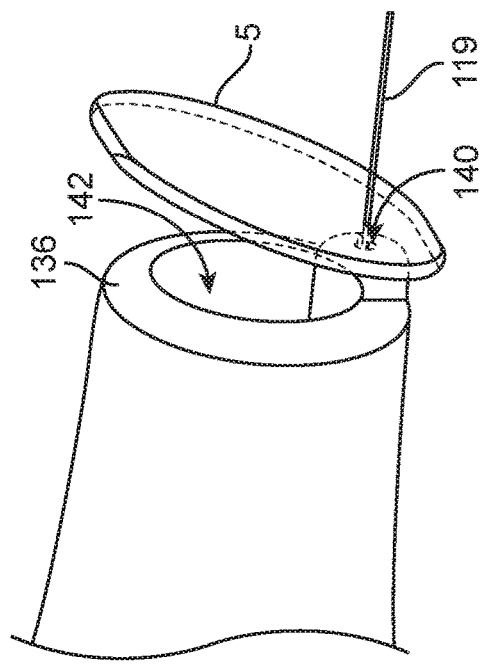

FIG. 4F shows the distal end 136 of the canal guide 110 with the needle assembly 115 substantially retracted such that the sharpened tip 113 of the shaft 117 is prevented from inadvertently penetrating ear tissue. The distal end 136 of the canal guide 110 is shown positioned within the ear canal 40 adjacent to the tympanic membrane 5 such that a quadrant of the membrane 5 located away from the ossicular chain is targeted for penetration by the needle assembly 115. FIG. 4G shows the shaft 117 of the needle assembly 115 extended through the tympanic membrane 5. FIG. 4H shows the inner delivery cannula 119 extending through the shaft 117 and the membrane 5 such that the distal end of the cannula 119 is positioned within the middle ear. FIG. 4I shows the shaft 117 of the needle assembly 115 retracted and the inner delivery cannula 119 remaining within the middle ear extending through the tympanic membrane 5. The shaft 117 can act as an introducer to pass the less rigid delivery cannula 119 into the middle ear before being promptly retracted back into the lumen 140 of the canal guide 110. The off-axis needle assembly 115 relative to the longitudinal axis A of the canal guide 110 mitigates damage to delicate structures near the attic. The semi-rigid or flexible nature of the inner delivery cannula 119 mitigates the risk of tympanic membrane damage in the event of unwanted inadvertent movement in the housing 105 of the device 100 while the needle assembly 115 is in place for injection.

Figure 4K:
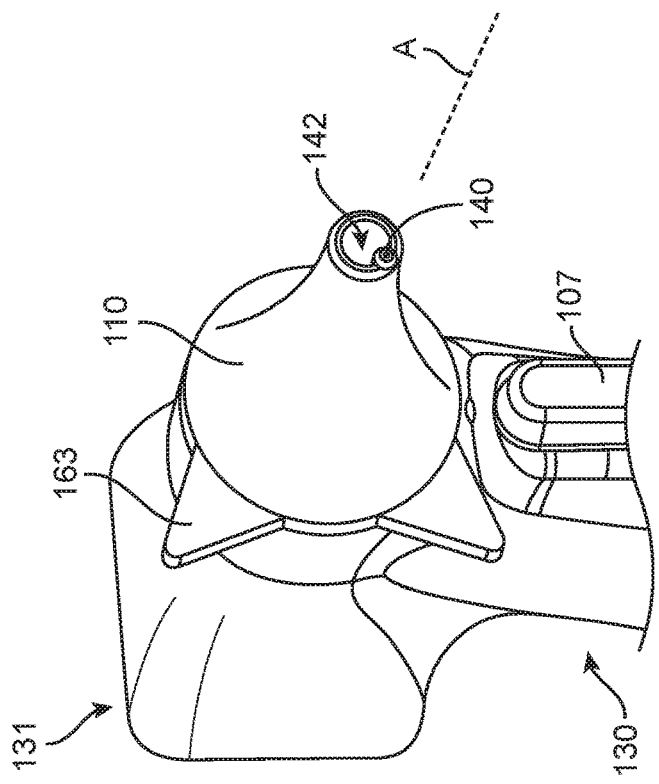
FIGS. 4J-4K are partial views of another implementation of the device of FIG. 4A.
Figure 4J:
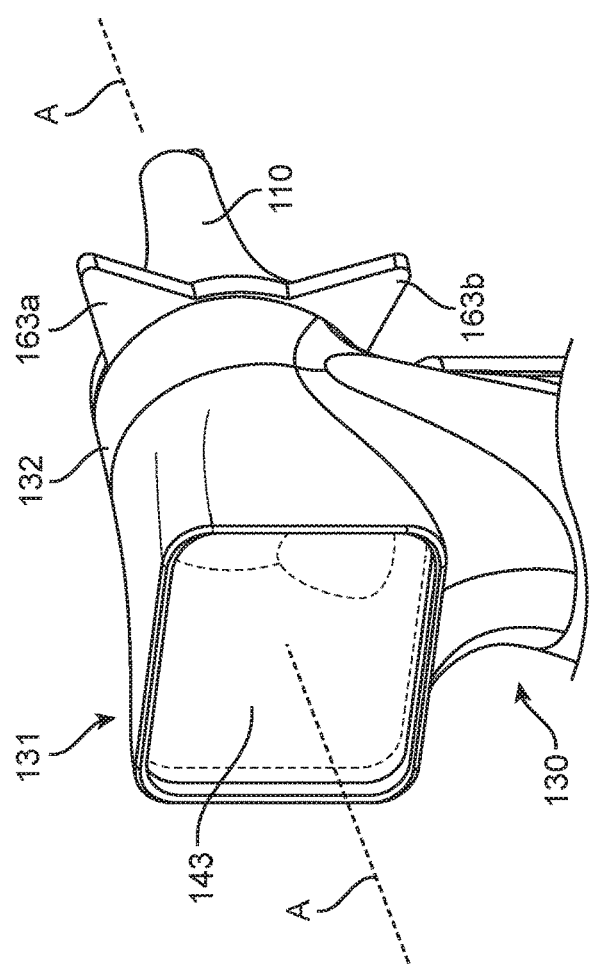
Figure 4N:
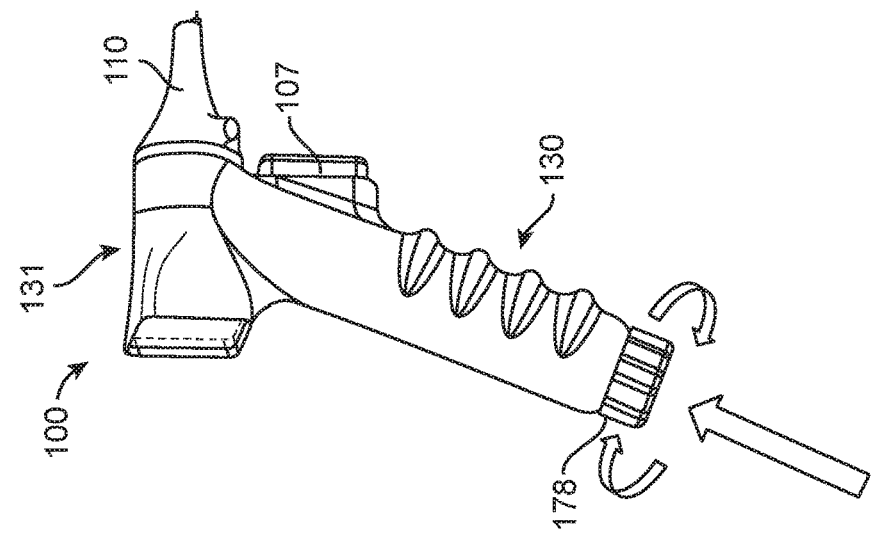
FIGS. 4L-4N are partially exploded views of another implementation of the device of FIG. 4A illustrating coupling of a reservoir cartridge.

The canal guide 110 can be attached to the housing such that the position of the guide lumen relative to the housing is adjustable by a user. The attachment between the canal guide 110 and the housing can be a rotatable attachment. In some implementations, the relative location the needle assembly 115 extends distal to the canal guide 110 around the longitudinal axis A of the canal guide 110 can be adjusted. FIGS. 4J-4K illustrate an implementation of the ear canal guide 110 that is configured to be rotated around the longitudinal axis A relative to the forward end 132 of the upper portion 131 of the housing 105. The lumen 140 through which the needle assembly 115 extends is eccentric or off-set from the longitudinal axis A of the canal guide 110 such that as the canal guide 110 is rotated, the position of the lumen 140 changes location around the axis A. This adjustment allows the user to select the most comfortable or convenient ergonomic positioning while still controlling the position of the needle assembly 115 relative to the central axis of the ear canal 40. The canal guide 110 and thus, the lumen 140 can be rotated around the longitudinal axis A in degree increments between 0 degrees and 360 degrees. A degree of rotation of the canal guide relative to the housing can be indicated to a user visually, audibly, and/or tactilely. In some implementations, the degree increment of rotation can be felt as a series of clicks between preset adjustments or observed by a user as a series of relative markings. In some implementations, the rotation of the canal guide 110 is fully customizable to achieve infinite degrees of rotation. The canal guide 110 can further include one or more markers 163 visible to a user during use that identifies the location of the lumen 140 as the canal guide 110 is rotated. The markers 163 can indicate relative anatomical locations for optimal targeting of the tympanic membrane 5, such as an upper marker 163a identifying where a patient's nose should be located relative to the device 100 and another marker 163b pointing towards where a patient's feet should be located relative to the device 100 (see FIG. 4J). Any of a variety of markers 163 can be incorporated.

The implementations of the devices described herein deliver drug solutions and/or drug suspensions, as well as powders, liquids, gels, dispersions, and aerosols contained within a reservoir 120 through the cannula 119 having a canal guide positioned within the tympanic cavity 30. At least a portion of the housing 105 can be configured to contain at least a portion of the reservoir 120 configured to contain a substance 122 to be delivered. The reservoir 120 can be integral with the housing 105 (see FIGS. 3A-3D) or the reservoir 120 can be a detachable element such as a cartridge 125 containing the reservoir 120 (see FIGS. 4L-4N). In some implementations, the housing 105 can include one or more windows 164 configured to reveal at least a portion of the reservoir 120 from outside the housing 105 such that a user can easily and quickly ascertain whether the device is primed for an injection (see FIGS. 3A-3D and FIG. 4A). The window 164 can be a transparent or semi-transparent feature extending through the housing 105.

Regardless the configuration, a proximal end of the flexible shaft or cannula 119 can include an inlet that is configured to be operatively and fluidly coupled to an outlet from the reservoir 120 and the distal end region of the cannula 119 can include an outlet that is configured to be positioned within the middle ear 30. The substance 122 from the reservoir 120 can be delivered through the cannula 119 to the patient, for example, by activation of an actuator 107.

The cartridge 125 can include a housing 175 having an inner chamber forming the reservoir 120 configured to store an amount of a substance 122 to be delivered by the device 100. The reservoir 120 can be a container surrounded or formed by a flexible material or bag that may be expandable and contained within the relatively rigid housing 175. The reservoir 120 may have any suitable shape and size configured for receiving the fluid substance, such as through a fill port. The reservoir volume can vary, for example, between about 50 ul and about 250 ul, or between about 75 ul and about 200 ul, or between about 100 ul and about 150 ul. The housing 175 of the cartridge 125 can be any of a variety of suitable materials, particularly moldable materials, including polymers and specific materials such as polycarbonate or the like. The flexible material contained by the housing 175 can also be any of a variety of suitable materials, such as polymers like PET, SiO, linear low density polyethylene or the like. The drug cartridge 125 can be manufactured as a pre-filled element or can be filled by a user at the time of use. In some implementations, the reservoir 120 is a separate syringe device configured to couple with the needle assembly 115, which in turn inserts through the canal guide 110 to perform the injection.

Figure 4M:
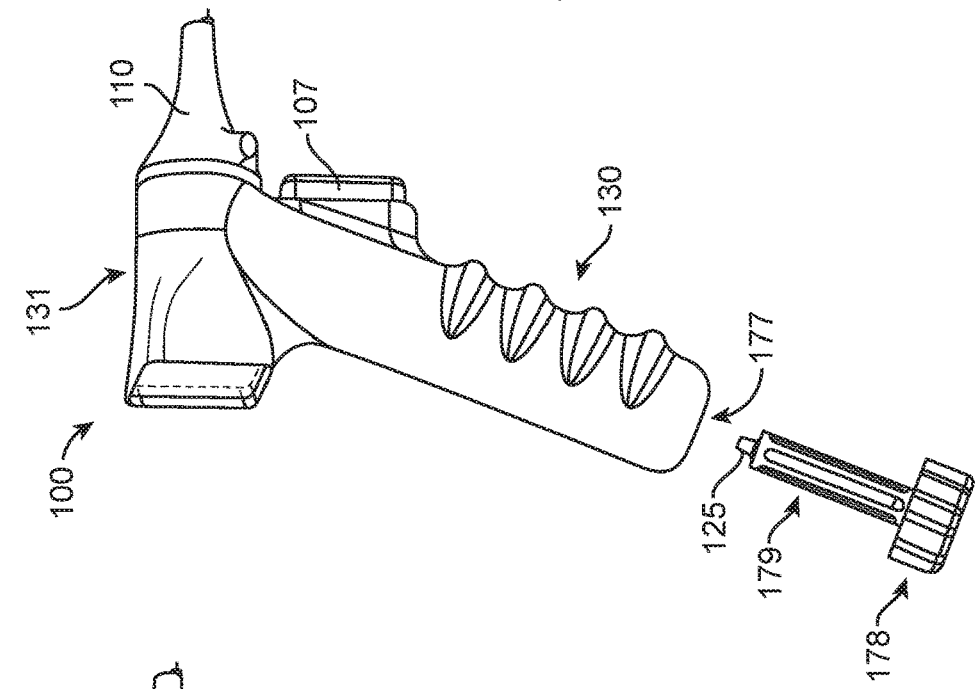
Figure 4L:
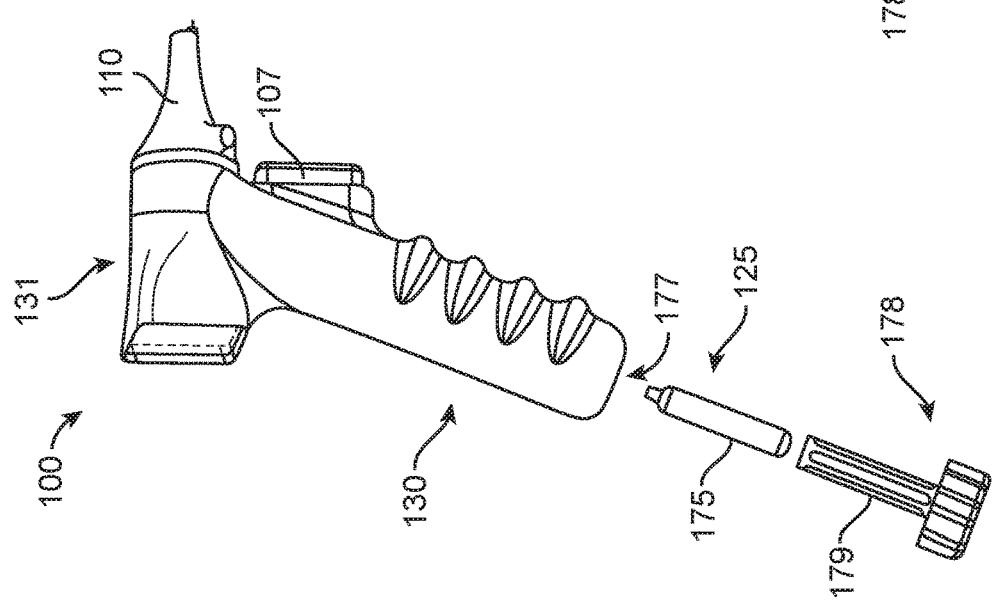

In some implementations, the housing 105 (such as the hand-held portion 130) can be at least partially hollow such that a cartridge 125 can be releasably and operatively secured within the housing 105 of the device 100 (see FIGS. 4L-4N). The housing 105 can include a receiving slot 177, for example, in a lower end region of the hand-held portion 130. The receiving slot 177 can be opened such as by unscrewing or otherwise decoupling a cap element 178. The cap element 178 can include an internal carrier 179 having an inner diameter configured to receive the outer diameter of the cartridge 125. A user can slide the cartridge 125 into the carrier 179 and replace the cap element 178 onto the lower end region of the housing 105 such that the internal carrier 179 inserts within the receiving slot 177. Upon coupling the cap element 178 with the housing 105, the cartridge 125 can be operably connected to the device 100 such that the substance 122 from the reservoir 120 can be delivered out the needle assembly 115 upon activation of the actuator 107.

The housing 175 of the cartridge 125 and/or the housing 105 of the device 100 can include one or more corresponding alignment or attachment mechanisms such that the cartridge 125 may be reversibly attached and detached from the housing 105 of the device 100. The alignment or attachment mechanisms can include a tap needle or similar element within the receiving slot 177 configured to penetrate a septum or other penetrable feature on an upper end of the cartridge 125 to place the reservoir 120 within the cartridge 125 in fluid communication with the proximal end of the inner cannula 119. The tap needle may penetrate the septum of the cartridge 125 upon installation and coupling the cartridge 125 with the housing 105.

The device 100 may include a pumping mechanism configured to urge the substance from the reservoir 120 into the cannula 119 for delivery to the patient upon activation of an actuator 107. The pumping mechanism can be a mechanical mechanism including the actuator 107, such as a piston plunger of a syringe shown in FIGS. 3A-3B. The pumping mechanism can also be an electrically powered pumping mechanism including a positive displacement pump configured to be driven by any of a variety of drive mechanisms including hydraulic, pneumatic, piezoelectric, stepper motor, continuous motor, or the like configured to urge fluid out of the reservoir 120. In an implementation, the pumping mechanism is a spring-driven plunger without any active electronics to cause the pumping to occur. In this implementation, the pumping mechanism is a single-use or limited-use pump suitable for a disposable injector device.

Figure 16:
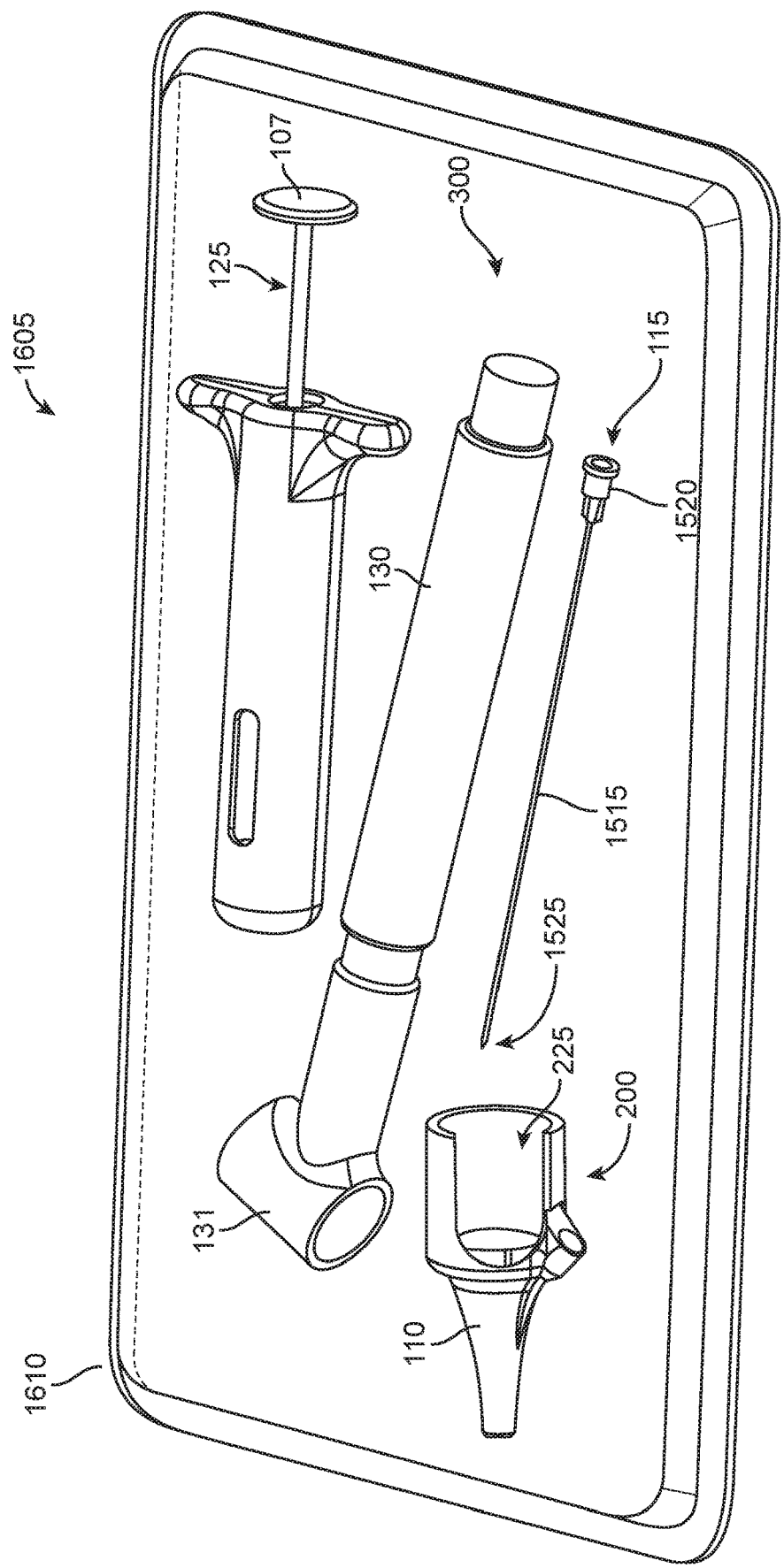
FIG. 16 illustrates a kit including the device of FIGS. 15A-15C.
Figure 17:
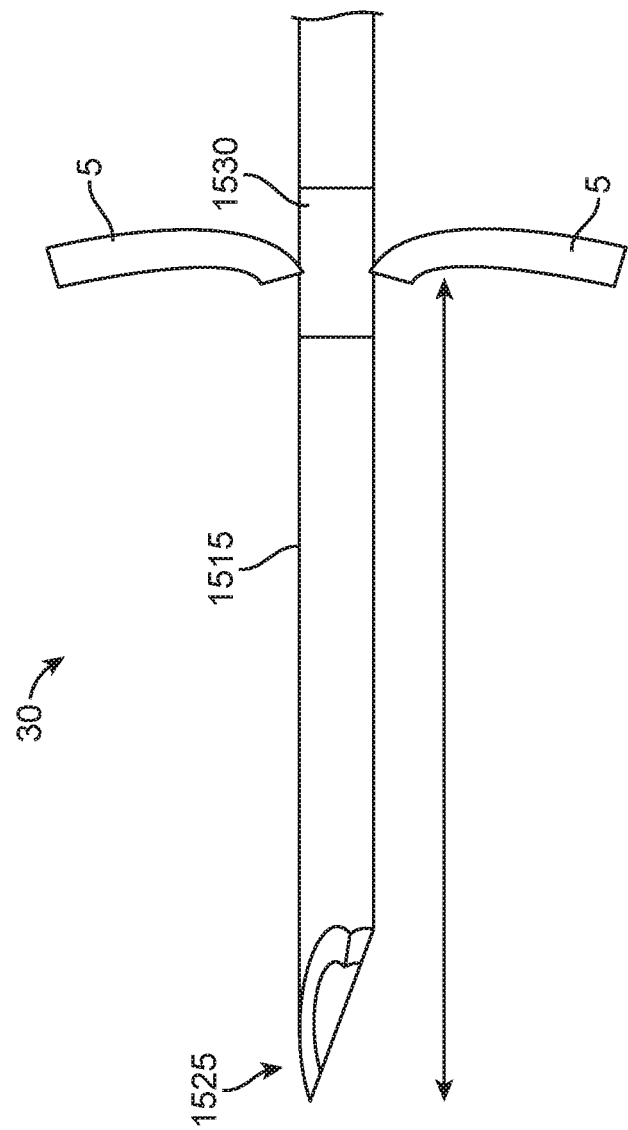
FIG. 17 illustrates an implementation of a flexible needle for use with the device of FIGS. 15A-15C.

In some implementations, the entire device 100 is disposable and thrown away after a single use, similar to how a syringe may be used. In other implementations, the entire device 100 is reusable and configured to be autoclaved or sterilized. In some implementations, certain components of the device 100 are durable and reused after use whereas other components are configured to be removed from the durable portion after use and disposed. For example, one or more of the cartridge 125, the needle assembly 115 including the shaft 117 and cannula 119, and the canal guide 110 can be removed from the housing 105 and disposed of after use. Each of the various components can be manufactured such that they are sterile. One or more of the components can be manufactured in a sterile package as a kit. FIG. 16 shows an implementation of a kit 1605 including a sterile packaging 1610 containing an otoscope-type viewing element 300 that is configured to couple with a positioning guide 200 having a speculum-like canal guide 110, a needle assembly 115 configured to insert through the canal guide 110 and configured to couple with a reservoir cartridge 125, such as a pre-filled syringe.

Figure 5C:
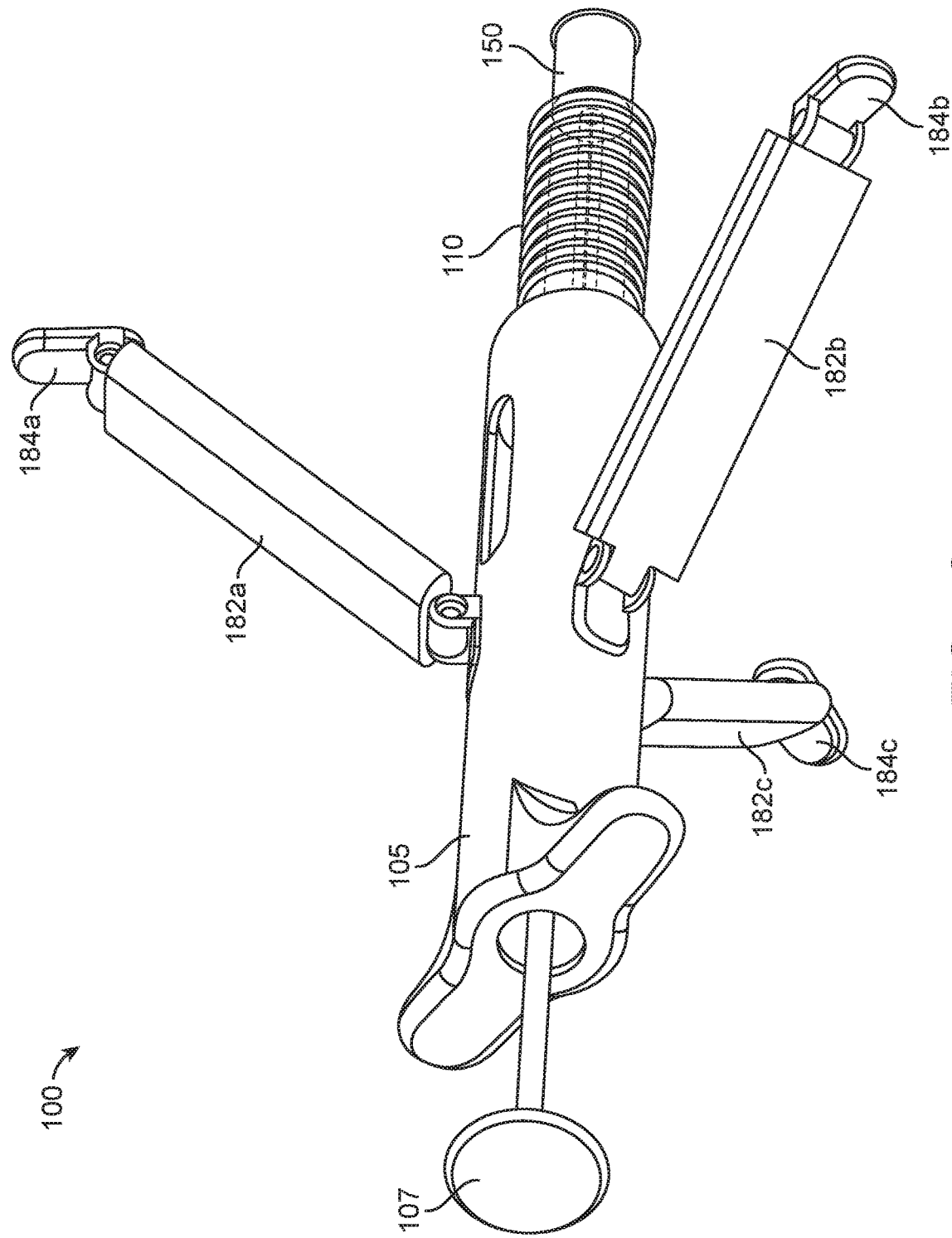

FIGS. 5A-5C show an implementation of an optional stabilization feature that can provide support and assist in alignment of the needle assembly 115 with the tympanic membrane 5 to further reduce the risk of middle ear damage due to unintended needle motion. The device 100 can include one or more collapsible external support legs 182 coupled to a region of the housing 105. In an implementation, three collapsible legs 182 can be coupled to a region of the housing 105 such that upon extension they form a tri-pod of stabilization relative to the ear canal guide 110. The legs 182 can be arranged symmetrically around the longitudinal axis A of the device 100. The legs 182 can each extend outward by an angle θ relative to the axis A. The angle θ and also the length of the legs 182 in the extended configuration can allow for placement of the legs 182 against a patient. For example, a first leg 182a can be positioned anteriorly on a patient's jaw, a second leg 182b can be positioned caudally on a patient's skull near the neck, and the third leg 182c can be positioned more cephalad on a patient's skull near the crown. Each leg 182 can incorporate a foot member 184 movably coupled to a distal end of the leg 182 and configured to fold outward when the legs 182 are in an extended configuration (FIG. 5B-5C) and fold inward when the legs 182 are in a collapsed configuration (FIG. 5A). The legs 182 can snap into the expanded configuration such that they avoid inadvertent collapse. The degree of extension of each leg 182 can be selectable between a plurality of pre-set angles relative to the longitudinal axis A. Each foot member 184 can swivel around its attachment with the leg 182 between the inward and outward folded configurations to provide a tailored fit with the patient to provide better stabilization. In some implementations, the foot member 184 is coupled to its leg 182 by a barrel hinge type coupling having at least 2 degrees of freedom. In other implementations, the foot member 182 is coupled to its leg 182 by a ball and socket type coupling providing any degree of freedom.

Figure 6:
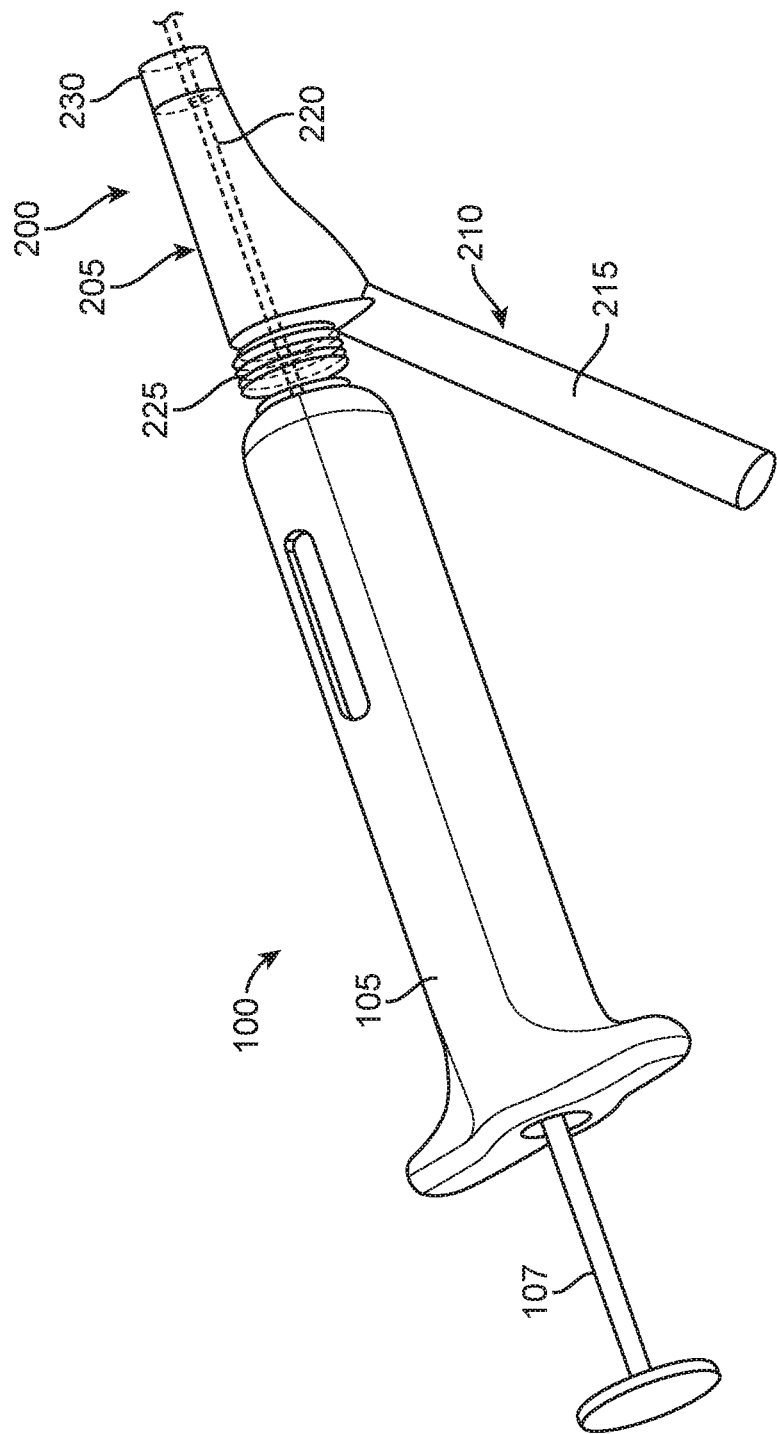
FIG. 6 is a perspective view of the device of FIG. 3C coupled to a positioning guide.

FIG. 6 shows another implementation of an optional stabilization feature configured to provide additional stabilization of the device during an injection reducing the risk of middle ear damage due to unintended needle motion. The device 100 can be removably coupled to a positioning guide 200. The positioning guide 200 can include a forward end 205 configured to couple with the device 100 and a rear end 210. The rear end 210 can be held by a user during an injection, such as by a handle 215. The forward end 205 of the positioning guide 200 can include a bore 220 extending between a receiving portion 225 of the forward end 205 and a distal-most end 230 of the forward end 205. The receiving portion 225 is configured to receive and mate with the canal guide 110 of the device 100. Upon coupling the canal guide 110 and the receiving portion 225, the bore 220 of the positioning guide 200 aligns with the location where the needle assembly 115 extends out from the canal guide 110. The device 100 and the positioning guide 200 can be coupled together while the needle assembly 115 is in a retracted configuration. The device 100 having the positioning guide 200 coupled to its distal end can be inserted through the ear canal 40 while the needle assembly 115 remains retracted. Once positioned, the device 100 can be actuated to cause the needle assembly 115 to extend out the ear canal guide 110 and through the bore 220 of the positioning guide 200 until a distal-most end of the needle assembly 115 extends past the distal-most end 230 of the positioning guide 200 and penetrates through the tympanic membrane 5. In other implementations, the positioning guide 200 can be positioned within the ear canal 40 without the device 100 coupled to it. For example, the forward end 205 of the positioning guide 200 can be inserted within the ear canal 40 and the bore 220 arranged relative to the tympanic membrane 5 such that the quadrant to be pierced is targeted. Upon aligning the positioning guide 200 within the ear canal 40, the distal-most end 230 of the forward end 205 of the positioning guide 200 is positioned adjacent the tympanic membrane 5 and the receiving portion 225 of the positioning guide 200 remains external to the ear. A user can insert the needle assembly 115 through the receiving portion 225 into the bore 220 of the positioning guide 200 until the distal-most end of the needle assembly 115 extends past the distal-most end 230 of the forward end 205 of the positioning guide 200 and through the tympanic membrane 5 (see FIG. 6). The user can also insert the canal guide 110 through the receiving portion 225 while the needle assembly 115 remains retracted. Once the canal guide 110 and the receiving portion 225 are properly arranged and coupled together, the user can actuate the device 100 to extend the needle assembly 115 through the canal guide 110 and through the bore 220 of the positioning element 200. The guide 200 can be pre-positioned in the ear and an already-extended needle inserted through it to perform an injection. The guide 200 can also be pre-positioned in the ear and the device inserted into the proximal end of the guide 200 while the needle is in a retracted position. Once the guide 200 and the device 100 are properly aligned with one another, the needle can then be extended to perform the injection. It should be appreciated that although the needle assembly 115 need not be movable and can be in a fixed position relative to the housing 105. The guide 200 can provide protection to the ear canal when used with a fixed needle assembly 115.

Figure 7A:
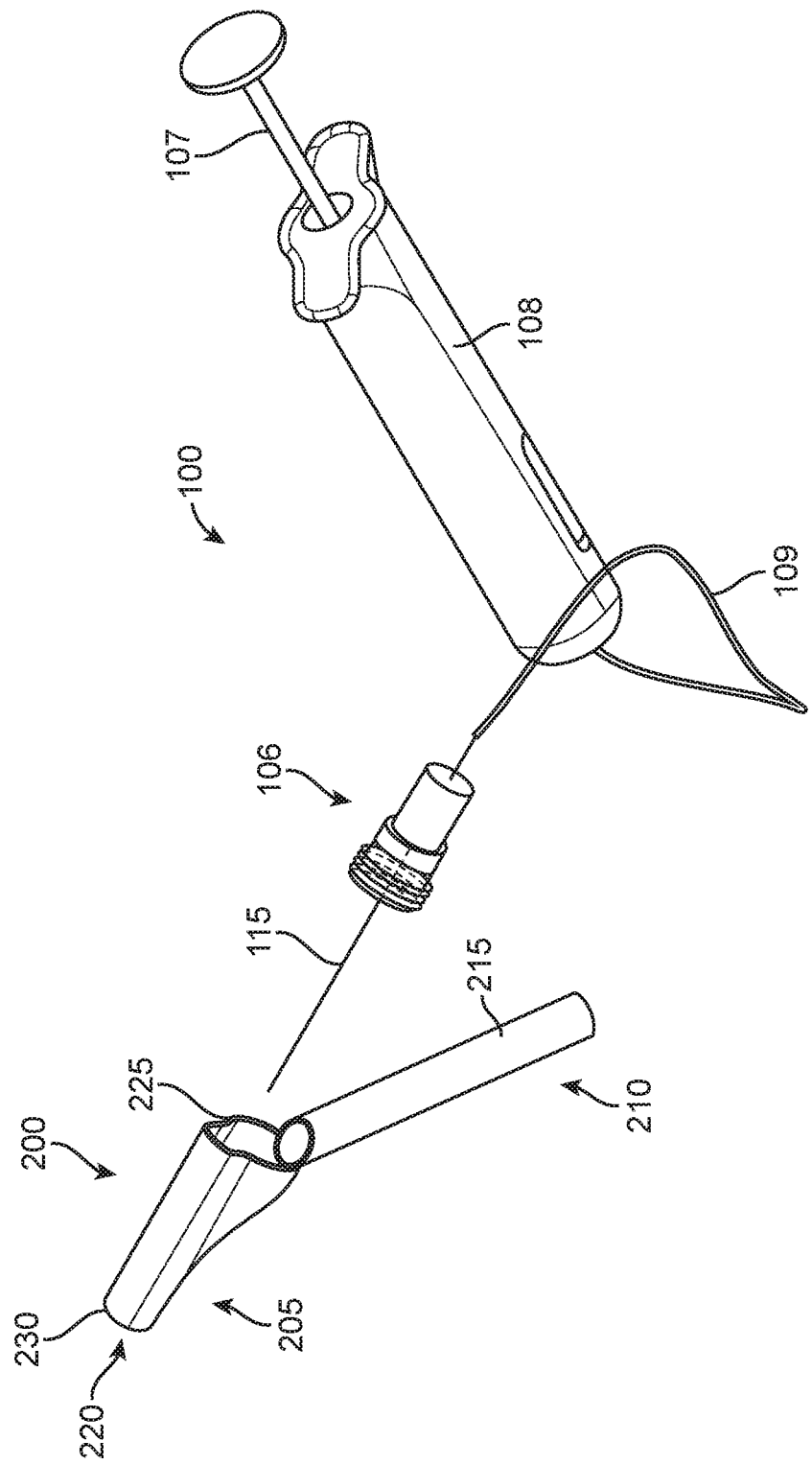
FIGS. 7A-7B are perspective views of an implementation of the device of FIG. 3A having a floating delivery head relative to a positioning guide.
Figure 7B:
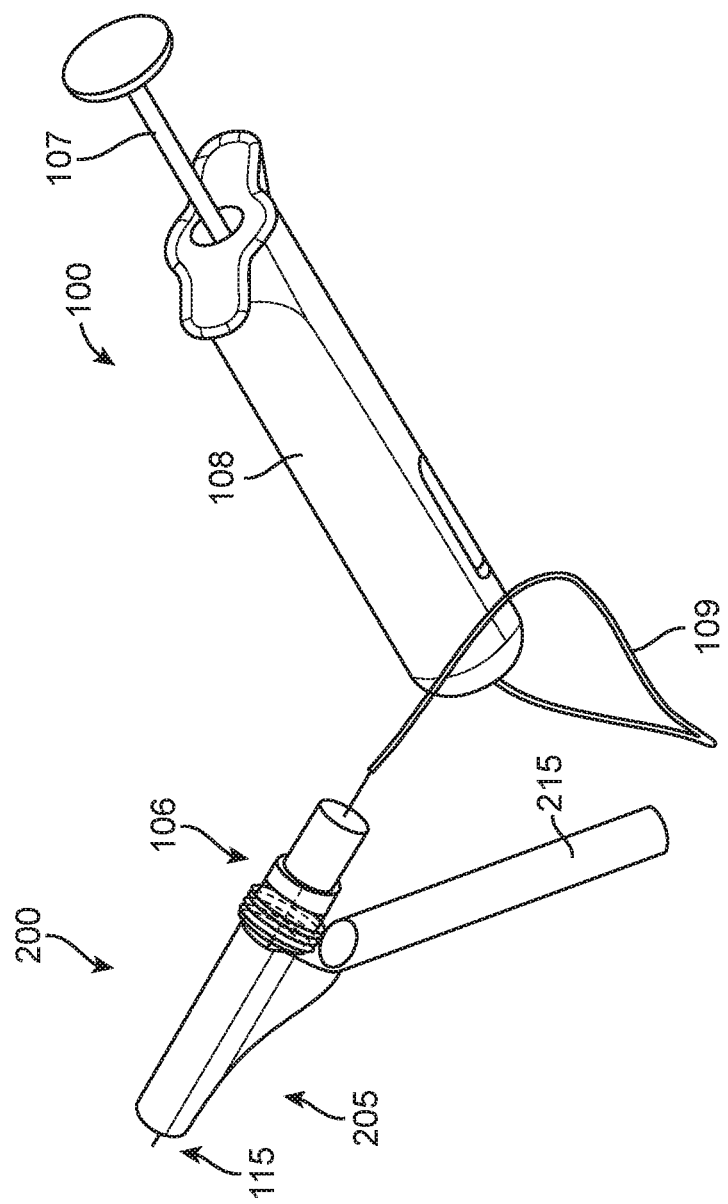

FIGS. 7A-7B show an implementation of the device 100 in which the housing 105 includes a floating delivery head 106 coupled to a proximal body 108 via a flexible cannula 109. The floating delivery head 106 can provide for increased positioning control and stabilization and reduces the risk of unintended motion transfer from the proximal body 108. The needle assembly 115 and the canal guide 110 can be part of the floating delivery head 106. A user can position the delivery head 106 within the ear canal 40 separately without moving or even holding the proximal body 108. A positioning guide 200 can optionally be used to insert the delivery head 106 into place within the ear canal 40 as described in more detail above.

Figure 8:
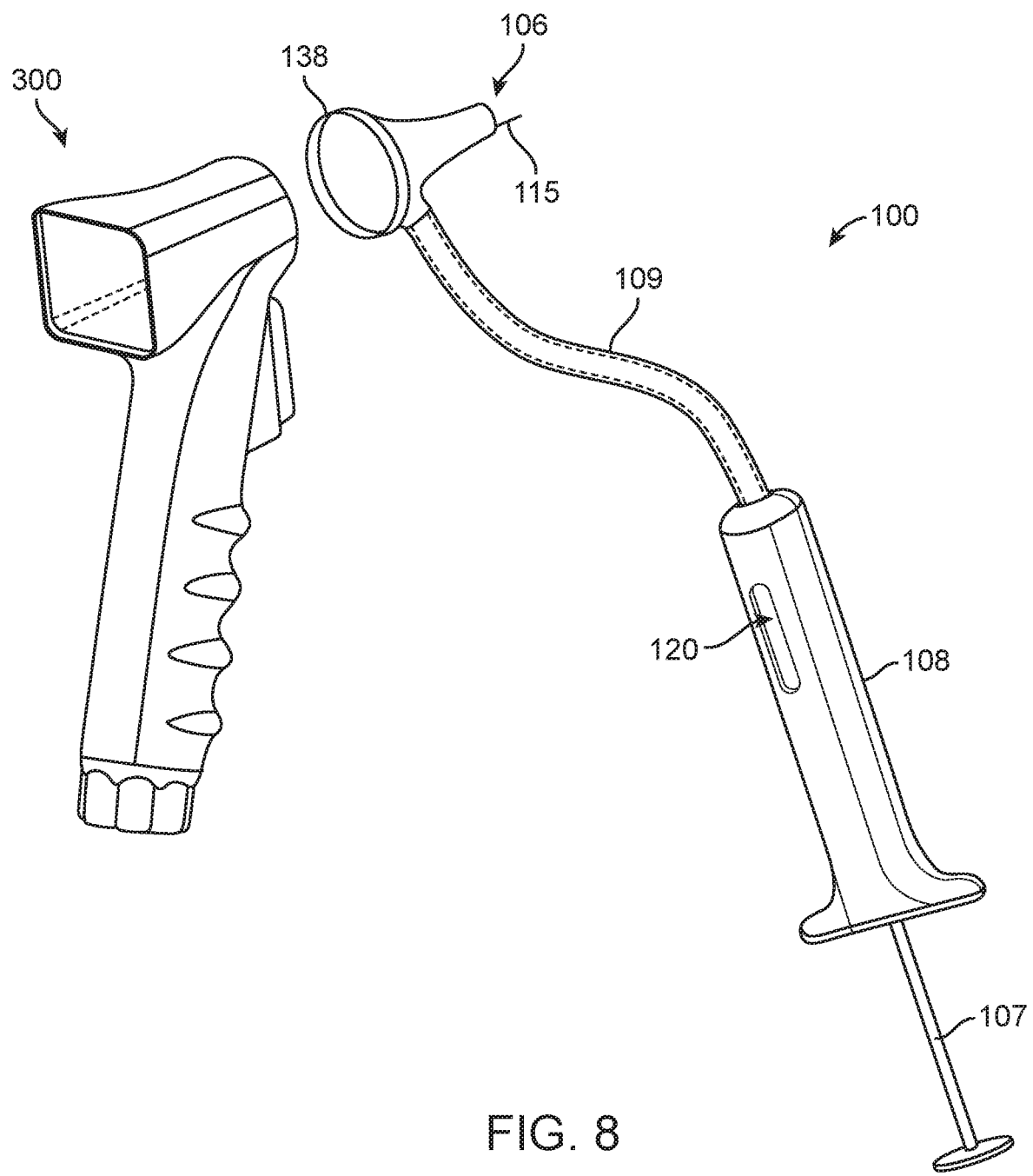
FIG. 8 is a perspective view of an implementation of a device having a floating delivery head configured to couple with an otoscope handle.

In some implementations, the floating delivery head 106 can include the needle assembly 115 and the ear canal guide 110 (see FIG. 8). The reservoir 120 in this implementation can be contained within a syringe-type cartridge proximal body 108 coupled to the floating delivery head 106 via the flexible cannula 109. The proximal body 108 can be configured to inject the substance to the patient from the reservoir 120 through the flexible cannula 109 coupled to the needle assembly 115 extendable from the canal guide 110. The proximal end 138 of the canal guide 110 can be coupled to an otoscope handle 300 for positioning and guidance. Thus, the device 100 can incorporate a drug delivery syringe having a plunger-driven or spring-loaded injection mechanism connected directly to the ear canal guide 110 and needle assembly 115 and an otoscope type viewing element 300. This implementation separates the otoscope viewing from the delivery syringe to reduce the risk of unwanted motion due to delivery activation from being inadvertently transferred to the trans-tympanic elements and membrane damage.

In addition to the stabilization features described above, the devices described herein can incorporate one or more features that aid in the visualization, aiming, and targeting of the needle assembly 115 to prevent inadvertent penetrations and damage to delicate structures in the ear during an injection. As discussed above and as shown in FIG. 8, the canal guide 110 having the needle assembly 115 extending therethrough and fluidly coupled to a reservoir 120 can be configured to couple to a separate otoscope type viewing element 300. Alternatively, the device 100 itself can have an otoscope type form factor and incorporate one or more visualization features typical of otoscopes. Again with respect to FIG. 4A, the forward end 132 of the upper portion 131 can be coupled to the canal guide 110 configured to be inserted within the ear canal similar to speculum tips. The rear end 133 of the upper portion 131 can incorporate a viewing lens 143 similar to an otoscope lens for the user to view the target region for injection. The first lumen 140 through the canal guide 110 can be eccentric to or off-set from the longitudinal axis A of the canal guide 110 such that the user may view an object through the second lumen 142 using the lens 143. For example, the user can see the tympanic membrane 5 through the second lumen 142 before, during, and/or after advancing the needle assembly 115 through the first lumen 140. The visualization features can improve the safety of the device by allowing the user to view the tympanic membrane 5 while the needle assembly 115 is advanced toward the membrane. Endoscope, video visualization device, and other viewing elements can also be used with the device. The device can also incorporate one or more illumination elements, such as a LEDs, lenses, light pipes, filters, etc. that improve the visibility through the device during use.

FIGS. 15A-15C illustrate another implementation of a device 100 having an otoscope type viewing element 300 configured to couple with a positioning guide 200. The viewing element 300 can include a hand-held portion 130 and an upper portion 131. The positioning guide 200 can include proximal receiving portion 225 configured to engage with the upper portion 131 of the viewing element 300 and a canal guide 110 configured to be inserted within the ear canal similar to speculum tips. The canal guide 110 of the positioning guide 200 can include a viewing lumen 142 and a guide lumen 140, which in the implementation of FIGS. 15A-15C is a single flexible needle shaft. The needle assembly 115 can be inserted into the guide lumen 140 via a proximal opening 1505 into the lumen 140 on the positioning guide 200. The guide lumen 140 can extend from the proximal opening 1505 to a distal opening 1510 at the distal-most end 136 of the canal guide 110. The guide lumen 140 can have a curved shape that corresponds to the slope of the outer wall of the canal guide 110. The proximal opening 1505 can have a receiving inlet that is enlarged relative to the inner diameter of the guide lumen 140 to aid in the insertion of the needle assembly 115 into the guide lumen 140 (see FIG. 19F). The inner diameter of the guide lumen 140 can be sufficient to receive the outer diameter of the needle assembly 115. Thus, the guide lumen 140 can have an inner diameter that is between about 0.4 mm to about 1.0 mm The viewing lumen 142, in contrast, can be significantly larger in inner diameter.

As mentioned, the guide lumen 140 can extend between the proximal opening 1505 to a distal opening 1510 that curves along a sloped wall of the canal guide 110. The guide lumen 140 can be eccentric to or off-set from the longitudinal axis A of the canal guide 110 such that the user may view an object through a viewing lumen 142 using the lens 143. Thus, the distal opening 1510 from the guide lumen 140 can be arranged to one side of the distal opening from the viewing lumen 142. The rear end 133 of the upper portion 131 can include a viewing lens 143 to allow a user to view the target region for injection through the viewing lumen 142 of the positioning guide 200. Following positioning of the canal guide 110 within the ear canal, the needle assembly 115 can be inserted through the guide lumen 140 until it extends past the distal-most end 136 of the canal guide 110 as described elsewhere herein. The canal guide 110 can have a tapered, sloped shape wherein a proximal outer diameter of the canal guide 110 is larger than a distal outer diameter. The guide lumen 140 can extend along a curved wall of the canal guide 110 between the proximal opening 1505 and the distal opening 1510. The distal opening 1510 from the guide lumen 140 can be positioned eccentric to or off-set from a longitudinal axis A of the canal guide 110. The curve of the guide lumen 140 can be from a first axis to a second axis. The first axis can extend through the proximal opening 1505 into the guide lumen 140 and the second axis extends through the distal opening 1510 from the guide lumen. The first axis can be arranged at an angle relative to the second axis and/or the longitudinal axis A of the canal guide 110. The second axis can be parallel (and eccentric) to the longitudinal axis A. The angle between the first axis to the second axis can be greater than 0 degrees, but less than 90 degrees. Thus, the first axis is preferably not parallel to the second axis and preferably not perpendicular to the second axis. In some implementations, the angle between the first axis and the second axis is about 5-85 degrees, about 10-80 degrees, about 15-75 degrees, about 20-70 degrees, about 25-65 degrees, including about 45 degrees. The guide lumen of any of the embodiments described herein can be curved as well. For example, the lumen 140 and the lumen 152 of the contact tip 150 shown in FIG. 3C-3F need not be straight and can curve from a first axis to a second axis at an angle to the first axis as described above.

The guide lumen 140 can have an inner diameter suitable to receive the outer diameter of the needle assemblies described herein. In some implementations, the needle assemblies include a small gauge needle shaft having a gauge between about 30 g to about 33 g. The guide lumen 140, in turn, can have an inner diameter that is at least as large as the small gauge needle (e.g., at least 0.22 mm). The guide lumen 140 can have an inner diameter that is between about 0.170 mm up to about 1.00 mm, or between 0.22 mm to about 0.65 mm. Some needle assemblies described herein include a larger bore portion more proximally. The large bore portion may be 20 g to 25 g. Thus, the lumen 140 can have an inner diameter that is at least as large to receive the larger pore portion (e.g., up to about 0.95 mm). The inner diameter of the guide lumen 140 need not be uniform and can vary along its length. In some implementations, the guide lumen 140 can have a distal end region near the distal opening 1510 that has a smaller inner diameter sized to receive smaller gauge shafts (e.g. 30 g-33 g) and a proximal end region near the proximal opening 1505 that has a larger inner diameter to receive large gauge shafts (e.g., 20 g-25 g). The decrease in inner diameter of the guide lumen 140 near the distal opening 1510 can aid in preventing over-insertion of a shaft through the guide lumen 140.

The proximal opening 1505 can be positioned relative to the canal guide 110 in a location that allows for ease of entry of the needle assembly 115 into the guide lumen 140. In some implementations, such as shown in FIG. 15A, the proximal opening into the guide lumen 140 is available on one side of the canal guide 110. From a user's perspective, looking through the viewing lens 143 at a proximal end of the canal guide 110, the proximal opening 1505 to the guide lumen 140 can be located between about 3 o'clock to about 5 o'clock on a first side of the viewing lens 143 or between about 7 o'clock to about 9 o'clock. In other implementations, for example the implementation shown in FIGS. 19A-19D, the proximal opening 1505 into the guide lumen 140 can be located at about 6 o'clock or a lower side of the canal guide 110 between the gripping features 127 on either side of the viewing lens 143. The above are examples of more ergonomically comfortable configurations. Any of a variety of configurations are considered herein.

The positioning guide 200 can be removed from the upper portion 131 of the viewing element 300. A receiving portion 225 of the positioning guide 200 can be substantially C-shaped in cross-section in order to slide onto the upper portion 131 or snap over the upper portion 131 such that the central axis of the guide lumen 140 substantially aligns with the viewing lens 143. Any of a variety of coupling mechanisms are considered herein.

Figure 18:
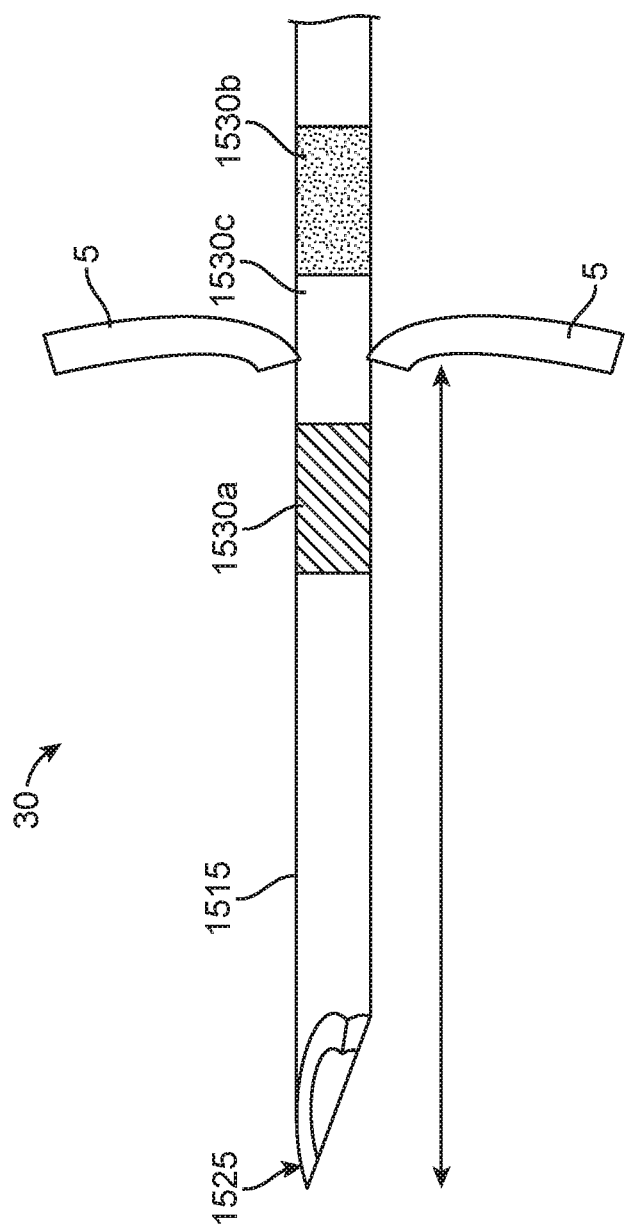
FIG. 18 illustrates another implementation of a flexible needle for use with the device of FIGS. 15A-15C.
Figure 19A:
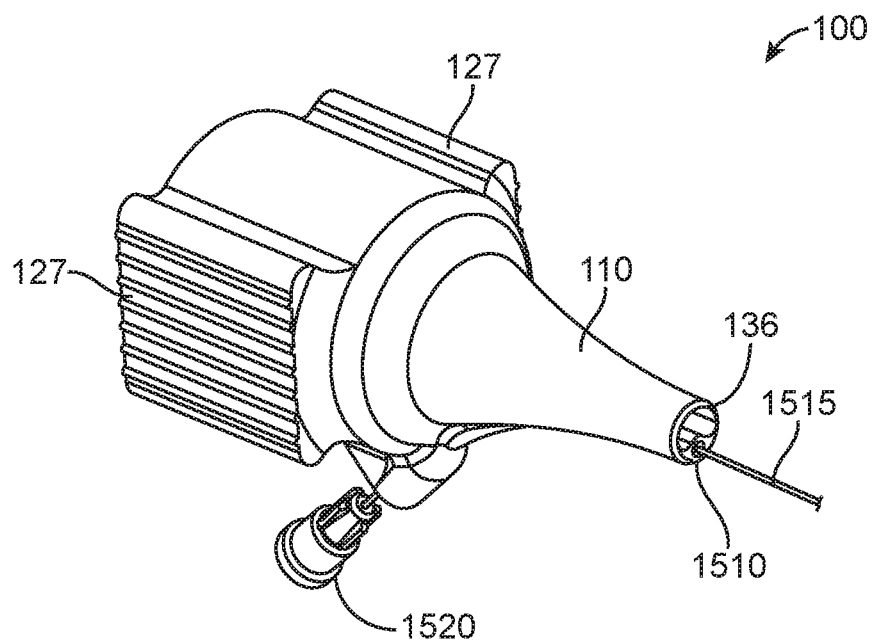
FIGS. 19A-19F are views of another implementation of a device configured to perform intratympanic injections.
Figure 19B:
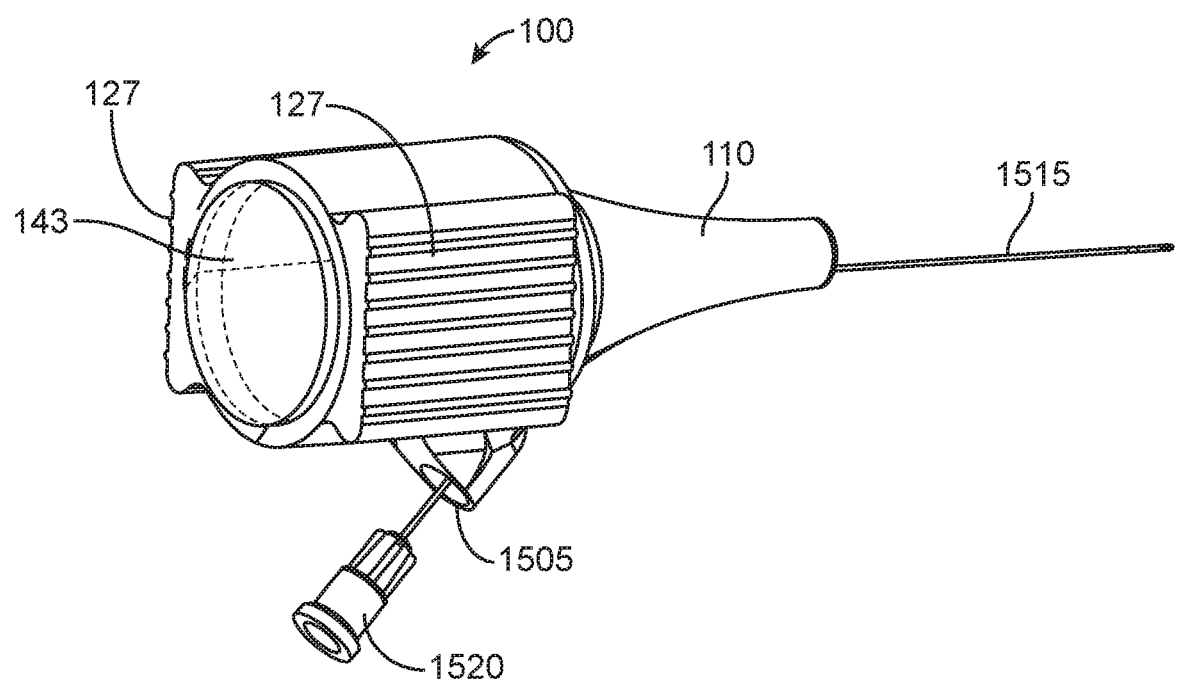
Figure 19D:
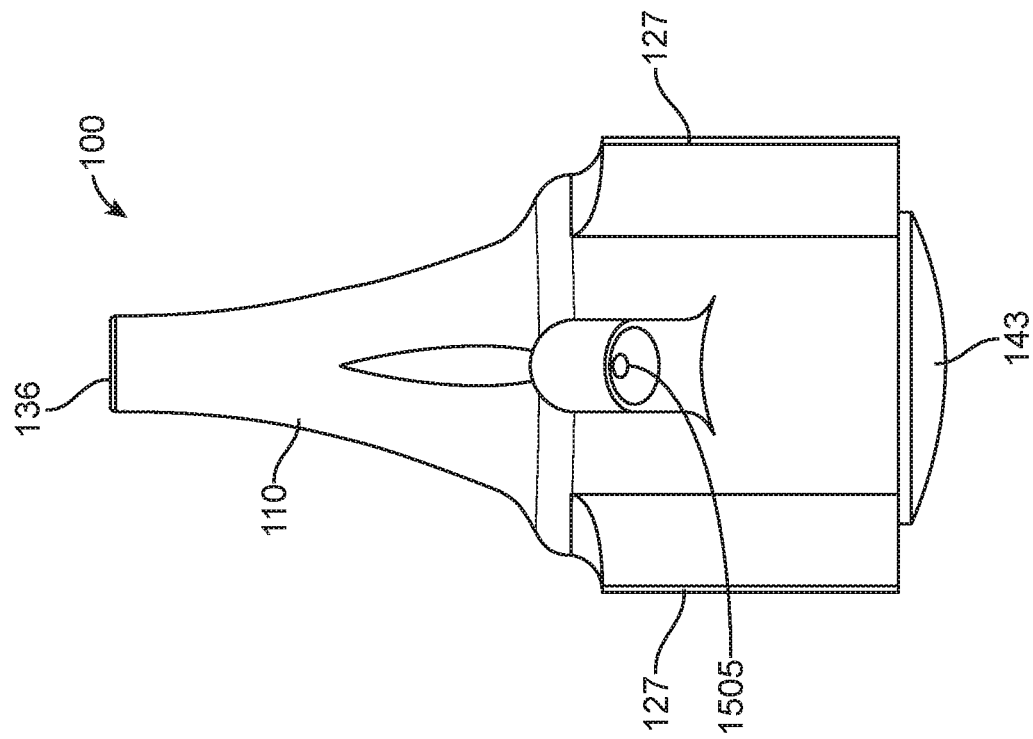
Figure 19C:
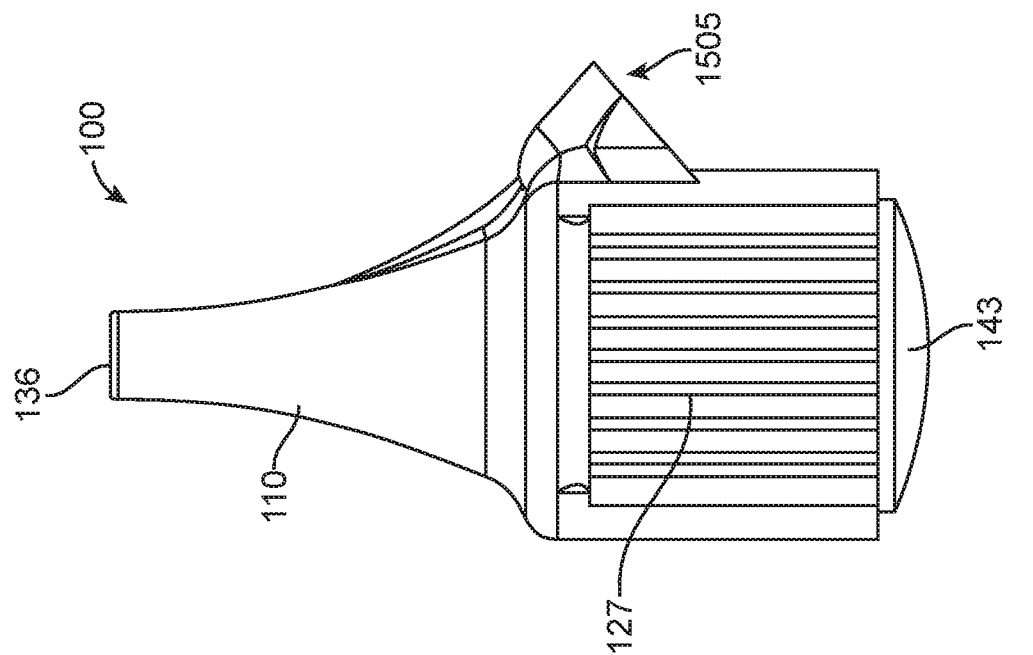
Figure 19E:
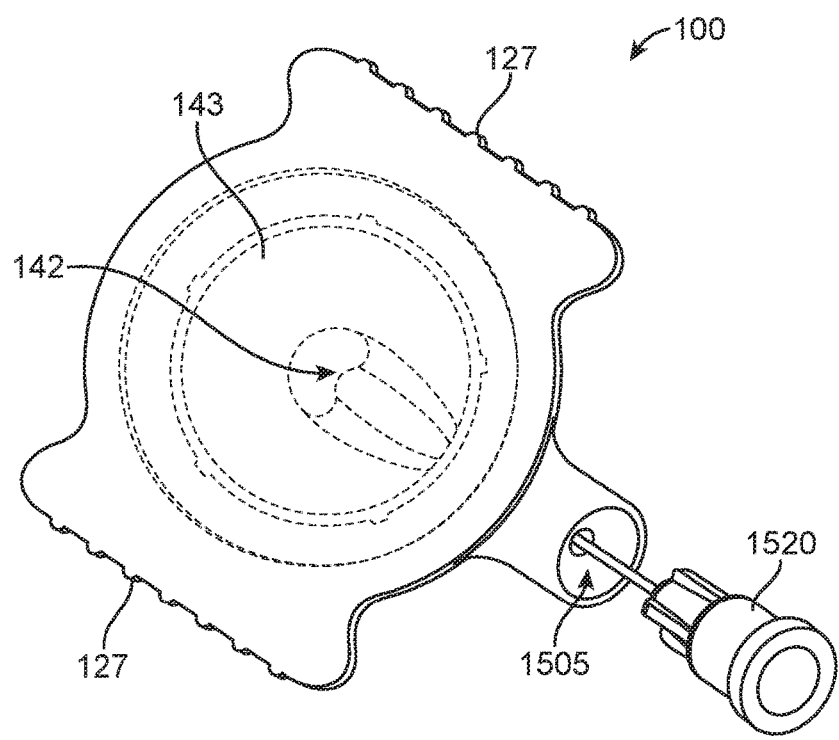
Figure 19F:
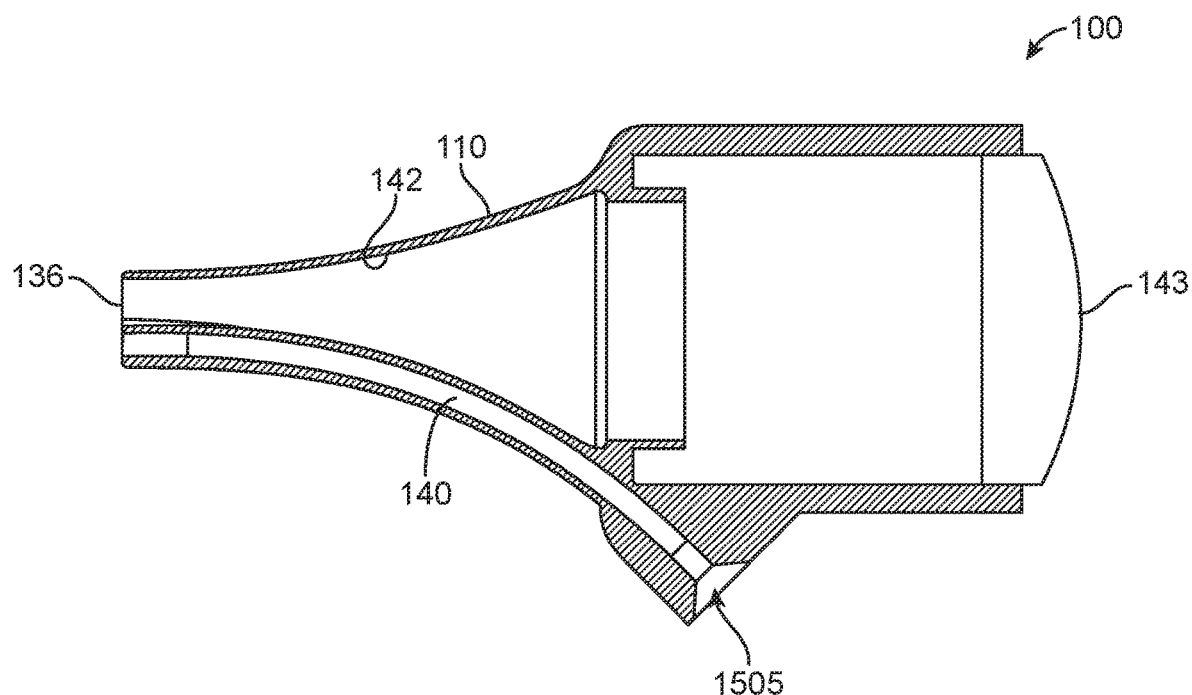

The needle assembly 115 can include a needle 1515 having a proximal coupler 1520 and a distal sharp tip 1525. The shape of tip 1525 can vary as is known for needle bevels. The shaft of the needle 1515 can be flexible such that upon insertion of the flexible shaft or cannula through the first lumen 140 the needle 1515 can curve along with the path of the guiding lumen 140 (see FIGS. 15A-15C). The needle 1515 can include a visual marker 1530 on its outer surface located a distance proximal to the tip 1525. The marker 1530 can be visualized during use (i.e. through the second lumen 142) to ensure the proper insertion depth of the shaft of the needle 1515 is achieved. For example, a user can align the marker 1530 with the tympanic membrane 5 (see FIG. 17) to ensure the proper depth of penetration (arrow) is achieved. It is preferred that the tip 1525 of the needle 1515 reaches a location within the middle ear that is near, but not touching the medial wall of the cavity 30. The marker 1530 can be positioned on the shaft of the needle 1515 to achieve this optimal distance. FIG. 18 illustrates a further implementation of the needle 1515 having a plurality of visual markers 1530. The plurality of visual markers 1530 can include a first marker 1530a positioned distal to a second marker 1530b. The plurality of markers 1530 can be unique to one another such that they are distinguishable to a user. The markers 1530 can be distinguishable colors (e.g. red, yellow, green, etc.) or can be distinguishable in number or shape (e.g. rectangular bands, scalloped bands, triangular bands, etc.). In an implementation, the distal marker 1530a is red and indicates the portion of the needle that must be fully inserted into the tympanic cavity 30. The proximal marker 1530b is green and indicates the portion of the needle that must remain fully visible within the ear canal and proximal to the tympanic membrane 5. The first marker 1530a and second marker 1530b can be separated a distance from one another such that the tympanic membrane 5 is aligned with this portion of the needle shaft between the markers, which can form a third marker 1530c. The first marker 1530a can indicate the portion of the needle shaft that must be fully inserted past the tympanic membrane 5 and the second marker 1530b can indicate the portion of the needle shaft that must not be inserted past the tympanic membrane 5 and remain visible to the user. The relative alignment of the markers 1530 with the tympanic membrane 5 can ensure the user achieves the optimal depth into the tympanic cavity 30. The markers 1530 on the needle shaft can provide a graduated surface visible to the user that directly meters the insertion of the needle shaft through the tympanic cavity 30.

FIG. 16 illustrates an implementation of a kit 1605 having sterile packaging 1610 containing the viewing element 300, the positioning guide 200 having the canal guide 110, the needle assembly 115, and a reservoir cartridge 125. In this implementation, the reservoir cartridge 125 is a syringe body (e.g. pre-filled with therapeutic or empty and configured to be primed with therapeutic agent) having a plunger-type actuator 107. The needle assembly 115 can include the needle 1515 having one or more visual markers 1530, a proximal coupler 1520, and a sharpened tip 1525.

FIGS. 19A-19F illustrate another implementation of a device 100 for performing an intratympanic injection that need not include a traditional pistol-grip type handle portion. In this implementation, the device 100 is generally tubular and designed to be held between a thumb and forefinger of a single hand. A pair of gripping features 127 can be positioned on opposing sides of the device 100. The device 100 can include an integrated viewing lens 143 on a proximal end and a speculum shaped canal guide 110 on a forward end. As with the implementation of FIGS. 15A-15C, the canal guide 110 can include a guide lumen 140 and a viewing lumen 140. The guide lumen 140 can extend along a curve of the canal guide 110 from a proximal opening 1505 to a distal opening 1510 and is configured to receive the needle assembly 115. The guide lumen 140 can be eccentric to or off-set from an axis of the viewing lumen 142 such that a user can visualize the injection through the viewing lumen 142 using the viewing lens 143.

Figure 20A:
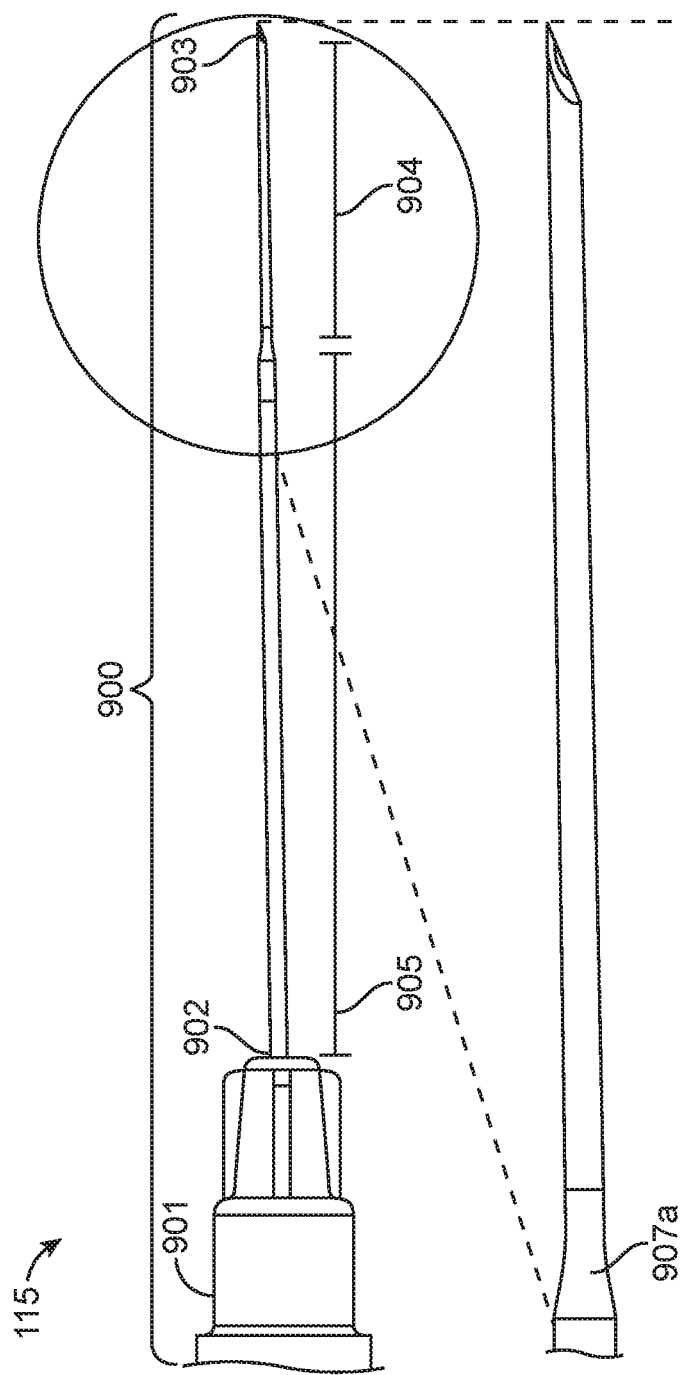
Figure 20B:
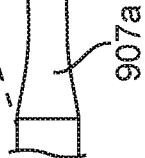

FIG. 20A shows a side view of an implementation of a needle assembly 115 including a single lumen tapered needle 900 with a standard luer connector 901 for intratympanic injection. The needle assemblies described herein can be long enough and flexible enough depending on the gauge to be inserted through the curved guide lumen 140 described above and shown in FIG. 19F. In an implementation, the needle assembly 115 can include a needle 900 that is 25 gauge and has a length of up to about 13.0 cm. The needle 900 includes a longitudinally extending cylindrical shaft 921a (FIG. 20C) that has a smooth outer surface diameter, a distal end, a proximal end, and an inner surface diameter defining a fluid lumen 906a, 906b, a portion of the shaft being symmetrically tapered about the longitudinal axis of the shaft at a collar region 907a, the collar region 907a having a gradually decreasing outer surface diameter and a gradually decreasing inner surface diameter toward the distal end (FIG. 20D). The total needle length can be approximately 3.5-4.0 cm long as measured from the distal penetrating tip 903 to the attachment point at the luer connection point 902. The luer connection 901 can, in turn, attach to a number of standard syringes (FIG. 24), modified syringes (FIGS. 3A-3G, 5A-5C), modified otoscopes (FIGS. 4A-4N), or other such devices. In some implementations, the total length allows the needle 900 to travel down the ear canal 40 (for example, through the guide lumen 140 of the canal guide 110) and pierce the tympanic membrane 5 (FIG. 1). The large bore section 905 can be about 1 inch (i.e. 2.5 cm) long and can be between a 20-25 gauge needle to reduce flow restriction for faster injection into the middle ear. The diameter of the needle can be reduced (i.e. symmetrically tapered) at collar region 907a of the needle. The trans-tympanic section 904 can be located distal to collar region 907a (between the penetrating tip 903 and the collar region 907a) and can measure about 0.5 inches (i.e. 1.25 cm) long. The trans-tympanic section can have a reduced diameter (i.e. 30-33 gauge) relative to the large bore section 905 to create a smaller hole through the tympanic membrane. The large bore section can symmetrically taper at the collar region to the flexible trans-tympanic section 904. The trans-tympanic section 904 can be flexible to prevent motion transfer to the tympanic membrane upon penetration of the tympanic membrane by the needle assembly. This minimizes trauma to the tympanic membrane, reduces tympanic scarring, and facilitates healing. The configuration of the trans-tympanic section makes it more flexible and able to be pushed through a curved working channel on an endoscope, particularly one with an offset needle entry, for easier positioning in the middle ear. FIG. 20B is a magnified view of the tapered region 907a and the trans-tympanic section 904. The collar region 907a can be located anywhere along the needle length just proximal to the penetrating tip 903 to accommodate differences in anatomy, for example.

FIG. 20C shows a cross section view similar to FIG. 20A. The single fluid lumen 906a, 906b is shown running the length of the needle 900 of the needle assembly 115 and tapering in the transition area of the collar region 907a. FIG. 20D is a magnified view of part of FIG. 20C in cross section including the large bore section 905, the tapered trans-tympanic section 904, and collar region 907a. The distal penetrating tip 903 and a portion of the trans-tympanic section 904 can penetrate past the tympanic membrane into the middle ear during use. In some implementations, the needle 900 can incorporate an external ring or shoulder positioned around the needle shaft at or near the collar 907a. The external ring can have an outer diameter sized to prevent over-insertion of the needle 900 through the tympanic membrane. The external ring, which can be a substantially soft material to avoid damage to ear tissues, can prevent large bore section 905 from passing through the tympanic membrane.

Figure 21A:
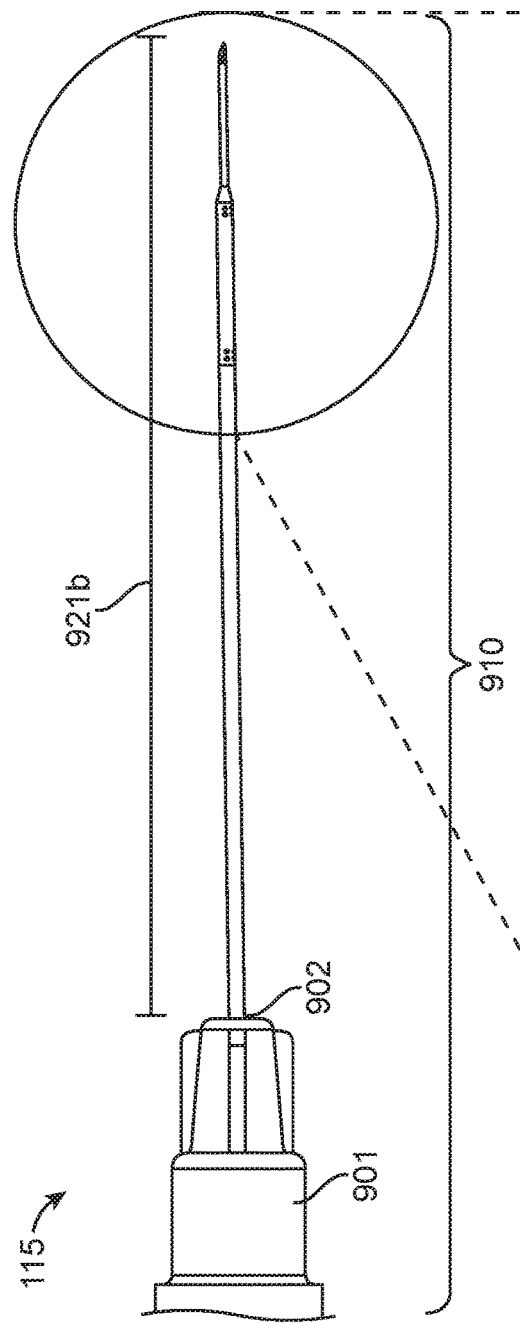
FIGS. 21A-21D show a needle with a concentric vent lumen according to some implementations.

FIG. 21A shows a needle assembly 115 with a concentric vent lumen. More specifically, a concentrically vented needle 910 for penetrating a tympanic membrane 911 to deliver a therapeutic agent to (and reduce pressure in) the middle ear of a patient is shown (FIGS. 21A-21D) is shown. A longitudinally extending cylindrical shaft 921b has a smooth first outer surface diameter 919, a smooth second outer surface diameter 920, a distal end terminating in a penetrating tip 903, a proximal end terminating in a luer connection 901, a first inner surface diameter 917 and a second inner surface diameter 918. Both the first and second inner surface diameters 917, 918 define a fluid lumen 916. A portion of the shaft can be symmetrically tapered about the longitudinal axis of the shaft at a collar region 907b. The collar region 907b gradually transitions from the first outer surface diameter 919 to the second outer surface diameter 920 toward the distal end. The first outer surface diameter 919 may be larger than the second outer surface diameter 920. The proximal end 902 can attach to a luer connector 901 and the luer connector 901 can attach to a number of standard syringes (FIG. 24), modified syringes (FIGS. 3A-3G, 5A-5C), modified otoscopes (FIGS. 4A-4N), or other such devices which contain the therapeutic agent.

Figure 21B:
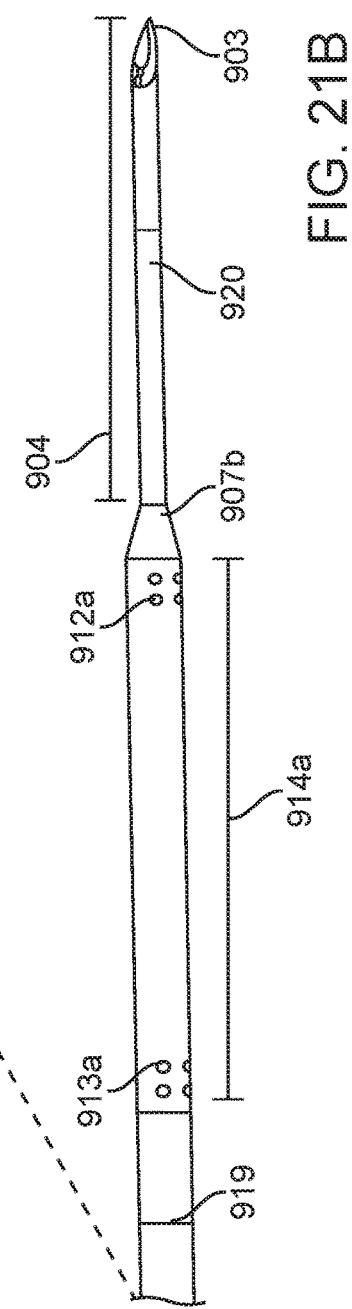
Figure 21C:
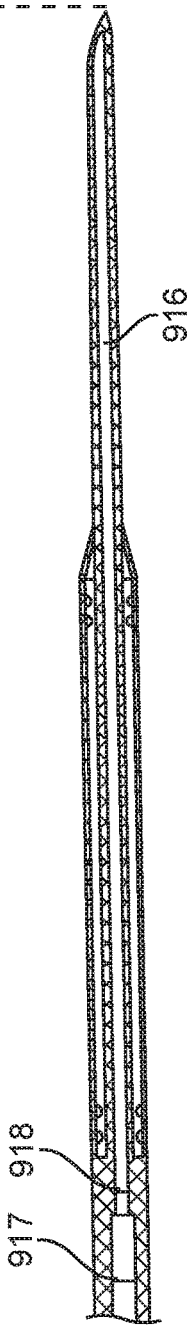
Figure 21D:
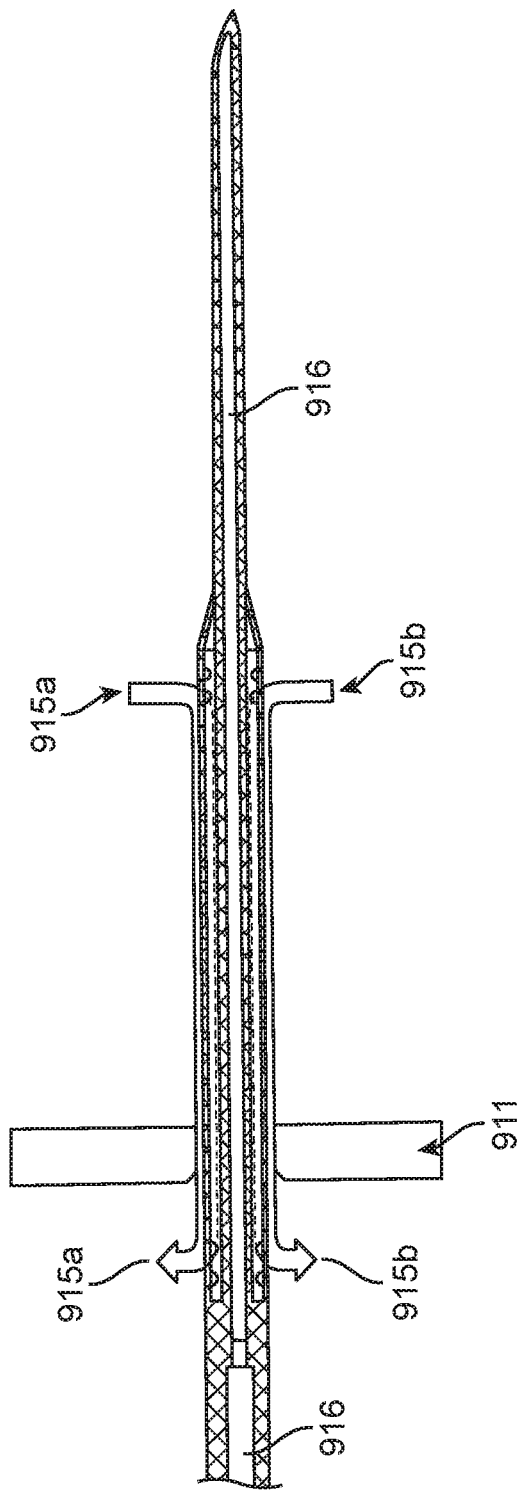

A penetrating tip 903 can be positioned at the distal end and defines a fluid outlet to communicate with the fluid delivery lumen 916 so that the therapeutic agent can exit the fluid lumen 916 longitudinally and enter the middle ear after the tympanic membrane 911 has been penetrated. A vent section 914a can be concentrically positioned proximal to the collar region 907b. The vent section 914a has at least one distal vent 912a and at least one proximal vent 913a with a vent pathway 915a and/or 915b located between the proximal and distal vent(s). The vent pathway 915a and/or 915b runs separately parallel along a length of the fluid pathway 916. The pathway vents air and/or fluid from the middle ear of the patient when the needle can be inserted into the tympanic membrane 911 and the therapeutic agent can be injected into the middle ear when the distal vent(s) 912a and proximal vent(s) 913a are positioned on opposite sides of the tympanic membrane (FIGS. 21B, 21D). Although the pathway vents air since the tympanic cavity is air filled, liquefied effluent may be present in the case of a preexisting middle ear infection, for example. Therefore, it is possible to also vent fluid if needed. As therapeutic agents are injected into the middle ear, pressure may increase and this concentric vented needle allows a more comfortable experience for the patient during treatment of an ear malady.

Any of the needle assemblies described herein can incorporate features to achieve venting or pressure equilibrium such as the vents described above and/or venting through the annular space between inner and outer shafts of needle assemblies described elsewhere herein.

That first inner surface diameter 917 can be larger than the second inner surface diameter 918 and the first inner surface diameter and the second inner surface diameter can transition at a location proximal to the vent section. The distal proximal vent(s) are geometric plane shapes and can be circular, oval, square, rectangular, triangular, rhombus, trapezoid or combinations thereof, for example.

Figure 22D:
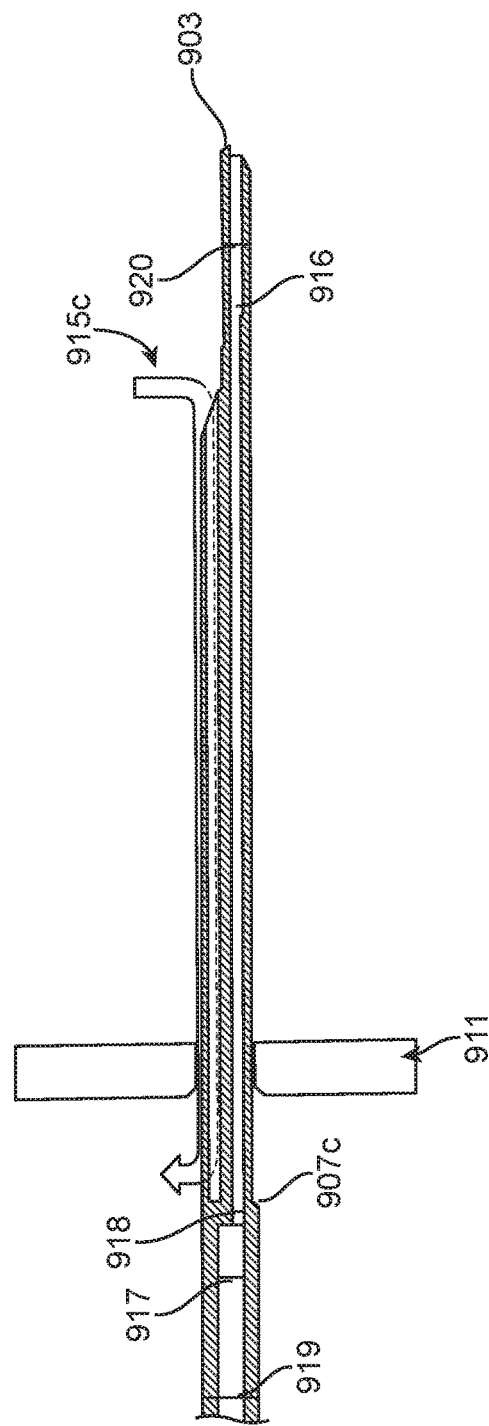

FIG. 22A shows a needle assembly 115 including a parallel vented needle 929 for penetrating a tympanic membrane to deliver a therapeutic agent to, and reduce pressure in, an middle ear of a patient. The needle includes a longitudinally extending cylindrical shaft 921c having a smooth first outer surface diameter 919, a smooth second outer surface diameter 920, a distal end, a proximal end, a first inner surface diameter 917 and a second inner surface diameter 918. Both the first and second inner surface diameters can define a fluid lumen. A portion of the shaft can be symmetrically tapered about the longitudinal axis of the shaft at a collar region 907c, the collar region 907c gradually transitioning from the first outer surface diameter 919 to the second outer surface diameter 920 toward the distal end. The first outer surface diameter 919 can be larger than the second outer surface diameter 920. A proximal end can be configured to attach to a luer connector 901, the luer connector 901 attaches to a syringe containing the therapeutic agent. This can include standard syringes (FIG. 24), modified syringes (FIGS. 3A-3G, 5A-5C), modified otoscopes (FIGS. 4A-4N), or other such devices which contain the therapeutic agent. A penetrating tip 903 positioned at the distal end defines a fluid outlet to communicate with the fluid lumen so that the therapeutic agent can exit the fluid lumen longitudinally and enter the middle ear after the tympanic membrane 911 has been penetrated. A vent section 914b can be positioned parallel to the cylindrical shaft 921c. The vent section 914b has at least one distal vent 912b and at least one proximal vent 913b and a vent pathway 915c located therebetween, the vent pathway 915c running separately parallel along a length of the fluid pathway 916 configured to vent air and/or fluid from the middle ear of the patient when the needle can be inserted into the tympanic membrane 911 and the therapeutic agent may be delivered such that the at least one distal vent 912*b* and the at least one proximal vent 913*b* are positioned on opposite sides of the tympanic membrane 911 (FIG. 22D).

Figure 22E:
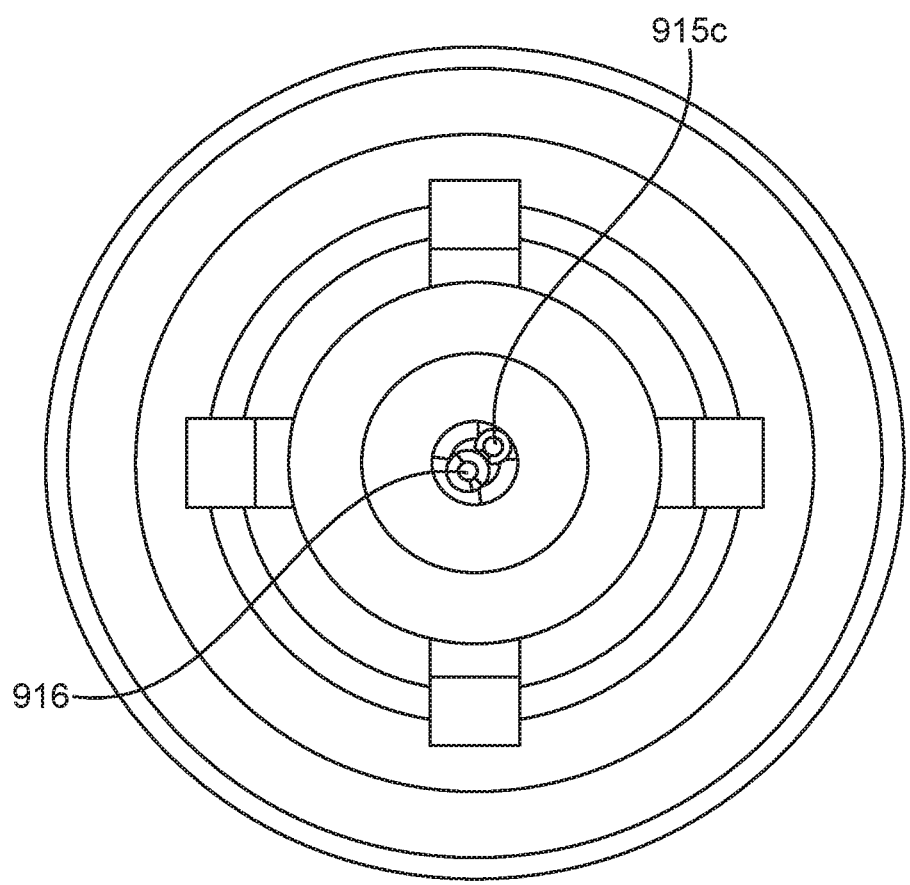
FIG. 22E shows a top view of a needle with a parallel vent lumen.

FIG. 22E shows a top view of a needle with a parallel vent lumen. The vent pathway 915*c* runs separately parallel along a length of the fluid pathway 916.

Figure 23C:
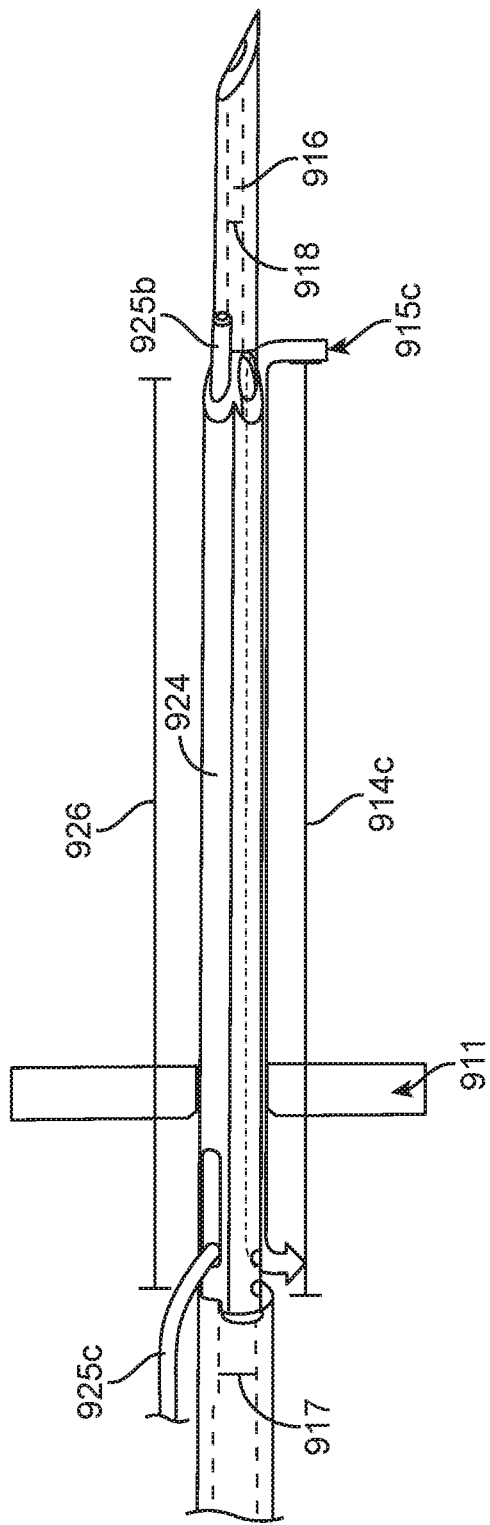

FIGS. 23A-23C show a needle assembly 115 including a needle 930 with a parallel vent lumen and optic line according to some implementations. Note that FIG. 23B is a magnified portion of FIG. 23A rotated about an axis (arrow 928) to show additional detail of optic components and other elements. More specifically, the parallel vented needle with an optical component penetrates a tympanic membrane 911 to deliver a therapeutic agent to, reduce pressure in, and visualize a middle ear of a patient. The needle includes a longitudinally extending cylindrical shaft 921*d*. The shaft 921*d* has a smooth first outer surface diameter 919, a smooth second outer surface diameter 920 (FIG. 23B), a first inner surface diameter 917 and a second inner surface diameter 918. Both the first and the second inner surface diameters 917, 918 define a fluid lumen (FIG. 23C). A portion of the shaft can be symmetrically tapered about the longitudinal axis of the shaft at a collar region 907*d*, the collar region 907*d* gradually transitioning from the first outer surface diameter 919 to the second outer surface diameter 920 toward the penetrating tip 903 at the distal end. The first outer surface diameter 919 can be larger than the second outer surface diameter 920. The proximal end of the shaft 902 attaches to a luer connector 901 which, in turn, can attach to a syringe containing the therapeutic agent. This can include standard syringes (FIG. 24), modified syringes (FIGS. 3A-3G, 5A-5C), modified otoscopes (FIGS. 4A-4N), or other such devices which contain the therapeutic agent. A penetrating tip 903 can be positioned at the distal end of the shaft defining a fluid outlet to communicate with the fluid lumen so that the therapeutic agent can exit the fluid lumen longitudinally and enter the middle ear after the tympanic membrane 911 has been penetrated by the tip 903 (FIG. 23C).

An optic section 926 positioned parallel to the cylindrical shaft 921*d*, the optic section 926 has a distal opening 922 and a proximal opening 923 and a conduit 924 (FIG. 23C) connecting the proximal 922 and distal 923 openings (FIG. 23B). The optic section 926 and associated conduit 924 run parallel to, but separated from, a length of the fluid pathway 916. The conduit 924 encloses an optic line 925*a*. The optic line has a proximal end 925*c* and a distal end 925*b*. The distal end 925*b* of the optic line 925*a* exits the distal opening 922 and into the middle ear of the patient when the needle tip 903 can be inserted into (i.e. penetrates) the tympanic membrane 911 such that the distal 922 and proximal 923 openings are positioned on opposite sides of the tympanic membrane 911 (FIG. 23C). The optic line 925*a* can be a fiber optic line that provides illumination and/or imaging capabilities in real time. The proximal end of the optic line 925*c* can be connected to a camera, computer monitor, television or other similar device 927. The optic line 925*a* can include a pressure sensor and/or a positional sensor. The positional sensor can assist with positioning the needle, for example. The optic line 925*a* can include acrylate-coated or polyimide-coated fibers and the needle can be sterilized in an autoclave or other such device.

A vent section 914*c* can be positioned parallel to the cylindrical shaft 921*c* (FIGS. 23A and 23C). The vent section 914*c* has at least one distal vent 912*c* and at least one proximal vent 913*c* and a vent pathway 915*c* located therebetween, the vent pathway 915*c* running separately parallel along a length of the fluid pathway 916 configured to vent air and/or fluid from the middle ear of the patient when the needle can be inserted into the tympanic membrane 911 and the therapeutic agent can be delivered such that the at least one distal vent 912*c* and the at least one proximal vent 913*c* are positioned on opposite sides of the tympanic membrane 911 (FIG. 23C).

Figure 23D:
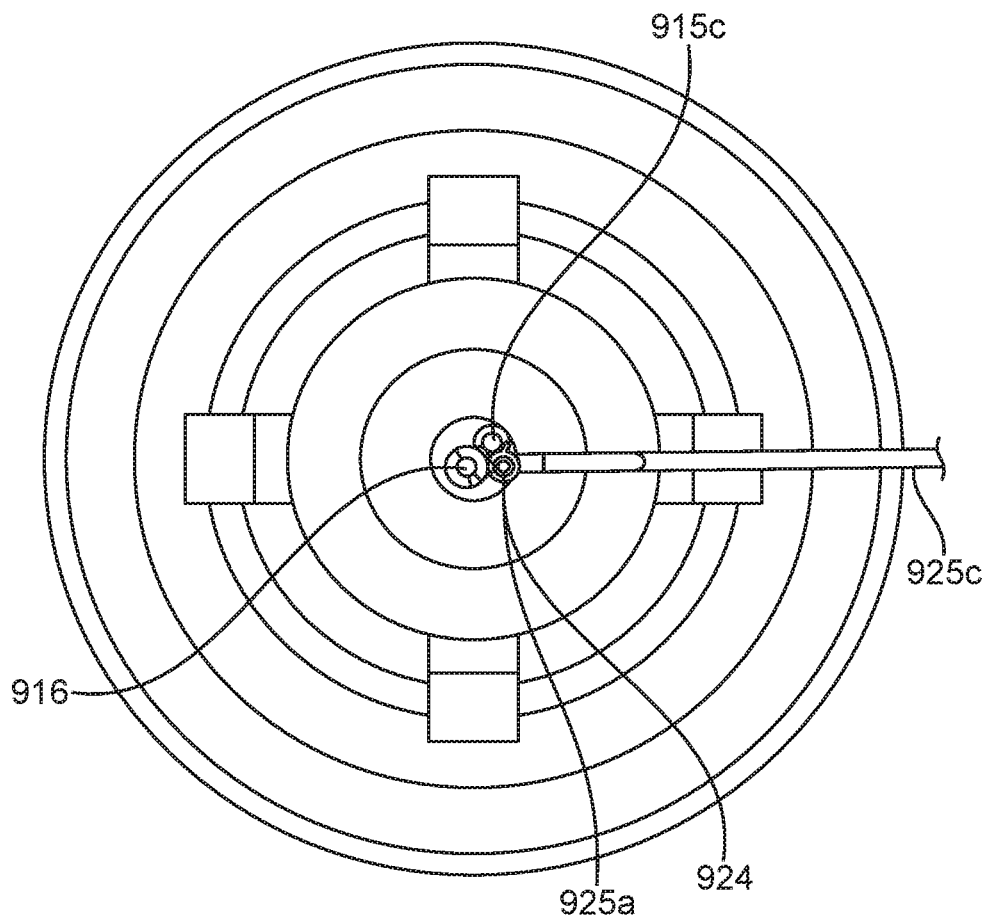
FIG. 23D shows a top view of a needle with a parallel vent lumen and optic line according to some implementations.

FIG. 23D shows a top view of a needle with a parallel vent lumen and optic line according to some implementations. The vent pathway 915*c* runs parallel along a length of the fluid pathway 916 and can be separate from the fluid pathway 916. The conduit 924 also runs parallel along a length of the fluid pathway 916 and vent pathway 915*c* but can be a separate conduit from the other pathways. The conduit 924 encloses an optic line 925*a* which is shown in the middle of conduit 924 in FIG. 23D.

Figure 24:
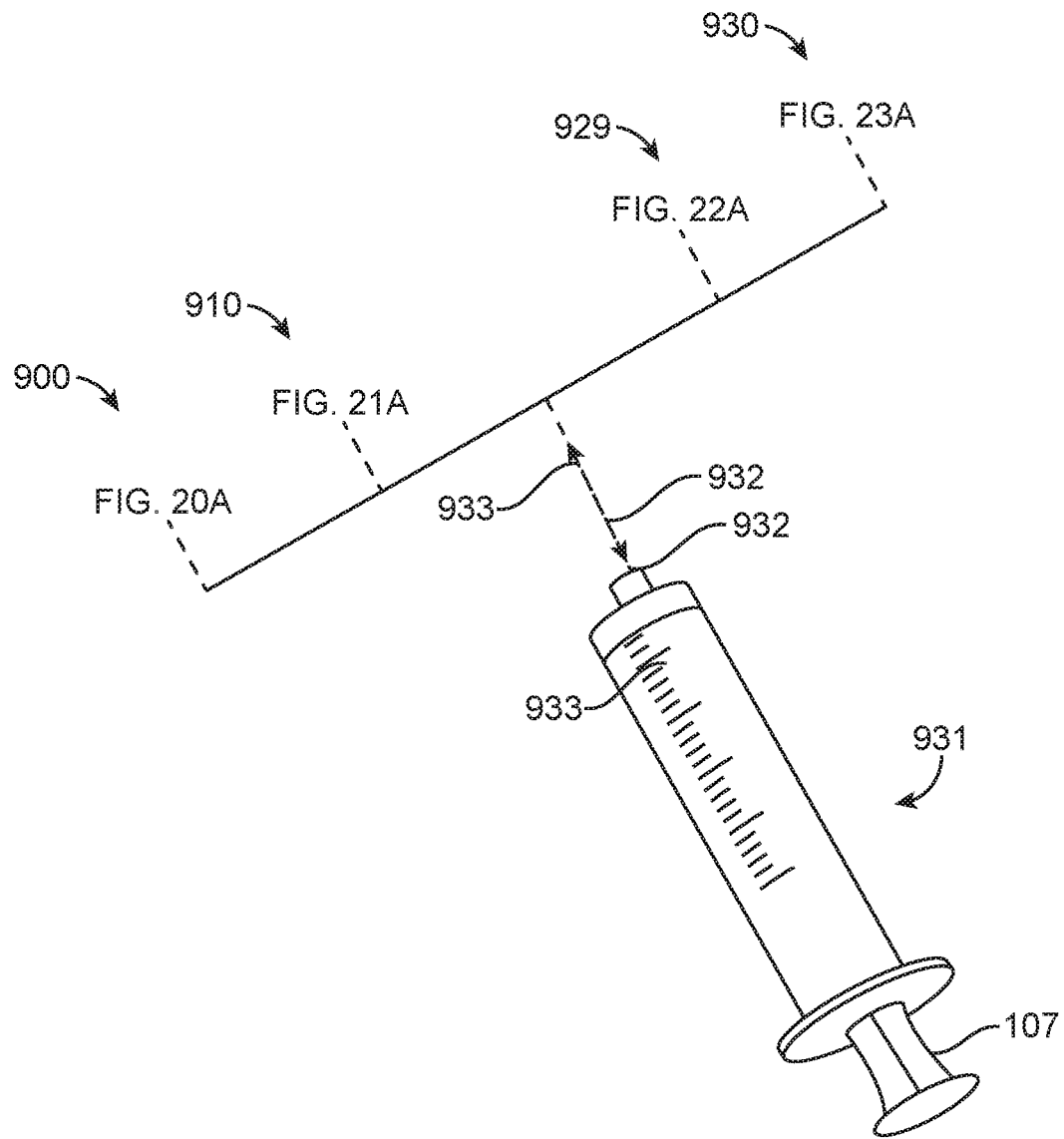
FIG. 24 shows a generic syringe for injection according to some implementations.

Turning now to FIG. 24 a standard (i.e., generic, traditional, typical) syringe 931 can be filled with a chosen volume of therapeutic agent 933 for injection into a middle ear using any one of the intratympanic needles 900 (FIG. 20A), 910 (FIG. 21A), 929 (FIG. 22A), or 930 (FIG. 23A), for example. The distal end 932 of the syringe 931 can accept the luer connection 901 to attach any one of the needles 900, 910, 929, or 930. The luer connection 901 can accept a luer lok tip (i.e. secure screw type connection), slip tip (i.e. slip or push-on connection), eccentric tip (i.e. off center tip), catheter tip (i.e. long tapered slip tip) or other connections known to those of skill in the art. It may be possible to interchange, replace or change out one needle for a similar or different needle depending on a range of factors or as the procedure may dictate. In this manner, a needle can be added 932 or removed 933 from the syringe 931. For example, if it is important to view the middle and/or inner ear during the injection, needle 930 can be used since it includes an optic component. Any combination of the needles 900, 910, 929, or 930 and/or syringe 931 can be single use (i.e. disposable) or multi-use (i.e. post sterilization). It should be appreciated that the various needles described herein (e.g., 900, 910, 929, 930, 1515, etc.) can incorporate one or more features of any of the other needles described herein.

Again with respect to FIG. 2C, the device 100 can be an at least partially powered instrument incorporating an injection module 400 in operable communication with an electronics module 500. The injection module 400 can vary depending on the implementation of the device 100, but can include one or more of the needle assembly 115 configured to be extended and retracted by a drive element 405, and a pumping mechanism 410 configured to urge fluid from the reservoir 120 towards the patient. The electronics module 500 of the device 100 can include one or more of a user interface 505 including the one or more actuators 107 and a controller 510. The electronics module 500 can also optionally include a communication port 515 and one or more targeting features 520 configured to improve targeting and/or visualization of the injection, which will be described in more detail below.

The user interface 505 can receive manual input from a user and may include the one or more actuators 107, including pushbuttons, keypads, a touchscreen, or other inputs. The configuration of the one or more actuators 107 can vary. The various features of the device can include a separate actuator 107 for activation. For example, extension of the needle assembly 115 can be achieved by activating a first actuator and retraction of the needle assembly 115 can be achieved by activating a second actuator. Alternatively, both extension and retraction of the needle assembly 115 can be achieved by activating a single actuator that is a two-stage actuator such that the direction of movement achieved depends upon the degree of actuation of the actuator 107. Extension can be achieved by a first activation of the actuator 107 and retraction can be achieved by a second activation of the actuator 107. Additionally, extension and retraction can be achieved in a two-step manner upon a single activation of the actuator 107. The user interface 505 can also include one or more inputs that modify the actuation achieved upon activation of the one or more actuators 107. For example, the cap element 178 shown in FIG. 4L (or another input on the housing 105) can function as an adjustment knob configured to modify the degree of extension of the needle assembly 115 achieved upon activation of the actuator 107. The cap element 178 may be used to modify length of shaft extension, priming of the shaft, and/or inner cannula deployment. The one or more inputs or actuator(s) 107 can be mechanical or electrical. Although the above describes the user of "triggers" or "actuators" to cause a particular action of the device to occur, the actuation may also occur by programming of the device to perform a particular action via a user interface on the instrument.

The user interface 505 may include a display or other visual indicators such as one or more lights, speakers, vibration motors, etc. to provide visual, tactile, and/or auditory instructions and/or information to the user, such as information relevant to alignment and proper distance achieved prior to an injection as described elsewhere herein. The user interface 505 can provide the user with alerts and information regarding the status of the device and the device components during use such that manual and/or automatic adjustments can be made. The user interface 505 can include an LED or other type of display using, for example, electrical filaments, plasma, gas, or the like. The user interface 505 can include a touchscreen type of display.

Still with respect to FIG. 2C, the controller 510 can include at least one processor and a memory device. The memory may be configured for receiving and storing user input data as well as data acquired during use of the device 100. The memory can be any type of memory capable of storing data and communicating that data to one or more other components of the device, such as the processor. The memory may be one or more of a Flash memory, SRAM, ROM, DRAM, RAM, EPROM, dynamic storage, and the like. The memory can be configured to store user information, history of use, injections made, and the like.

In some implementations, one or more components of the device 100 can be powered by a battery. The battery can be a removable battery that can be enclosed within a portion of the device housing 105. The battery can have different chemical compositions or characteristics. For instance, batteries can include lead-acid, nickel cadmium, nickel metal hydride, silver-oxide, mercury oxide, lithium ion, lithium ion polymer, or other lithium chemistries. The instruments can also include rechargeable batteries using either a DC power-port, induction, solar cells or the like for recharging. Power systems known in the art for powering medical devices for use in the operating room are to be considered herein. It should be appreciated that other power systems known outside the art of medical devices are to be considered herein as well.

Still with respect to FIG. 2C, the device 100 can optionally include a communication port 515 can be configured to communicate with another device. In some implementations, the communication port 515 can communicate with the removable cartridge 125. In some implementations, the communication port 515 can communicate with an external computing device 600. The communication port 515 of the device 100 can be a wired communication port such as a RS22 connection, USB connection, Firewire connections, proprietary connections, or any other suitable type of hardwired connection configured to receive and/or send information to the external computing device 600. The communication port 515 can alternatively or additionally include a wireless communication port such that information can be fed between the instrument 100 and the external computing device 600 via a wireless link. The wireless connection can use any suitable wireless system, such as Bluetooth, Wi-Fi, radio frequency, ZigBee communication protocols, infrared or cellular phone systems, and can also employ coding or authentication to verify the origin of the information received. The wireless connection can also be any of a variety of proprietary wireless connection protocols. In some implementations, the device 100 has no user interface 505 and communicates with the external computing device 600 configured to display information related to the instrument 100. It should be appreciated that the external computing device 600 with which the instrument 100 communicates can vary including, but not limited to, desktop computer, laptop computer, tablet computer, smartphone or other device capable of displaying information and receiving user input.

The communication port 515 of the device 100 can communicate with the cartridge 125. In some implementations, the communication port 515 can communicate with a transponder or other data element 176 such as an encoder or bar code type strip on the housing 175 of the cartridge 125 configured to be in communication with the communication port 515. As an example, the element 176 can store data about the cartridge 125 such as the substance contained in the reservoir 120, volume, concentration, date of manufacture, as well as any other information regarding the substance or the cartridge 125. The data can be stored within the element 176 and communicated to and received by the controller 510 of the instrument 100 upon "reading" the element 176 on the cartridge 125. For example, the cartridge 125 can be bar-coded such that the device 100 reads what substance 122 is loaded in the device. The identification of the cartridge 125 can be used by the controller 510 to set or to adjust certain parameters. The data can be received as part of a set-up procedure and preparation of the instrument for actual use. This can be initiated automatically by software run by the controller 510 of the instrument 100 without any user input. Alternatively, the user can manually enter information about the substance 122 on the user interface 505 of the device 100. The device 100 can also be used without any substance being entered.

The communication can be one-way or two-way wireless communication. The communication can be a wireless communication such as a transmitter and/or receiver, radiofrequency (RF) transceiver, WI-FI connection, infrared or Bluetooth communication device. The data element 176 of the cartridge 125 can include an encoder or bar code type strip configured to be scanned and read by a corresponding reader device of the instrument 100 that is in operative communication with the controller 510. The data element 176 may alternatively be an RFID chip or the like that transmits data to a reader such as a data receiving processor or the like. Such encoder devices include the ability to securely transmit and store data, such as, via, encryption, to prevent unauthorized access or tampering with such data. The memory of the controller 510 can be configured to maintain a record for a particular cartridge 125. For example, the record can indicate when the cartridge 125 is expired such that it should not be used for an injection.

The processor, the memory, and the storage device and the input/output devices can be interconnected via a system bus. The processor can be capable of processing instructions for execution within the systems. Such executed instruments can implement one or more of the processes described herein related to use of the instrument. For example, one or more signals from a first sensor can be communicated to and transformed into one or more processed signals representative of or providing information relating to what was sensed including, but not limited to one or more of torque, energy, power, accumulated power, time, material strength, material density measurements, spindle speed, depth, feed control, force, 3D orientation of penetration, drilling energy, pull-out force, screw insertion energy, and the like.

The processor of the controller 510 can be a single-threaded processor or a multi-threaded processor. The processor of the controller 510 can be capable of processing instructions stored in the memory and/or on a storage device to display information to the user such as on a graphical display or other user interface provided via an input/output device. It should be appreciated that the graphical display need not be on the device 100, but can be on an external computing device 600 in communication with the device 100. Alternatively, it should be appreciated that the output need not be graphical and can be any of a variety of indicators (lights, sounds, tactile feed-back).

As mentioned above, the electronics module 500 can also optionally include one or more targeting features 520 configured to improve targeting and/or visualization of the injection. In some implementations, the targeting features 520 includes one or more sensing elements 525 including, but not limited to, a proximity sensor, aiming elements 530 configured to project one or more targeting beams, illumination elements 535, and any of a variety of other visualization aids including, but not limited to LEDs, lenses, light pipes, filters, etc.

Figure 9B:
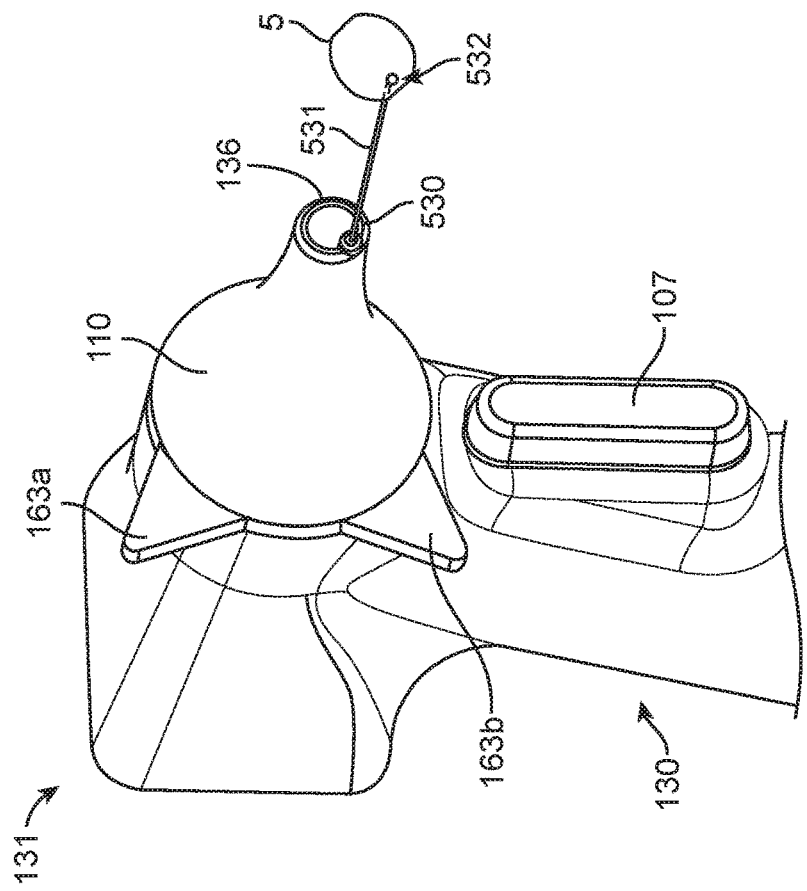
FIGS. 9A-9C are various views of an implementation of the device of FIG. 4A incorporating an aiming element.
Figure 9A:
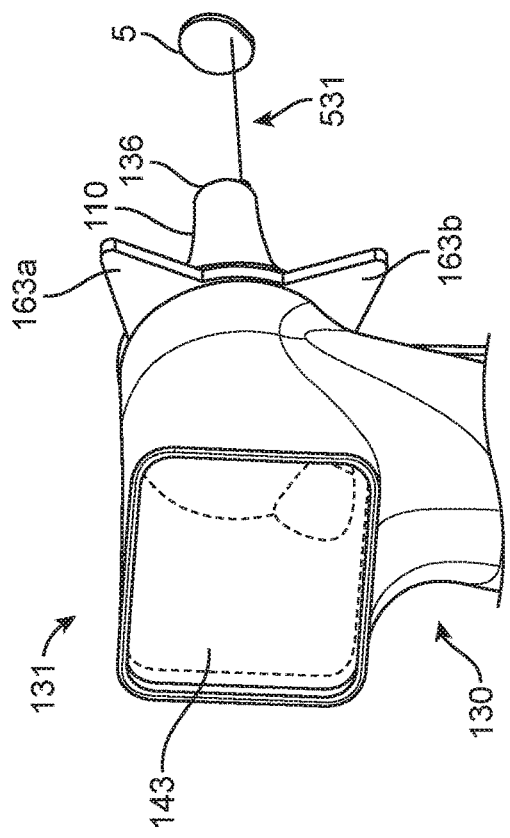
Figure 9C:
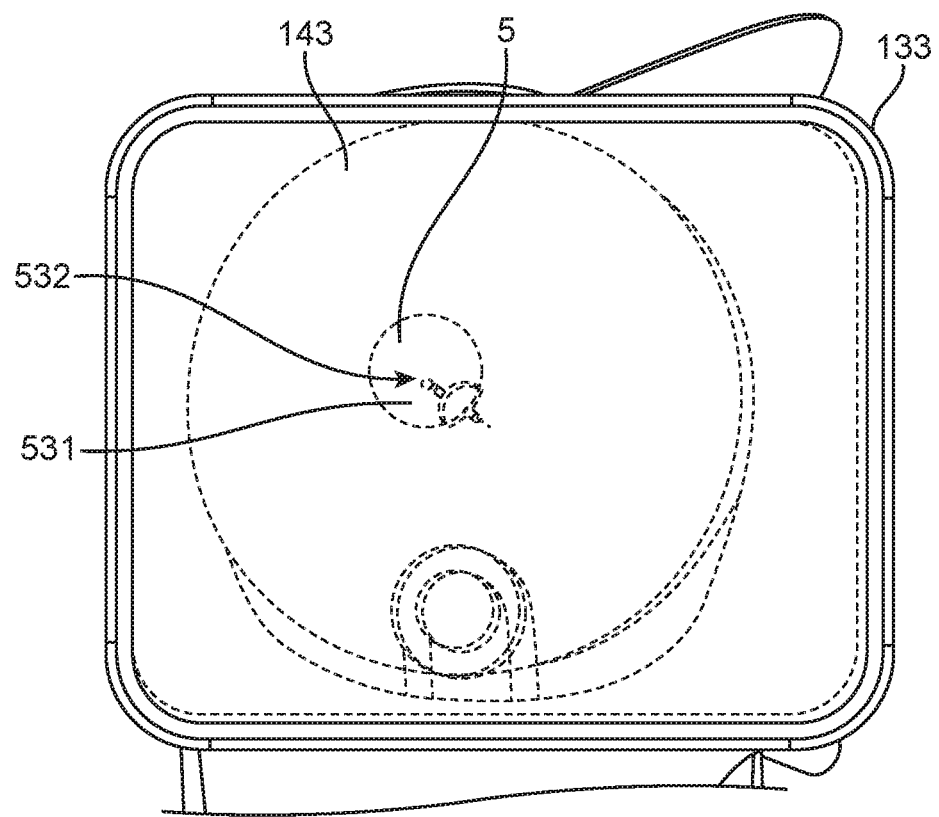

FIGS. 9A-9C illustrate an implementation of a device 100 having a canal guide 110 incorporating one or more aiming elements 530 configured to provide visual cues or feedback to the user before, during, and/or after membrane 5 penetration. In an implementation the one or more aiming elements 530 can direct at least one aiming light beam 531 towards an object of interest (i.e. the tympanic membrane 5) in order for the user to visualize where the needle assembly 115 will strike prior to actuation of the device. The light beam 531 can be a very narrow beam that projects onto the object of interest and aligns with a point 532 the shaft 117 of the needle assembly 115 will strike. The beam 531 generated by the aiming element 530 can provide a variety of visual cues, including one or more dot(s), box(es), dashed lines, crosshairs, or other configuration of visual cue at the point 532. The visual cue can be static, dynamic, or responsive. For example, the visual cue can pulse, strobe, flash continuously or semi-continuously, change brightness, or a combination thereof. Additionally, the visual cue can change modes to provide feedback to the user, such as to indicate optimum distance or angle relative to the target of interest. Appropriate positioning of the device can allow for faster, more efficient, and safer outcomes for a successful injection. FIG. 9C illustrates a view through the viewing lens 143 of the device 100 when using the aiming element 530. The visible point 532 of light helps overcome the loss of depth perception due to monocular vision.

The aiming element 530 can include any of a variety of one or more optical elements including an aiming light source, a lens, pinhole element, a light pipe, a concentrator element, with or without a diffusing element, a light guide, obstructing element, light collimator, etc. The aiming light source of the aiming element 530 can include, for example, an LED, OLED, laser diode, and the like configured to be electrically connected to a printed circuit board (PCB). The aiming element 530 can be optimized for LED light sources, for example, including a light pipe to concentrate, channel, and diffuse the light projected. The shape of the beam 531 and thus, the shape of the visible point 532 can vary including, circular, square, cross, or an "x", the profile of which the user will see projected onto the target location.

Figures 1, 10B:
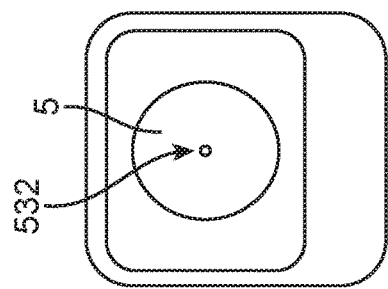
Figures 1, 10C:
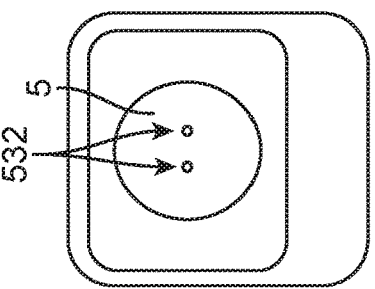
Figure 10B:
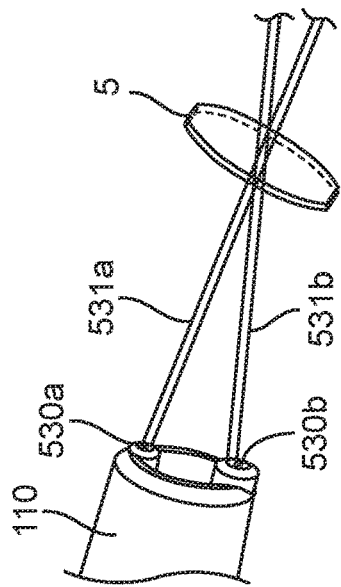
Figure 10C:
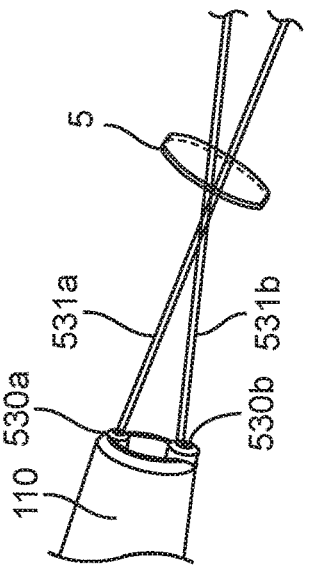
Figure 10A:
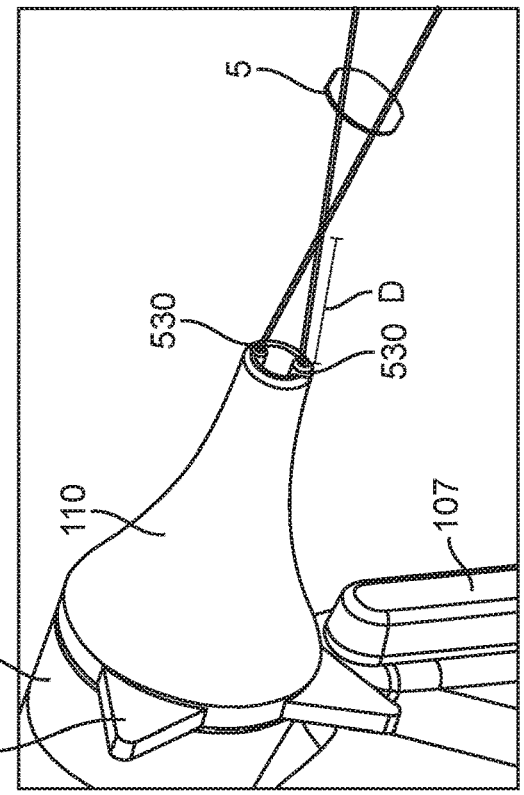

The shape of the light beam 531 projected onto the target location by the aiming element 530 can change depending on the distance the canal guide 110 is from the target. FIGS. 10A-10C illustrate an implementation of the aiming element 530 in which more than a single beam 531 can be directed towards the target (e.g. tympanic membrane 5). The aiming element 530 can direct a first beam 531*a* at a first angle relative to the canal guide 110 and a second beam 531*b* at a second angle relative to the canal guide 110. The angles can be such that the first and second beams 531*a*, 531*b* cross a distance D away from the distal-most end of the canal guide 110. The two beams 531*a*, 531*b* allow the user to gauge the proximity of the target 5 relative to the distal-most end of the canal guide 110 based whether two points of light 532 are projected or one point 532. When the canal guide 110 is positioned too far away from (or too near) the target 5, the user will see both the first and second beams projected on the target 5 as two points 532 (see FIGS. 10A and 10C and 10C-1). When the canal guide 110 is positioned at an optimum distance D from the target 5, the user will see a single beam projected dot 532 (see FIGS. 10B and 10B-1). It should be appreciated that the "dot" may be any of a variety of shapes as described above.

Figure 11:
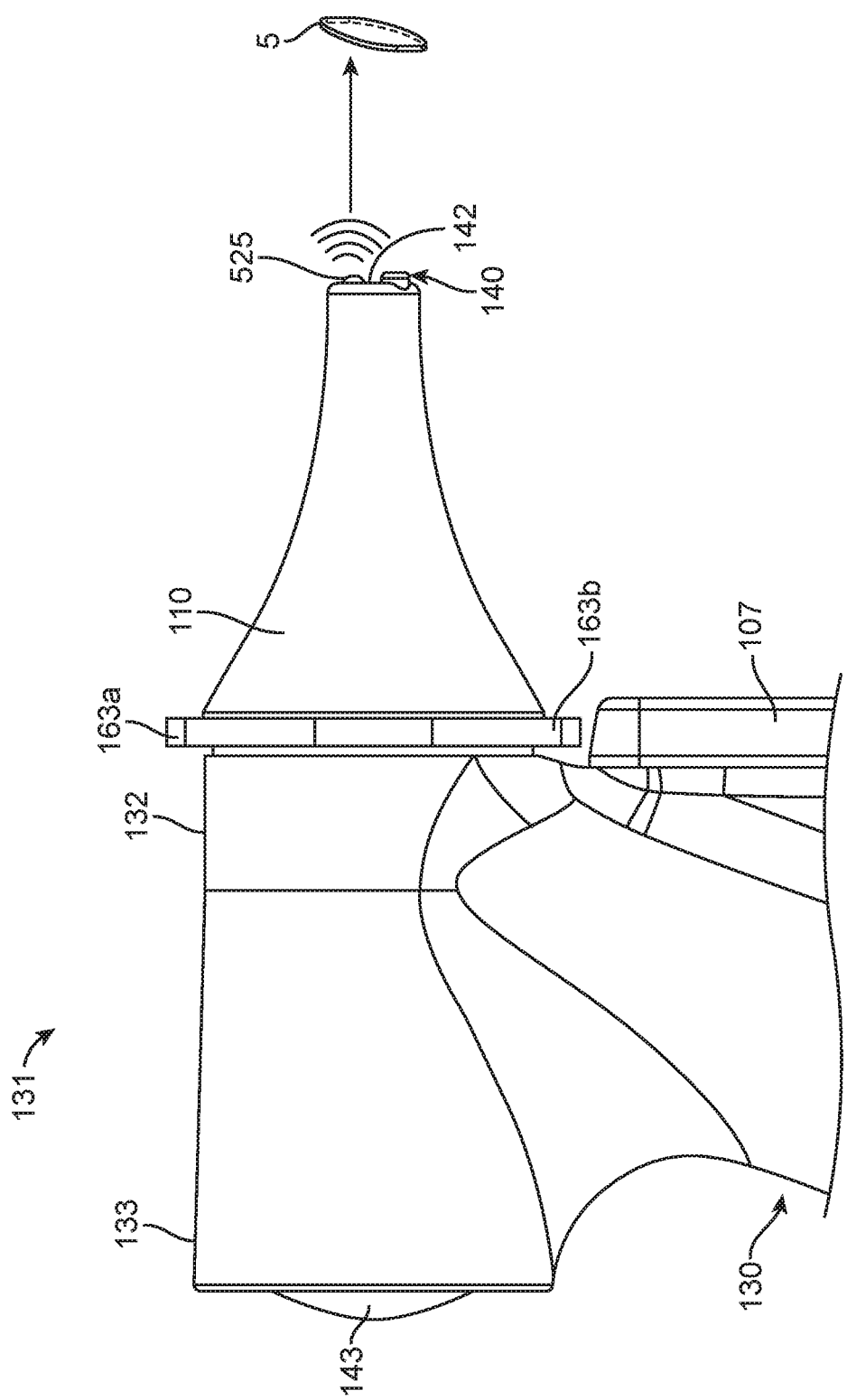
FIG. 11 is a side view of an implementation of the device of FIG. 4A incorporating a sensing element configured to provide depth guidance.

Now with respect to FIG. 11, the device 100 can additionally or alternatively include one or more sensing elements 525 to improve the targeting of the tympanic membrane 5. In an implementation, the sensing element 525 is a proximity sensor. The sensing element 525 can be an infrared sensor configured to record the infrared radiation (IRR) emitted by the membrane, a pressure sensor configured to detect contact, a laser distance sensor, electrode to sense tissue contact, for example to differentiate between the tympanic membrane 5 and other tissues in the ear.

The signals from the proximity sensor(s) 525 can be processed into one or more processed signals representative of relative distance between the canal guide 110 and the target (e.g., the tympanic membrane 5). The sensor 525 can communicate information related to the relative distance to the controller 510 of the electronics module 500. The information communicated can be provided in real-time to the user, for example, via the user interface 505, that in turn can provide visual, auditory, and/or tactile cues to the user regarding readiness for injection of the membrane 5. In some implementations, information from the sensing element 525 (and/or the aiming element 530) can communicate with the controller 510 of the device such that the controller 510 automatically triggers an injection at the proper proximity and aim without any input from the user.

Figure 12B:
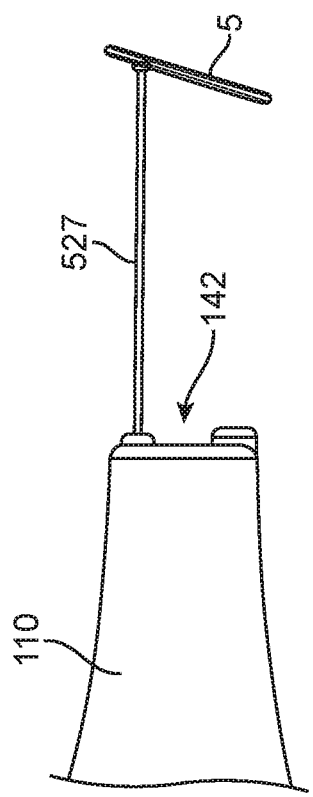
FIGS. 12A-12B are views of another implementation of the device of FIG. 4A incorporating a physical proximity sensor to provide depth guidance.
Figure 12A:
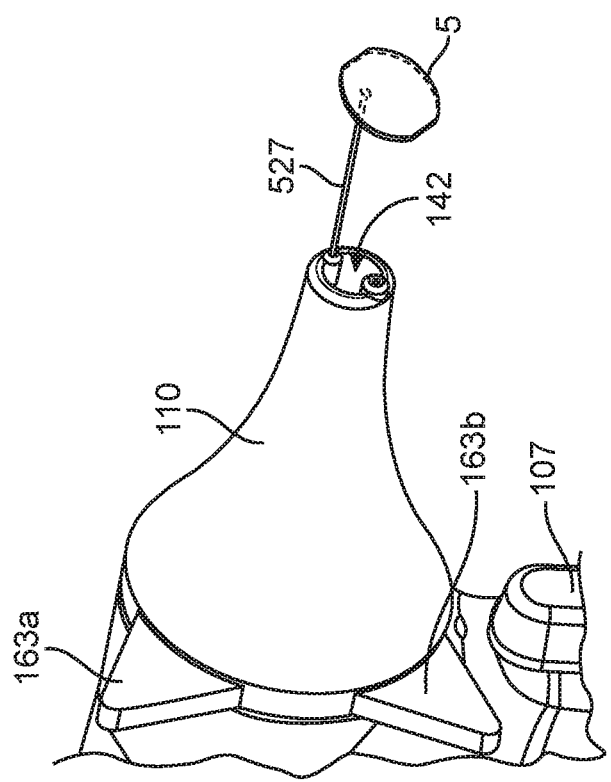

The proximity sensor 525 can be optical, acoustic, or another type of sensor. The proximity sensor 525 can be electronic or fully mechanical. In an implementation, the proximity sensor 525 is a physical proximity sensor configured to instantaneously determine optimum depth of the device 100 (see FIGS. 12A-12B). The proximity sensor 525 can include a post 527 extending a distance distal to the canal guide 110. The post 527 can communicate a signal to the device upon physical engagement between the distal end of the post 527 and the tympanic membrane 5. The device 100, in turn, can provide a visual, tactile, and/or auditory cue to the user related to the contact with the membrane 5. The user can then actuate injection or the device can automatically actuate the injection. The post 527 can be a semi-flexible contact sensor tip that is incapable of puncturing or damage the tympanic membrane upon contact.

Figure 13:
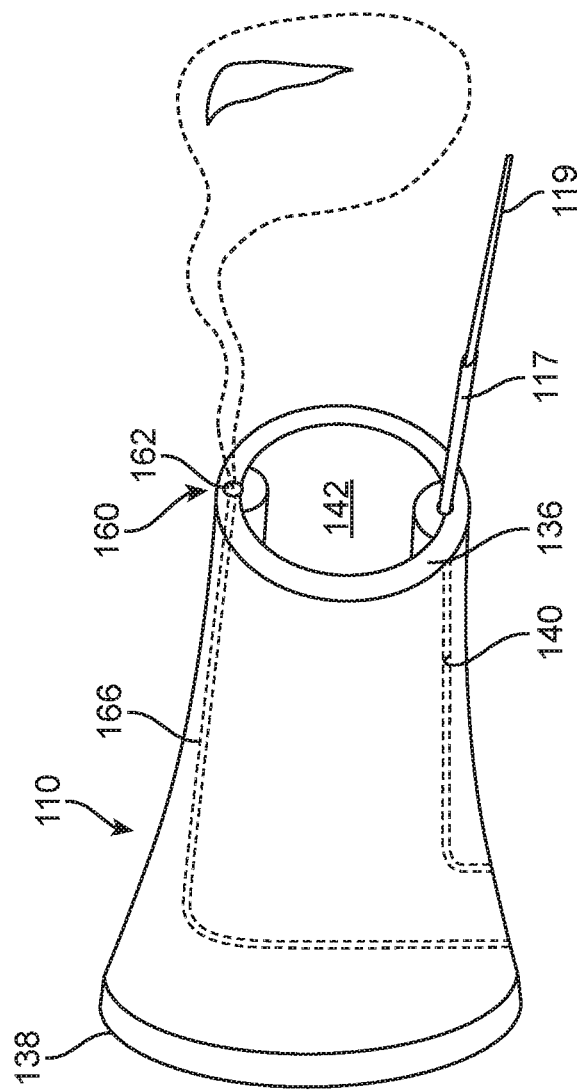
FIG. 13 is a view of a canal guide configured to deliver a substance to the ear canal.

Described throughout are devices configured to penetrate a target for delivery of a substance through a cannula into a cavity such as the tympanic cavity 30. It should be appreciated the devices described herein can deliver a treatment to other parts of the ear, such as the ear canal 40. FIG. 13 illustrates an implementation of a canal guide 110 configured to deliver a treatment from its distal end 136 in addition to delivering a treatment through the needle assembly 115. At least a portion of the canal guide 110 and/or the contact tip 150, if present, can be coated in or saturated with a substance, such as a topical analgesic compound or antibacterial compound, to reduce patient discomfort and/or risk of infection. The canal guide 110 can include a dispenser 160 extending through a region of the canal guide 110 configured to deliver into the ear canal 40 a substance stored in an additional reservoir (not shown). The reservoir can be an internal reservoir to the device 100 or an external reservoir in fluid communication with the device 100. The substance can be a liquid, powder, gel, dispersion, aerosols, or other formulation as is known in the art.

The dispenser 160 can have nozzle 162 at a distal-most end 136 of the canal guide 110 configured to create at least one stream of substance for delivery in a region adjacent to the distal-most end 136. The dispenser 160 can be fluidly connected to the additional reservoir via tubing 166 extending through a region of the device 100. The canal guide 110 in this configuration can include three lumens, a first lumen 140 through which the needle assembly 115 extends, a second lumen 142 through which a user may view the target via a lens 143, and a third lumen of the nozzle 162. The same or an additional actuator 107 can be incorporated to control fluid delivery from the dispenser 160 such that fluid from the reservoir can be pumped, injected, ejected, dripped, sprayed, or otherwise delivered from the nozzle 160 to the ear canal 40.

Figure 14B:
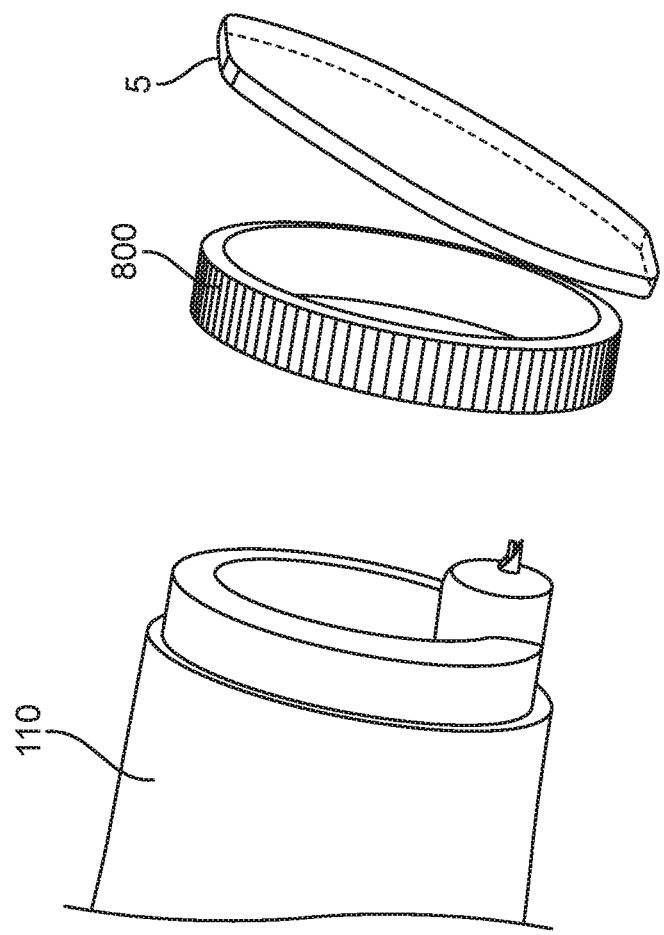
FIGS. 14A-14B are views of a temporary implant being delivered to the ear canal from the canal guide.
Figure 14A:
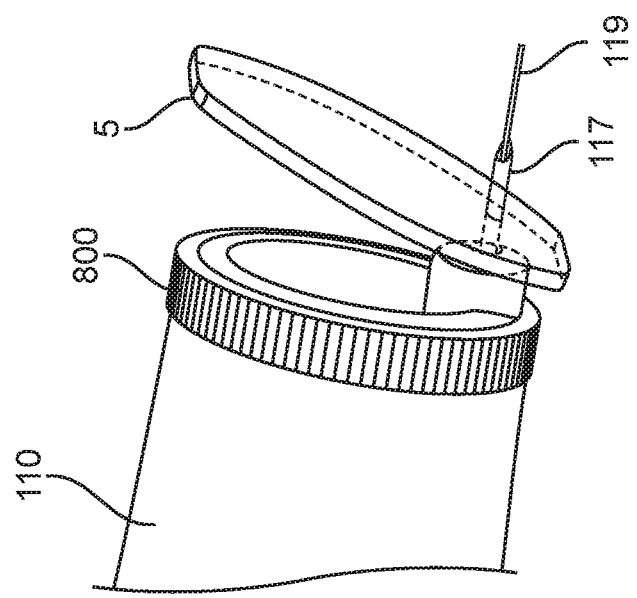

The device 100 can also deliver a substance to the ear canal 40 by dispensing a temporary implant 800 within the ear canal 40 that is impregnated with the substance (see FIGS. 14A-14B). In some implementations, the implant 800 can be detachably coupled to a region of the canal guide 110. The implant 800 can be impregnated with a treatment substance such as a topical analgesic and/or antiseptic configured to reduce patient discomfort and/or risk of injection. The implant 800 can be a ring-shaped element configured to engage with and surround a distal end region of the canal guide 110. The implant 800 can be positioned on the canal guide 110 prior to use and can detach from the canal guide 110 upon insertion of the canal guide 110 into the ear canal 40. The implant 800 can remain in place within the ear canal 40 near the tympanic membrane 5 for a period of time. The treatment substance can elute from the implant 800 for the period of time. The implant 800 can vary in material including any of a variety of biocompatible drug release materials, including but not limited to a porous material such as a polymer or a collagen sponge, a wicking material, permeable silicone, packed bed, small porous structure or a porous frit, multiple porous coatings, nanocoatings, rate-limiting membranes, matrix material, a sintered porous frit, a permeable membrane, a semi-permeable membrane, a capillary tube or a tortuous channel, nano-structures, nano-channels, sintered nanoparticles and the like. The implant 800 can be biodegradable or bioabsorbable such that it does not need to be removed after positioning within the ear canal 40. The implant 800 can also be removed after a period of time by falling out without assistance or by a doctor upon follow up.

Methods of Use

In an implementation, the device 100 (which can be prefilled with a substance 122 in the reservoir 120 to be delivered or filled immediately prior to use such as by insertion of a cartridge 125) has the needle assembly 115 in a fully retracted configuration. In some implementations, the device 100 can be powered on and data acquired related to the injection. A user can insert the forward end of the canal guide 110 into a patient's ear canal 40. The positioning, alignment, and targeting of the device 100 within the ear canal 40 can vary as described herein. For example, in some implementations, the device 100 can be inserted without any visualization or alignment aids. In other implementations, the device 100 can be aligned by locating the tympanic membrane 5 through a viewing lens 143 of the device 100 or a separate otoscope handle 300. The canal guide 110 can be positioned a distance away from the target or in direct contact with the target to be injected. Upon achieving proper insertion distance and rotational alignment with the target, the user can activate an actuator 107, such as a spring-release element, to cause the needle assembly 115 to extend out from the distal end of the canal guide 110. The shaft 117 can penetrate the targeted portion of the tympanic membrane 5, which can simultaneously cause the cannula 119 extending through the lumen of the shaft 117, to be positioned through the tympanic membrane 5. The shaft 117 can immediately retract back into the canal guide 110 such that it no longer extends through the membrane 5 leaving the cannula 119 in place. Alternatively, the user can activate the same or a different actuator 107 to cause the shaft 117 to retract back into the canal guide 110. The user can adjust the canal guide of the cannula 119 within the tympanic cavity 30 (e.g. length of extension and/or rotation around the longitudinal axis A of the canal guide 110) to ensure it is positioned in a desired location for treatment delivery. The substance 122 from the reservoir 120 can be injected automatically upon actuation of the needle assembly 115 or upon an additional activation of an actuator 107 (the same or different actuator 107) to cause fluid flow out the distal end region of the cannula 119 positioned within the middle ear 30. The device 100 can be used similarly for the same patient a second time, for example, in the other ear. One or more components of the device 100 can be disposed of after use including, but not limited to, the cartridge 125, the needle assembly 115, the canal guide 110, or the entire device itself Therapeutics and Diseases The treatment devices described herein can be used to treat and/or prevent a variety of other conditions, including but not limited to hearing loss, including hidden hearing loss, noise-induced hearing loss, age-related hearing loss, drug-induced hearing loss, such as chemotherapy-induced hearing loss or aminoglycoside-induced hearing loss, sudden sensorineural hearing loss (SNHL), and the like. Any of a variety of ear disorders can be treated using the devices described herein. The treatment devices described herein can be used to treat other ear disorders such as tinnitus. The treatment devices described herein can be used to treat balance disorders including vertigo, Meniere's disease, vestibular neuronitis, labyrinthitis, and the like.

Examples of therapeutic agents that may be delivered by the treatment devices described herein and/or are described in the applications incorporated by reference herein are provided below.

Therapeutics that can be delivered from the devices described herein include but are not limited to antioxidants, anti-inflammatories, steroids, antimicrobials, NMDA receptor antagonists, nootropics, anti-apoptotic agents, neurotrophins, neuroprotective agents, neural protective proteins such as CNTF, BDNF, PEDF, NGF, and the like, cannabinoids, monoclonal antibodies, other proteins, gene therapies like iRNA, and protein therapies like anti-VEGF. Gene therapy can include DNA, RNA, iRNA, siRNA, etc., antisense oligonucleotide, a stereopure nucleic acid, a virus, adeno-associated virus (AAV), non-viral gene therapy, vexosomes, liposomes, CRISPR cas9 mediated homology-independent targeted integration (HITI) or homology directed repair (HDR) to modify the genetic components of various diseases of the ear. The therapeutics can include anti-VEGFs such as Avastin (bevacizumab), Lucentis (ranibizumab), Caprelsa (vandetanib), Inlyta (axitinib), Votrient (pazopanib), and Eylea (Afilibercept).

As an example, the therapeutic agent can include, but is not limited to antimicrobials such as antibiotics such as tetracycline, chlortetracycline, bacitracin, neomycin, polymyxin, gramicidin, cephalexin, oxytetracycline, chloramphenicol kanamycin, rifampicin, ciprofloxacin, tobramycin, gentamycin, erythromycin and penicillin; antifungals such as amphotericin B and miconazole; anti-bacterials such as sulfonamides, sulfadiazine, sulfacetamide, sulfamethizole and sulfisoxazole, nitrofurazone and sodium propionate; antivirals such as idoxuridine, trifluorotymidine, acyclovir, ganciclovir and interferon; antiallergenics such as sodium cromoglycate, antazoline, methapyriline, chlorpheniramine, pyrilamine, cetirizine and prophenpyridamine; anti-inflammatories such as hydrocortisone, hydrocortisone acetate, dexamethasone, dexamethasone 21-phosphate, fluocinolone, medrysone, prednisolone, prednisolone 21-phosphate, prednisolone acetate, fluorometholone, betamethasone, and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; miotics and anticholinesterases such as pilocarpine, salicylate, acetylcholine chloride, physostigmine, eserine, carbachol, diisopropyl fluorophosphate, phospholine iodide and demecarium bromide; mydriatics such as atropine sulfate, cyclopentolate, homatropine, scopolamine, tropicamide, eucatropine and hydroxyamphetamine; sympathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol HCl and betaxolol HCl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide and other drugs such as prostaglandins, antiprostaglandins and prostaglandin precursors; antioxidants, NMDA receptor antagonists, nootropics, anti-apoptotic agents, neurotrophins, neuroprotective agents, cannabinoids, monoclonal antibodies, other proteins, and gene therapy. Other therapeutic agents known to those skilled in the art which are capable of controlled, sustained release into the ear in the manner described herein are also suitable for use in accordance with embodiments of the devices described herein.

The therapeutic agent can include, but is not limited to sodium thiosulfate to protect against cisplatin-induced hearing loss; NMDA receptor antagonists for the treatment of tinnitus (AM-101; Auris Medical); AM-111 containing the synthetic peptide D-JNKI-1 (D-stereoisomer of c-Jun N-terminal Kinase Inhibitor 1; Auris Medical) for otoprotection in acute inner ear hearing loss; dexamethasone for the treatment of Meniere's Disease; D-methionine (Southern Illinois University) to protect against Noise-induced hearing loss; LY411575 (a selective gamma secretase inhibitor that blocks Notch activation); and NT-3 neurotrophic factor.

The therapeutic agent can include, but is not limited to local anesthetics for delivery into the ear canal including benzocaine, antipyrine, butamben, dibucaine, lidocaine, oxybuprocaine, pramoxine, proparacaine, proxymetacaine, and tetracaine.

Various pharmaceutically acceptable carriers for the therapeutic agents described herein can include such as, for example, solids such as starch, gelatin, sugars, natural gums such as acacia, sodium alginate and carboxymethyl cellulose; polymers such as silicone rubber; liquids such as sterile water, saline, dextrose, dextrose in water or saline; condensation products of castor oil and ethylene oxide, liquid glyceryl triester of a lower molecular weight fatty acid; lower alkanols; oils such as corn oil, peanut oil, sesame oil, castor oil, and the like, with emulsifiers such as mono- or di-glyceride of a fatty acid, or a phosphatide such as lecithin, polysorbate 80, and the like; glycols and polyalkylene glycols including P407 and other combinations of polyethylene glycol and polypropylene glycol; aqueous media in the presence of a suspending agent, for example, sodium carboxymethylcellulose, sodium hyaluronate, sodium alginate, poly(vinyl pyrrolidone) and similar compounds, either alone, or with suitable dispensing agents such as lecithin, cyclodextrins, polyoxyethylene stearate and the like. The carrier may also contain adjuvants such as preserving, stabilizing, wetting, emulsifying agents or other related materials.

The devices described herein are preferably useful in the delivery of therapeutic agents within a short time-frame after noise exposure within the environment where the injury occurred, which are nonclinical sorts of settings. The ease of use of the devices described herein allow for delivery of agents within a time-frame that allows for prevention of permanent ear damage. The therapeutic agents can vary including LPT99, methotrexate, gentamicin, aminoglycosides, or steroids. The time-frame can also vary including less than 24 hours, less than 36 hours, less than 48 hours, less than 60 hours, or less than 72 hours after noise exposure.

The volume of medicament solution or suspension injected into the tympanic cavity can vary including 0.2, 0.5, 0.75, 1, 1.5, 2, 3, 4, and 5 mL. The solution of the drug can be administered to the tympanic cavity at a volume in the range of 0.2 to 5, 0.5 to 4, 0.75 to 3, and 1 to 2 mL.

Aspects of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive signals, data and instructions from, and to transmit signals, data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed. The claimed subject matter has been described in conjunction with the detailed description thereof, the foregoing description is intended to illustrate and not limit the scope of the claimed subject matter of the appended claims.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A system for delivering one or more therapeutics to a region of an ear, the region being internal to a tympanic membrane, the system comprising:
   a canal guide configured to be inserted within and fittingly engaged with walls of an ear canal, the canal guide comprising:
      a viewing lumen extending between a proximal end of the canal guide to a distal-most end of the canal guide, the distal-most end of the canal guide sized to remain external to the tympanic membrane; and
      a guide lumen extending from a proximal opening near the proximal end of the canal guide to a distal opening near the distal-most end of the canal guide, wherein the guide lumen curves from a first axis to a second axis, the first axis extending through the proximal opening and the second axis extending through the distal opening;
   a housing having a handle portion extending downwardly away from the canal guide, wherein the guide lumen of the canal guide is eccentric relative to a longitudinal axis of the canal guide, wherein the canal guide is adjustably attached to the housing such that the position of the guide lumen relative to the housing is adjusted by rotation, and wherein the guide lumen of the canal guide is adjustable around the longitudinal axis as the canal guide is rotated; and
   a needle assembly comprising a flexible shaft sized to extend through the guide lumen of the canal guide, the flexible shaft defining a fluid delivery lumen,
   wherein the canal guide provides alignment of the needle assembly within the ear canal relative to the tympanic membrane.

2. The system of claim 1, wherein the flexible shaft comprises a sharpened tip configured to penetrate the tympanic membrane.

3. The system of claim 1, wherein the distal opening from the guide lumen is positioned eccentric to a longitudinal axis of the canal guide.

4. The system of claim 1, wherein the longitudinal axis of the canal guide extends through the viewing lumen of the canal guide.

5. The system of claim 1, wherein the handle portion extends downwardly in a transverse direction relative to the central longitudinal axis of the canal guide and away from the canal guide such that the handle portion extends to a position rearwardly of the proximal opening of the guide lumen.

6. The system of claim 5, wherein the proximal opening of the guide lumen defines a receiving inlet that is larger than an inner diameter of the guide lumen and that is configured to receive the needle assembly.

7. The system of claim 6, wherein the inner diameter of the guide lumen is about 0.17 mm to about 1.00 mm and an interior diameter of the viewing lumen is larger than the inner diameter of the inner diameter of the guide lumen.

8. The system of claim 7, wherein the needle assembly includes a proximal coupler, a distal sharp tip, and the flexible shaft extending from the proximal coupler to the distal sharp tip, wherein the proximal coupler is larger than the receiving inlet of the guide lumen.

9. The system of claim 8, wherein the proximal coupler of the needle assembly is sized to remain external to the canal guide and the tympanic membrane while the distal sharp tip of the needle assembly is movable relative to the distal opening of the guide lumen to penetrate through the tympanic membrane for advancement into the middle ear.

10. The system of claim 9, wherein the proximal coupler of the needle assembly is matable with syringe having a plunger actuator for injection of a therapeutic fluid through the needle assembly in the guide lumen and into a targeted ear site interior to the tympanic membrane.

11. The system of claim 10, wherein the second axis of the distal opening of the guide lumen is parallel to and offset from the central longitudinal axis of the viewing lumen.

12. The system of claim 11, further comprising a lens positioned at a proximal end of the viewing lumen.

* * * * *